(12) United States Patent
Sherman

(10) Patent No.: US 7,402,314 B2
(45) Date of Patent: Jul. 22, 2008

(54) IN VIVO ACTIVATION OF TUMOR-SPECIFIC CYTOTOXIC T CELLS

(75) Inventor: Linda A. Sherman, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 320 days.

(21) Appl. No.: 09/277,064

(22) Filed: Mar. 26, 1999

(65) Prior Publication Data
US 2003/0064916 A1    Apr. 3, 2003

Related U.S. Application Data

(62) Division of application No. 08/860,232, filed as application No. PCT/US95/16415 on Dec. 14, 1995, now abandoned.

(51) Int. Cl.
*A61K 39/00* (2006.01)
(52) U.S. Cl. .................. 424/184.1; 424/9.1; 424/185.1; 424/194.1; 530/300; 514/2
(58) Field of Classification Search .................. 530/300; 514/4; 435/7.1
See application file for complete search history.

(56) References Cited

U.S. PATENT DOCUMENTS

| | | | |
|---|---|---|---|
| 4,950,598 A * | 8/1990 | Engleman et al. ........ | 435/172.2 |
| 5,112,948 A | 5/1992 | Jones | |
| 5,292,642 A | 3/1994 | Jones | |
| 5,434,247 A | 7/1995 | Jones | |
| 5,679,641 A | 10/1997 | Melief et al. | |
| 5,726,023 A * | 3/1998 | Cheever et al. ............ | 435/7.1 |
| 6,419,931 B1 * | 7/2002 | Vitiello et al. ........... | 424/201.1 |

FOREIGN PATENT DOCUMENTS

| WO | WO 93 24525 | 12/1993 |
|---|---|---|
| WO | WO 94 20127 | 2/1994 |
| WO | WO 94 20127 | 9/1994 |

OTHER PUBLICATIONS

Yoshino, I et al, 1994, J Immunol, 152(5): 2393-400.*
Stedman's medical dictionary, 25th ed, 1990, pp. 1652-1653.*
White et al, 2001, Ann Rev Med, 52: 125-145.*
Gu K et al, Cancer letters, Feb. 6, 1996,99(2): p185-9.*
Costa MJ et al, American J Clin Pathol, 1995, v. 104, n. 6, p. 634-642.*
Danova M et al, European journal of histochemistry, 1992, 36(3): p.279-88.*
Sherman LA. Art. Rev. Immunol 18 (1-2): 47-54, 1998.*
Boon, Adv. Cancer Res. 58:177-210, 1992.*
Jura. Science, 278:1041-1042, 1997.*
Jain, Science, 271:5-65, 1994.*
Curti, Crit. Rev. Oncol/Hematol. 14:29-39, 1993.*
Freshney, Cult. Animal Cells. A Manual of Basic Tech. Alan R. Liss, N.Y., p. 4, 1983.*
Dermer, Bio/Technology , 12:320, 1994.*

Di Fiore, et al., *Science 237*: 178 (1987).
Dittmer, et al., *Nature Gen. 4*: 42 (1993).
Falk, et al., *Nature 351*: 290 (1991).
Harlow, et al., *Mol. Cell. Biol. 5*: 1601 (1985).
Hinds, et al., *Cell Growth Diff. 1*: 571 (1990).
Houbiers, et al., *Eur. J. Immunol. 23*: 2072-2077 (1993).
Hunt, et al., *Science 255*: 1261 (1992).
Ioannides, et al., *Cellular Immunol. 151*: 225-234 (1993).
Ioannides, et al., *J. Immunol. 146*: 1700 (1991).
Irwin, et al., *J. Exp. Med. 170*: 1091 (1989).
Melief and Kast, *Curr. Op. Immunol. 5*: 709-713 (1993).
Vitiello, et al., *J. Exp. Med. 173*: 1007-1015 (1991).
Winter, et al., *Cancer Res. 52*: 4168-74 (1992).
Yoshino, et al., *J. Immunol. 152*: 2393 (1994).
Guo, et al., "Different Length Peptides Bind to HLA-Aw68 Similarly at Their Ends But Bulge Out in the Middle", *Nature 360*: 364-366 (1992).
Boon, "Tumor Antigens Recognized by Cytolytic T Lymphocytes: Present Perspectives for Specific Immunotherapy", *Int. J. Cancer 54*: 177-180 (1993).
Melief, et al., "Potential Immunogenicity of Oncogene and Tumor Suppressor Gene Products", *Curr. Opin. Immunol. 5*: 709-713 (1993).
Houbiers, et al., "In Vitro Induction of Human Cytotoxic T Lymphocyte Responses Against Peptides of Mutant and Wild-Type p53", *Eur. J. Immunol. 23*: 2072-2077 (1993).
Ruppert, et al., "Prominent Role of Secondary Anchor Residues in Peptide Binding to HLA-A2.1 Molecules", *Cell 74*: 929-937 (1993).
Nijman, et al., "p53, a Potential Target for Tumor-Directed T Cells", *Immunol. Lett. 40*: 171-178 (1994).
Pietras, et al., "Antibody to HER-2/*neu* Receptor Blocks DNA Repair After Cisplatin in Human Breast and Ovarian Cancer Cells", *Oncogene 9*: 1829-1838 (1994).
Tilkin, et al., "Primary Proliferative T Cell Response to Wild-Type p53 Protein in Patients with Breast Cancer", *Eur. J. Immunol. 25*: 1765-1769 (1995).
Nijman, et al., "Characterization of Cytotoxic T Lymphocyte Epitopes of a Self-Protein, p53, and a Non-Self-Protein, Influenza Matrix: Relationship Between Major Histocompatibility Complex Peptide Binding Affinity and Immune Responsiveness to Peptides", *J. Immunotherapy 14*: 121-126 (1993).

(Continued)

*Primary Examiner*—Shanon Foley
*Assistant Examiner*—Minh-Tam Davis
(74) *Attorney, Agent, or Firm*—Hugh Wang; Thomas Fitting; Michael J. McCarthy

(57) ABSTRACT

The present invention relates to methods and compositions of activating cytotoxic T lymphocytes (CTLs) in vivo with specificity for particular antigenic peptides, and to methods and compositions of using activated CTLs in vivo for the treatment of a variety of disease conditions. In some preferred embodiments, the invention provides methods of employing a polypeptide of the amino acid sequence VMAGVGSPYV to specifically activating CTLs in subjects having a breast cancer overexpressing a Her-2/Neu protein, and methods of using the polypeptide to treat such subjects.

16 Claims, 22 Drawing Sheets

OTHER PUBLICATIONS

Spitler, "Cancer Vaccines: The Interferon Analogy", *Cancer Biotherapy 10*: 1-3 (1995).

Ezzell, "Cancer "Vaccines": An Idea Whose Time Has Come?", *J. NIH Res. 7*: 46-49 (1995).

Allen, et al., "Identification of the T-Cell and Ia contact residues of a T-cell Antigenic Epitope", *Nature 327*: 713-715 (1987).

Sette, et al., "Structural Characteristics of an Antigen Required for its Interaction with Ia and Recognition by T cells", *Nature 328*: 395-399 (1987).

Deres, et al., "In Vivo Priming of Virus-Specific Cytotoxic T lymphocytes with Synthetic Lipopeptide Vaccine", *Nature 342*: 561-564 (1989).

Vitiello, et al., "Analysis of the HLA-Restricted Influenza-Specific Cytotoxic T Lymphocyte Response in Transgenic Mice Carrying a Chimeric Human-Mouse Class I Major Histocompatibility Complex", *J. Exp. Med. 173*: 1007-1015 (1991).

Jardetzky, et al., "Identification of Self Peptides Bound to Purified HLA-B27", *Nature 353*: 326-329 (1991).

Farouqi, et al., "Establishment of T-Lymphoid Cell Lines from Morroccan Patients with Tropical Spastic Paraparesis", *AIDS Research and Human Retroviruses 8*: 1209-1213 (1992).

van der Bruggen, et al., "Molecular Definition of Tumor Antigens Recognized by T Lymphocytes", *Curr. Opin. Immunol. 4*: 608-612 (1992).

Lane, "p53, Guardian of the Genome", *Nature 358*: 15-16 (1992).

Ullrich, et al., "The p53 Tumor Suppressor Protein, a Modulator of Cell Proliferation", *J. Biol. Chem. 267*: 15259-15262 (1992).

Hartwell, "Defects in a Cell Cycle Checkpoint May be Responsible for the Genomic Instability of Cancer Cells", *Cell 71*: 543-546 (1992).

Epstein, et al., "Synthetic Phosphopeptide Immunogens Yield Activation-Specific Antibodies to the c-erbB-2 Receptor", *Proc. Natl. Acad. Sci. USA 89*: 10435-10439 (1992).

* cited by examiner

Lane 1 represents lysis of targets by an M1 specific, A2.1 restricted CTL clone in the absence of addition of the M1 peptide. Lanes 2-9 all received 0.1 ug of the M1 peptide of influenza along with 10 ug of the following:
2. FLU NP 365-373
3. VSV-N-52-59
4. HIV-Pol 510-518
5. p53 264-272
6. p53 149-157
7. p53 65-73
8. p53 25-35
9. none

IN VIVO ACTIVATION OF TUMOR-SPECIFIC CYTOTOXIC T CELLS

This application is a divisional of U.S. patent application Ser. No. 08/860,232 (filed on Aug. 8, 1997, now abandoned), which is a national phase entry of PCT/US95/16415, (filed on Dec. 14, 1995), which claims priority to U.S. patent application Ser. No. 08/355,558 (filed on Dec. 14, 1994, now abandoned).

STATEMENT OF GOVERNMENT SUPPORT

This invention was made in part by government support by the National Institutes of Health Grant No. CA25803. The U.S. Government therefore has certain rights in the invention.

TECHNICAL FIELD

The present invention relates to methods, compositions, and peptides useful in activating CTLs in vivo with specificity for particular antigenic peptides. The invention also discloses the use of activated CTLs in vivo for the treatment of a variety of disease conditions, and compositions appropriate for these uses. Diagnostic kits, components, and methods are also described herein.

BACKGROUND

The efficiency with which the immune system cures or protects individuals from infectious disease has always been intriguing to scientists, as it has been believed that it might be possible to activate the immune system to combat other types of diseases. Such diseases include cancer, AIDS, hepatitis and infectious disease in immunosuppressed patients. While various procedures involving the use of antibodies have been applied in those types of diseases, few if any successful attempts using cytotoxic T lymphocytes have been recorded. Theoretically, cytotoxic T lymphocytes would be the preferable means of treating the types of disease noted above. However, no useful in vivo procedures have been available to specifically activate cytotoxic T lymphocytes.

Cytotoxic T lymphocytes (CTLs), which are also called cytotoxic T cells or CD8 cells, represent the main line of defense against viral infections. CTLs specifically recognize and kill cells which are infected by a virus. Thus, the cost of eliminating a viral infection is the accompanying loss of the infected cells. The T cell receptors on the surface of CTLs cannot recognize foreign antigens directly. In contrast to antibodies, antigen must first be presented to the receptors.

The presentation of antigen to T cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leucocyte antigen) complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T cells.

MHC products are grouped into three major classes, referred to as I, II, and III. T cells that serve mainly as helper cells express CD4 and are primarily restricted by Class II molecules, whereas CTL-(CD8-) expressing cells, which mostly represent cytotoxic effector cells, interact with Class I molecules.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T cells. In contrast, complexes of MHC molecules with peptides derived from normal cellular products play a role in "teaching" the T cells to tolerate self peptides, in the thymus. Class I molecules do not present entire, intact antigens; rather, they present peptide fragments thereof, "loaded" onto their "peptide binding groove".

For many years, immunologists have hoped to raise specific cytotoxic cells targeting viruses, retroviruses and cancer cells. While targeting against viral diseases in general may be accomplished in vivo by vaccination with live or attenuated vaccines, no similar success has been achieved with retroviruses or with cancer cells. Moreover, the vaccine approach has not had the desired efficacy in immunosuppressed patients. One way around this difficulty would be to immunize a healthy individual, isolate the CTLs from this individual, and inject these CTLs into the disease-afflicted person.

However, this experimental protocol is not always useful, as it is neither practical (nor ethical) in many circumstances to endeavor to immunize healthy individuals with tumor cells. Furthermore, it is problematic, at best, to endeavor to activate CTLs to recognize abnormal cells expressing abnormally high levels of peptides that are expressed on normal cells in lower quantities in normal, healthy individuals.

The use of mouse strains (including transgenic strains) to generate activated CTLs has not always been practical, particularly if the murine strain is unable to raise an immunologic response to the immunogen. Failure to raise an immunologic response may be due either to failure of the murine immune system to recognize the antigen, or its failure to generate activated cells that are compatible with the intended recipient of activated CTLs for therapeutic purposes.

For example, it has been observed that peptides are unique for a given MHC; in other words, certain antigenic peptides bind preferentially to particular MHC species and do not bind well to others, even in the absence of the "preferred" MHC molecule. Furthermore, MHC molecules are highly polymorphic, which fact generates at least two problems. First, the CTLs of an individual can only interact with peptides bound to precisely those three to six Class I molecules present in that individual. Second, CTLs react violently with all Class I molecules which are different from those expressed in the individual from whom the CTLs are obtained, regardless of what peptides the Class I molecules contain. This reactivity has been observed for some time and is termed allo-reactivity. It is the underlying cause of the immune rejection of transplanted organs.

Thus, apart from the rather heroic experimental protocol in which one individual is used as the donor of activated CTLs to another individual, it is difficult to find two unrelated persons with the exact same setup of Class I molecules. For this reason, at least one researcher has taken the rather non-specific approach of "boosting" existing CTLs by incubating them in vitro with IL-2, a growth factor for T cells. However, this protocol (known as LAK cell therapy) will only allow the expansion of those CTLs which are already activated. As the immune system is always active for one reason or another, most of the IL-2 stimulated cells will be irrelevant for the purpose of combating the disease. In fact, it has not been documented that this type of therapy activates any cells with the desired specificity. Thus, the benefits of LAK cell therapy are controversial at best, and the side effects are typically so severe that many studies have been discontinued.

Class I molecules bind peptides in a specific manner. All peptides have to be about 8-11 amino acids in length and their sequences must fit the peptide-binding pocket of the Class I molecules. In this respect, Class I molecules display some resemblance to antibodies. However, while a given antibody tends to bind only one antigen, a given Class I molecule can bind many hundred different peptides. As the number of viruses and other pathogens is quite large, it is apparent that our immune defense would be poor if we had only a single Class I molecule, even if it is capable of binding and altering many different peptides. For this reason, all humans have between three and six different Class I molecules, which can each bind many different types of peptides. Accordingly, the CTLs can recognize many thousands of peptides bound to one or another Class I molecule.

As selection seems to be the dominant force in evolution, pathogens emerge which cannot be recognized efficiently by the immune system. Thus, for example, a viral sequence, which gives rise to peptides that bind efficiently to a variety of Class I molecules, may mutate such that it is not recognized by any of the three to six Class I molecules present in an individual. This virus may therefore not be recognized by the immune system and may consequently cause the death of the affected individual. If all individuals had an identical set of Class I molecules, such a virus might conceivably eliminate an entire species.

However, individual variation is a safeguard against that possibility, as some 100 different forms of Class I molecules are present in the population.

If Class I molecules can bind a variety of peptides, including peptides derived from our own cellular proteins, one may wonder why the CTLs of the immune system do not recognize and destroy our own tissues. While the answer to this question is not entirely clear, two distinct mechanisms are presently believed to be operating. First, CTLs that can react with self peptides are eliminated in the thymus. Second, CTLs become non-responsive (anergic) to self peptides in the peripheral organs of the immune system. Since every possible type or epitope of cellular proteins is not synthesized by the cells in the thymus, the second mechanism would appear to be the more likely explanation. This mechanism appears to be operational for the level of self peptides normally encountered. If this level is increased by some means, it can be shown that individuals do indeed have CTLs that can recognize and destroy cells expressing self peptides. This latter observation is significant with regard to the concept of using the immune system to eliminate tumor cells.

Recently, it has become apparent that mutant and wild-type peptides derived from cellular oncogene proteins can be recognized by CTLs. This suggests that self peptides encoded by non-mutant genes, in addition to the peptides encoded by mutant genes, can be potential targets for T cell responses against tumor cells. (See, e.g., Melief and Kast, Curr. Op. Immunol. 5: 709-713 (1993); Boon, Adv. Cancer Res. 58: 177-210 (1992); Van der Bruggen, et al., Curr. Op. Immunol. 4: 608-612 (1992).)

Irrespective of the mode of activity, it is evident that the CTL response with respect to various tumor antigens is deficient in many cases. It would be desirable to stimulate the immune response in these individuals to respond to appropriate tumor antigens and thereby eliminate the cells and tissues so affected. Further, as there is no currently available vaccine for malignancies such as breast cancers, it is desirable to establish such a vaccine, preferably based on a range of antigenic determinants.

Accordingly, it is an object of the present invention to provide agents that strengthen or boost the ability of the cellular immune system to fight tumors and other malignancies. It is a further object to provide pharmaceutical compositions that strengthen or boost the cellular immune system for fighting tumor-related disease processes, both with reference to therapeutic and prophylactic uses.

These and other objects and advantages of the present invention, as well as additional inventive features, will be apparent from the description of the invention provided herein.

BRIEF SUMMARY OF THE INVENTION

The present invention provides agents that strengthen or boost the cellular immune system to fight or prevent tumor growth or proliferation, or the growth or proliferation of other malignancies. In various embodiments of the present invention, the condition to be treated may comprise cancer, tumors, neoplasia, viral or retroviral infection, autoimmune or autoimmune-type conditions.

For example, the present invention is directed to a polypeptide having substantial homology with a CTL epitope selected from the group consisting of LLPENNVLSPL (SEQ ID NO 1); RMPEAAPPV (SEQ ID NO 2); STPPPGTRV (SEQ ID NO 3); LLGRNSFEV (SEQ ID NO 4); KIFGSLAFL (SEQ ID NO 10); TLQGLGISWL (SEQ ID NO 11); VMAGVGSPYV (SEQ ID NO 12); VLQGLPREYV (SEQ ID NO 13); and ILLVVVLGV (SEQ ID NO 14), or to a molecule that includes such a polypeptide or an analog or sequential subset thereof.

In addition, the present invention provides methods of provoking an immune response to p53 or Her-2/Neu antigens, comprising contacting a suitable cytotoxic T lymphocyte with an immune-response-provoking, effective amount of a molecule comprising a peptide selected from the group of epitopes listed above. The present invention further provides pharmaceutical compositions comprising at least one of the CTL-specific epitopes recited herein.

Thus, in one embodiment, the present invention contemplates a polypeptide capable of specifically activating cytotoxic T lymphocytes in vivo, wherein the cytotoxic T lymphocytes (CTLs) specifically target malignant cells. In one variation, the polypeptide is derived from human p53 protein. Various p53 polypeptides are useful in this regard, including those with amino acid residue sequences such as STPPPGTRV (SEQ ID NO 3), LLGRNSFEV (SEQ ID NO 4), LLPENNVLSPL (SEQ ID NO 1), RMPEAAPPV (SEQ ID NO 2), and sequential subsets thereof.

In another variation, the polypeptide is derived from human Her-2/Neu protein. Various Her-2/Neu polypeptides are useful in this regard, including those with amino acid residue sequences such as KIFGSLAFL(SEQ ID NO 10), VMAGVGSPYV(SEQ ID NO 12), TLQGLGISWL (SEQ ID NO 11), VLQGLPREYV (SEQ ID NO 13), ILLVVVLGV (SEQ ID NO 14) and sequential subsets thereof.

Polypeptides having substantial homology with CTL epitopes are also disclosed herein. CTL epitopes identified with tumor-associated antigens are particularly preferred. Preferred CTL epitopes of the present invention include p53 and Her-2/Neu epitopes. Exemplary epitopes include STPPPGTRV (SEQ ID NO 3), LLGRNSFEV (SEQ ID NO 4), LLPENNVLSPL (SEQ ID NO 1), RMPEAAPPV (SEQ ID NO 2), KIFGSLAFL (SEQ ID NO 10), VMAGVGSPYV (SEQ ID NO 12), TLQGLGISWL (SEQ ID NO 11), VLQGLPREYV (SEQ ID NO 13), and ILLVVVLGV (SEQ ID NO 14). The following CTL epitopes are somewhat more preferred: STPPPGTRV (SEQ ID NO 3), LLGRNSFEV (SEQ ID NO 4), KIFGSLAFL (SEQ ID NO 10), VMAGVGSPYV (SEQ ID NO 12), and homologs, analogs and sequential subsets thereof.

The present invention also discloses a variety of pharmaceutical compositions. One embodiment of such a composition comprises a polypeptide having substantial homology with a CTL epitope; exemplary and preferred epitopes are noted above. A composition of the present invention may further comprise a pharmaceutically acceptable carrier.

Populations of specific cytotoxic T cells capable of lysing tumor cells displaying a specific peptide are also encompassed by the present invention. In one embodiment, the peptide is displayed exogenously. In another, the peptide is displayed endogenously.

In one embodiment of the disclosed populations, the CTLs are generated via in vivo immunization. In one variation, the specific peptide is derived from p53; in another, the specific peptide is derived from Her-2/Neu. Exemplary peptides useful according to the invention have already been identified hereinabove.

The present invention further contemplates a variety of useful anti-tumor vaccines. In one embodiment, a vaccine comprises an immunogenically effective amount of a cytotoxic T-lymphocyte-stimulating peptide. In alternative embodiments, the peptide may be derived from endogenously or exogenously displayed or processed proteins, analogs or portions thereof; preferably, such proteins, analogs, and portions thereof are tumor-associated. For example, p53 and Her-2/Neu proteins, analogs, and portions (or sequential subsets) thereof are preferred according to the present invention.

In various embodiments, the peptide for use in (or as) a vaccine is selected from the following group: STPPPGTRV (SEQ ID NO 3), LLGRNSFEV (SEQ ID NO 4), LLPENNVLSPL (SEQ ID NO 1), RMPEAAPPV (SEQ ID NO 2), KIFGSLAFL (SEQ ID NO 10), VMAGVGSPYV (SEQ ID NO 12), TLQGLGISWL (SEQ ID NO 11), VLQGLPREYV (SEQ ID NO 13), and ILLVVVLGV (SEQ ID NO 14). In alternative variations, the peptide may be linked to a carrier. It may also be introduced into a mammal as a homopolymer, or as a heteropolymer.

The invention also discloses methods of generating activated CTL cells in vivo. In one embodiment, the method comprises contacting, in vivo, CTL cells with antigen-loaded Class I molecules surface-expressed on eucaryotic cells—e.g. mammalian cells, and more preferably murine cells—for a time period sufficient to activate, in an antigen-specific manner, the CTL cells. In one variation, the Class I molecules are human Class I MHC molecules. In another variation, the Class I molecules are chimeric human-mouse Class I MHC molecules. Appropriate antigens may be selected from the proteins, polypeptides, analogs and sequential subsets thereof which have already been described above.

The method may further comprise separating the activated CTL cells from the antigen-loaded Class I MHC molecules; suspending the activated CTL cells in an acceptable carrier or excipient; and administering the suspension to an individual in need of treatment.

The invention further contemplates methods of specifically killing target cells in a patient. In one embodiment, such a method comprises the steps of administering an immunogenic polypeptide specific to the target cells to an animal, thereby generating a population of antigen-loaded Class I molecules displaying the polypeptides on their cell surfaces; contacting, in vivo, a population of CTL cells with the population of antigen-loaded Class I molecules for a time period sufficient to activate, in an antigen-specific manner, the CTL cells; harvesting the activated CTL cells from the animal; and administering the activated CTL cells to the patient.

As noted previously, a variety of proteins, polypeptides, portions and sequential subsets thereof are available for use in this regard. For example, useful peptides include the following sequences: LLPENNVLSPL (SEQ ID NO 1), RMPEAAPPV (SEQ ID NO 2), STPPPGTRV (SEQ ID NO 3), LLGRNSFEV (SEQ ID NO 4), KIFGSLAFL (SEQ ID NO 10), VMAGVGSPYV (SEQ ID NO 12), and sequential subsets thereof. In various embodiments, the Class I molecules are human Class I MHC molecules. In others, the Class I molecules are chimeric human-mouse Class I MHC molecules.

As noted previously, various methods of specifically killing target cells are contemplated herein. Another exemplary method uses specific, activated CTLs, prepared according to the following steps: obtaining a fluid sample containing T cells from an individual in need of treatment; loading empty Class I MHC molecules with at least one species of antigenic peptide, wherein the peptide is substantially homologous to at least a portion of a peptide derived from the target cell; admixing the T cells with an amount of peptide-loaded Class I MHC molecules sufficient to produce activated CTLs; harvesting the activated CTLs; and administering the activated CTLs to the individual. Useful antigenic molecules have already been disclosed hereinabove.

Also contemplated by the present invention are methods of provoking an immune response to a tumor-associated antigen. In one method, a cytotoxic T lymphocyte is contacted with an immune response-provoking amount of a molecule comprising a peptide derived from a tumor-associated protein. Exemplary proteins, polypeptides, analogs, homologs, and sequential subsets thereof are listed above and may be used in various embodiments of this method. For example, some peptides useful according to the present method include the amino acid residue sequences STPPPGTRV (SEQ ID NO 3), LLGRNSFEV (SEQ ID NO 4), KIFGSLAFL (SEQ ID NO 10), VMAGVGSPYV (SEQ ID NO 12), or sequential subsets thereof.

In one variation of the foregoing method, the contacting step occurs in vivo—preferably, in a mammal. In another embodiment, the contacting occurs in vitro. In another variation, the method further comprises returning the contacted cytotoxic T cells to the host. Another embodiment discloses that a polypeptide is co-administered with a second polypeptide that induces a T helper response. In one variation, the polypeptide and the T helper-inducing polypeptide are conjugated to one another.

Also disclosed herein are methods of identifying specific cytotoxic T cells (CTLs) responsive to a specific T cell epitope. One such method includes the following steps: obtaining a test sample of lymphocytes from an individual, wherein the test sample is to be assayed for the presence of the specific CTLs; contacting target cells with a molecule comprising a peptide selected from the group consisting of STPPPGTRV (SEQ ID NO 3), LLGRNSFEV (SEQ ID NO 4), KIFGSLAFL (SEQ ID NO 10), VMAGVGSPYV (SEQ ID NO 12), and sequential subsets thereof, wherein the target cells are of the same HLA class as the lymphocytes to be tested for the specific CTLs; contacting the test sample with a molecule according to step b, under conditions sufficient to restimulate the specific CTLs to respond to appropriate target cells; and determining whether the test sample of lymphocytes exerts a cytotoxic effect on the target cells, thereby confirming the presence of the specific CTLs.

Methods of detecting specific cytotoxic T cells (CTLs) having receptors capable of binding a specific T cell epitope in a tissue sample are also disclosed herein. One such method comprises the following steps: obtaining a test sample of lymphocytes from an individual, wherein the test sample is to be assayed for the presence of the specific CTLS; contacting the test sample with a molecule comprising a label and a tumor-associated peptide, to form an admixture; maintaining the admixture under suitable assay conditions for a predetermined period of time, sufficient to restimulate any specific CTLs in the test sample to respond to appropriate target cells; harvesting such contacted cells and washing with medium in the absence of the labeled molecule sufficient to remove any unbound labeled molecule; and measuring the bound labeled molecule using suitable measuring means.

Tumor-associated proteins and polypeptides for use according to the disclosed methods are described in detail herein. The invention also contemplates various alternative procedures for use according to the above-noted method. For example, the cells may be lysed using a hypotonic solution with or without unlabeled molecule—or via other means known in the art—and preparing a membrane fraction that is free of unbound labeled molecule.

The present invention also discloses methods of detecting anti-p53 antibodies in an individual. One such method comprises the following steps: obtaining a fluid sample from an individual to be tested; adding a predetermined amount of p53 polypeptide to the sample, to form an admixture; maintaining the admixture under biological assay conditions for a period of time sufficient to allow the p53 polypeptide to immunoreact with any anti-p53 antibodies present in the sample; and assaying for the presence of an immunoreaction product, thereby confirming the presence of anti-p53 antibodies. As before, useful p53 proteins, polypeptides, analogs, homologs, and sequential subsets thereof are described herein. Exemplary p53 polypeptides may include the following amino acid residue sequences (or sequential subsets thereof): STPPPGTRV (SEQ ID NO 3), LLGRNSFEV (SEQ ID NO 4), KIFGSLAFL (SEQ ID NO 10), VMAGVGSPYV (SEQ ID NO 12). It is also contemplated that the p53 polypeptide comprises two or more different polypeptides, e.g., polypeptides including sequences selected from the group consisting of STPPPGTRV (SEQ ID NO 3), LLGRNSFEV (SEQ ID NO 4), KIFGSLAFL (SEQ ID NO 10), VMAGVGSPYV (SEQ ID NO 12), and sequential subsets thereof.

The present invention also contemplates various assay systems, including diagnostic assay systems. One exemplary assay system in kit form comprises a package containing, in an amount sufficient to perform at least one assay, at least one species of polypeptide comprising no more than about 50 amino acid residues and including an amino acid residue sequence derived from a tumor-associated protein. For example, in one embodiment, the tumor-associated protein is p53, and useful polypeptides may thus include one or more of the following amino acid residue sequences, or sequential subsets thereof: LLPENNVLSPL (SEQ ID NO 1), RMPEAAPPV (SEQ ID NO 2), STPPPGTRV (SEQ ID NO 3), or LLGRNSFEV (SEQ ID NO 4). Polypeptides substantially homologous thereto are also useful as described.

In various embodiments, the polypeptide may be affixed to a solid matrix. In another variation, the polypeptide comprises more than one species of polypeptide and wherein the species are present as an admixture. An assay system may further include, in a separate package, a labeled specific binding agent for signaling the presence of a polypeptide-containing immunoreaction product.

Another assay system of the present invention comprises an assay system in kit form comprising a package containing, in an amount sufficient to perform at least one assay, an antibody combining site-containing molecule capable of immunoreacting with a tumor-associated antigen. As noted previously, a wide variety of useful antigens are disclosed herein.

In one embodiment, the antibody combining site-containing molecule is affixed to a solid matrix. In another variation, the molecule is labeled.

Antibody combining site-containing molecules according to the present invention include antibody molecules or immunologically active portions thereof, including intact immunoglobulin molecules, substantially intact immunoglobulin molecules and those portions of an immunoglobulin molecule that contain the paratope, including those portions known in the art as Fab, Fab', F(ab')$_2$ and F(v). In an exemplary embodiment, an antibody molecule of the present invention is able to immunoreact with a polypeptide as disclosed hereinabove. In one embodiment, the antibody molecule is monoclonal; in another, the antibody molecule is polyclonal. The invention further contemplates compositions comprising one or more antibody molecules as disclosed herein. In addition, the invention discloses hybridomas capable of secreting molecules containing antibody combining sites.

The invention further contemplates a molecule comprising a polypeptide having substantial homology with a CTL epitope. Various CTL epitopes are disclosed above. In an exemplary embodiment, CTL epitopes are selected from the group consisting of STPPPGTRV (SEQ ID NO 3), LLGRNSFEV (SEQ ID NO 4), KIFGSLAFL (SEQ ID NO 10), VMAGVGSPYV (SEQ ID NO 12), and sequential subsets thereof.

In one variation, the molecule comprises at least about eight amino acids and fewer than about 50 amino acids. In another, the molecule comprises at least about eight amino acids and fewer than about thirteen amino acids. In yet another embodiment, the polypeptide has an amino acid residue sequence substantially homologous to that of any of the CTL epitopes.

Another variation provides that the polypeptide is conjugated to a substance, wherein the substance is selected from the group consisting of a radiolabel, an enzyme, a fluorescent label, a solid matrix, a carrier, and a second CTL epitope. In one embodiment, the substance is a second CTL epitope; in another, the second epitope is a T helper epitope. It is further contemplated that the carrier may comprise an immunogenic lipid or protein. Moreover, the polypeptide may be conjugated to the substance indirectly by a linker.

It is expressly to be understood that various embodiments as disclosed above and hereinbelow may be combined appropriately to describe further alternative embodiments of the within-described invention.

BRIEF DESCRIPTION OF THE DRAWINGS

FIG. 2 illustrates CTL-mediated lysis of target cells which have p53-specific peptides bound to the cell surface as described in Example 1B1. The percent specific lysis (%-SL) is given on the Y-axis and the ratio of effector to target cells (E:T) is given on the X-axis.

FIG. 3 illustrates CTL-mediated lysis of target cells which express endogenous p53 specific peptides bound to A2 on the cell surface as described in Example 1B2b. The percent specific lysis (%-SL) is given on the Y-axis and the ratio of effector to target cells (E:T) is given on the X-axis.

FIG. 4 illustrates CTL-mediated lysis of Saos-2 target cells as described in Example 1B2b. The percent specific lysis (%-SL) is given on the Y-axis and the ratio of effector to target cells (E:T) is given on the X-axis.

In FIGS. 10A and B, the CTL cell lines were A2$K^b$149-primed; in FIGS. 10C and D, the CTLs were primed with A2$K^b$264. In FIGS. 10E and F, the CTL cell lines were A2 149-primed; 10G and H, the CTLs were primed with A2 264. In FIGS. 10A-H, effector:target (E:T) ratios were plotted against specific $^{51}$Cr release (%). CTL were assayed for cytotoxicity in a 5-hour $^{51}$Cr release assay against the indicated targets: FIGS. 10A and C: T2A2/$K^b$ (open circles, ○) or T2A2/$K^b$+p53.149-157 (closed circles, ●) or T2A2/$K^b$+p53.264-272 (closed squares, ■). FIGS. 10E and G: T2 (○) or T2 pulsed with p53.149-157 (●) or p53.264-272 (■). FIGS. 10B, D, F, H: Saos-2 (open triangles, △) or the same cells transfected with the human p53 gene, Saos-2/175 (closed triangles, ▲). (See, e.g., Dittmer, et al., *Nature Genet.* 4: 42-6 (1993); Masuda, et al., *PNAS USA* 84: 7716-9 (1987); Hinds, et al., *Cell Growth Diff.* 1: 571-580 (1990).) Both lines expressed similar levels of A2.1 as detected by flow cytometry. (See, e.g., Irwin, et al., *J. Exp. Med.* 170: 1091-1101 (1989).)

In FIG. 13A, the open circles (○) represent H7-A2.1/$K^b$×CD8, while the closed circles ●) represent H7-A2.1.

In FIG. 14A, closed circles (●) represent NCI-H1355, while closed squares (■) represent NCI-H1355-PA2.1. In FIG. 14B, closed circles (●) represent MDA-231, while closed squares (■) represent MDA-231-PA2.1. In FIG. 14C, closed circles (●) represent SAOS-175, while closed squares (■) represent SAOS-175-PA2.1. In FIG. 14D, closed circles (●) represent T98G, while closed squares (■) represent T98G-PA2.1.

DETAILED DESCRIPTION OF THE INVENTION

A. Definitions

Figure 1:
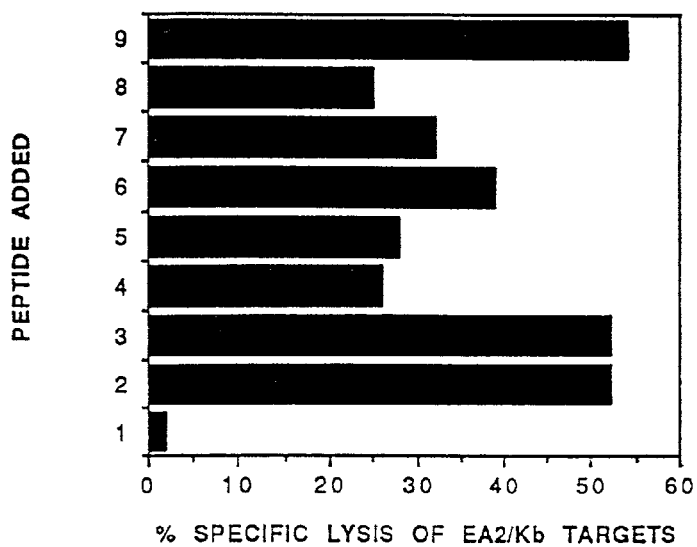
FIG. 1 illustrates the ability of test peptides to bind A2.1 on the surface of target cells in binding inhibition assay as described in Example 1A2e. The percent specific lysis (% specific lysis of EA2/K$^b$ targets) is given on the X-axis and the test peptide is given on the Y-axis. The results of peptides M1 (1), FLU NP 365-373 (2), VSV-N-52-59 (3), HIV-Pol 510-518 (4), p53 264-272 (5), p53 149-157 (6), p53 65-73 (7), p53 25-35 (8), and no peptide (9) are given.
Figure 2A:
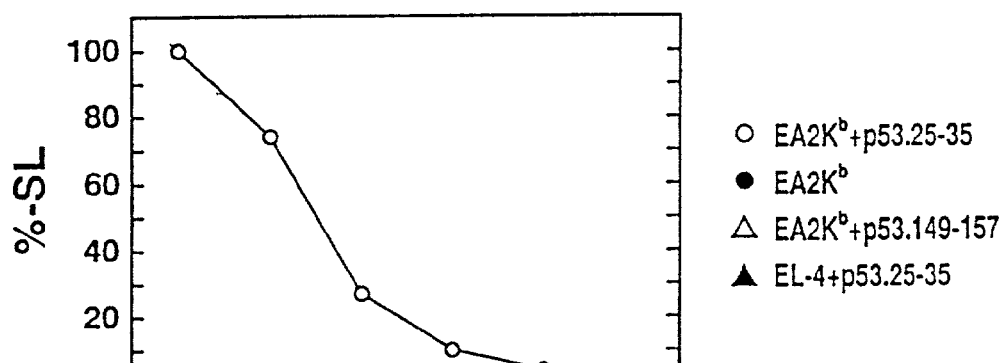
FIG. 2A illustrates lysis of target cells with CTL that were generated from transgenic mice immunized with the p53.25-35 peptide (CTL A2K$^b$ 25). The results of p53 peptides p53.25-35 and p53.149-157 peptide bound to A2.1/K$^b$ on the surface of the EA2K$^b$ cells (EA2K$^b$+p53.25-35 (open circle) and EA2K$^b$+p53.149-157 (open triangle), respectively), EA2K$^b$ cells without peptide (EA2K$^b$; closed circle and EL-4 cells incubated in the presence of p53.25-35 cells (EL-4+ p53.25-35; closed triangle) are given.
Figure 2B:
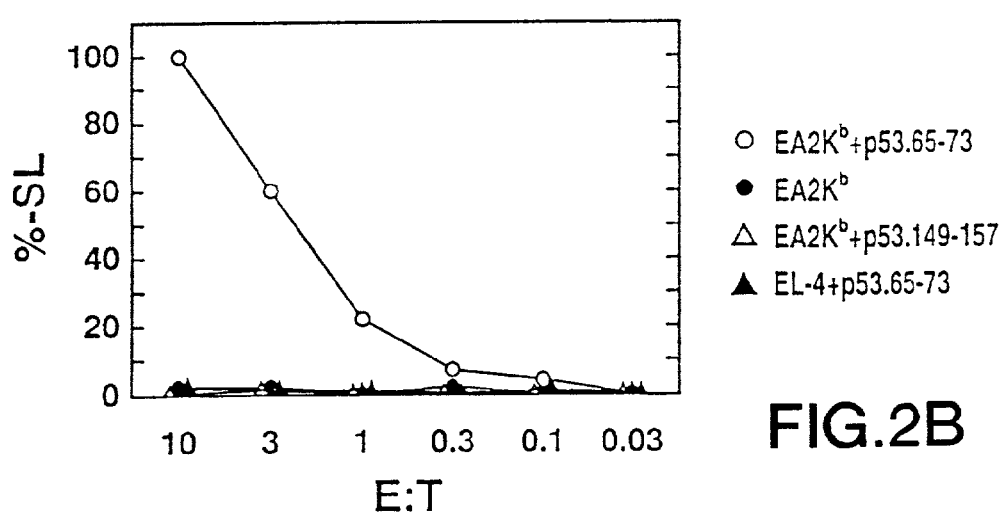
FIG. 2B illustrates lysis of target cells with CTL that were generated from transgenic mice immunized with the p53.65-73 peptide (CTL A2K$^b$ 65). The results of p53 peptides p53.65-73 peptide bound to A2.1/K$^b$ on the surface of the EA2K$^b$ cells (EA2K$^b$+p53.65-73; open circle), EA2K$^b$+ p53.149-157; open triangle, EA2K$^b$; closed circle, and EL-4 cells incubated in the presence of p53.65-73 cells (EL-4+ p53.65-73; closed triangle) are given.
Figure 2C:
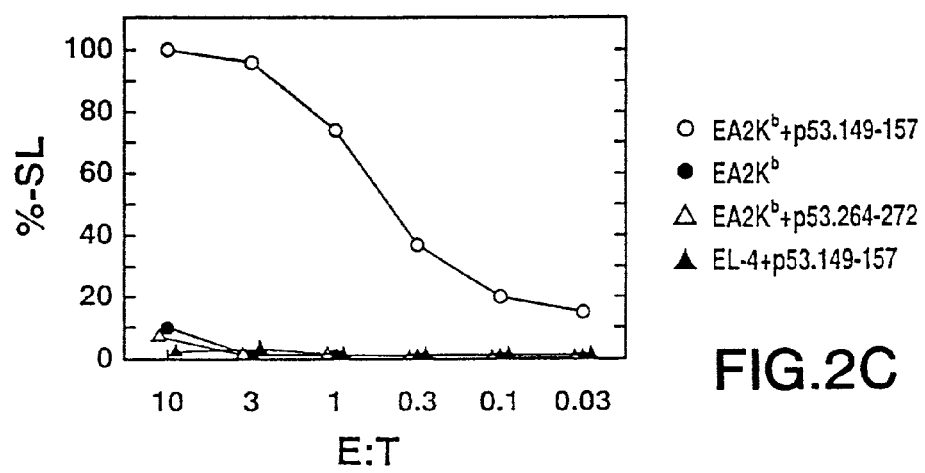
FIG. 2C illustrates lysis of target cells with CTL that were generated from transgenic mice immunized with the p53.149-157 peptide (CTL A2K$^b$ 149). The results of EA2K$^b$+p53.149-157; open circle, p53.264-272 peptide bound to A2.1/K$^b$ on the surface of the EA2K$^b$ cells (EA2K$^b$+ p53.264-272; open triangle), EA2K$^b$; closed circle, and EL-4 cells incubated in the presence of p53.149-157 cells (EL-4+ p53.149-157; closed triangle) are given.
Figure 2D:
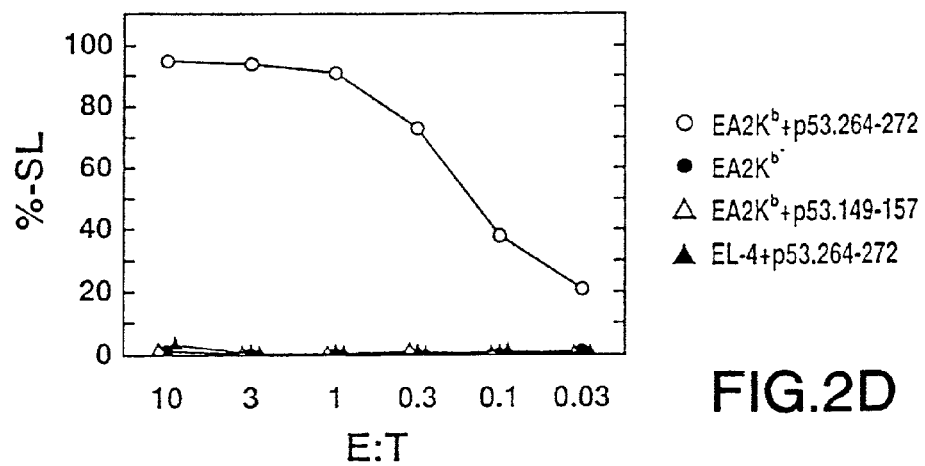
FIG. 2D illustrates lysis of target cells with CTL that were generated from transgenic mice immunized with the p53.264-272 peptide (CTL A2K$^b$ 264). The results EA2K$^b$+ p53.264-272 (open circle), EA2K$^b$+p53.149-157 (open triangle), EA2K$^b$ (closed circle), and EL-4 cells incubated in the presence of p53.264-272 cells (EL-4+p53.264-272; closed triangle) are given.

Amino Acid Residue: An amino acid, e.g., one formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.* 243:3552-59 (1969) and adopted at 37 C.F.R. § 1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. § 1.822(b)(4), and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxy-terminal group such as COOH.

The term conservative substitution as used herein is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like. The term "conservative substitution" also includes the use of a substituted amino acid in place of an unsubstituted parent amino acid provided that such a polypeptide also displays the requisite binding activity.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be a "radical replacement", as are replacements between nonionic and ionic residues, and bulky residues such as Phe, Tyr or Trp and less bulky residues such as Gly, Ile and Val.

The term antibody in its various grammatical forms is used herein to refer to immunoglobulin molecules and immunologically active portions of immunoglobulin molecules, i.e., molecules that contain an antibody combining site or paratope. Illustrative antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

The term antibody combining site refers to that structural portion of an antibody molecule comprised of a heavy and light chain variable and hypervariable regions that specifically binds (immunoreacts with) antigen.

The term correspond in its various grammatical forms is used herein and in the claims in relation to polypeptide sequences to mean the polypeptide sequence described plus or minus up to three amino acid residues at either or both of the amino-and carboxy-termini and containing only conservative substitutions in particular amino acid residues along the polypeptide sequence.

Polypeptide and Peptide are terms used interchangeably herein to designate a series of no more than about 50 amino acid residues connected one to the other by peptide bonds between the alpha-amino and carboxy groups of adjacent residues.

Protein: Protein is a term used herein to designate a series of greater than 50 amino acid residues connected one to the other as in a polypeptide.

Receptor and receptor protein are terms used herein to indicate a biologically active proteinaceous molecule that specifically binds to (or with) other molecules.

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous and are included within the scope of proteins defined by the terms "p53" and "Her-2/Neu". Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

Transfection as the term is used herein means the acquisition of new genetic markers by incorporation of added DNA in eucaryotic cells, whereas transformation refers to the acquisition of new genetic markers by incorporation of added DNA in procaryotic cells.

As used herein, the term vector refers to a DNA molecule capable of autonomous replication and to which a DNA segment, e.g., gene or polynucleotide, can be operatively linked so as to bring about replication of the attached segment.

Vectors capable of directing the expression of DNA segments (genes) encoding one or more proteins are referred to herein as "expression vectors". Also included are vectors which allow the cloning of cDNA (complementary DNA) from mRNAs produced using reverse transcriptase.

B. Detailed Description

1. Enhancing Tumor Immunogenicity Using Tumor-Specific Antigens a. The p53 Protein Normal p53 protein acts as a regulator of the cell cycle. In response to DNA damaging influences, such as UV light, normal p53 protein accumulates in cell nuclei, causing cell cycle arrest at the $G_1$ phase, thus allowing cells to repair the DNA damage. This function of p53 is lost in tumor cells in which p53 is inactivated by mutation of the gene or by binding of the proteins encoded by viral or cellular oncogenes to p53. As a result, genetic alterations accumulate at a rapid rate in affected cells, leading to malignant transformation. (See, e.g., Lane, *Nature* 358: 15-16 (1992); Ullrich, et al., *J. Biol. Chem.* 267: 15259-15262 (1992); Hartwell, *Cell* 71: 543-546 (1992).)

It is not known to what extent the overexpression of p53—the expression of which is seen as a normal response to DNA damage—leads to an immune response to the p53 protein. In any event, mutation of the p53 gene (p53) is the most frequent genetic change associated with human cancer. Moreover, in many tumor cells carrying mutations in p53, the p53 protein is also overexpressed due to decreased breakdown.

In addition, this overexpression is often associated with the formation of anti-p53 antibodies. For example, in one recent study, all small cell lung cancer patients with demonstrable serum antibodies against the p53 protein had mis-sense mutations in p53 and overexpressed p53 antigen in their tumor cell lines. One study reported that anti-p53 antibodies were not detected in sera from patients with other types of p53 mutation (Winter, et al., *Cancer Res*. 52: 4168-74 (1992)).

It has also been reported that the antibody response to p53 in breast cancer patients is directed against immunodominant epitopes unrelated to the mutational "hot spot" (Schlichtholz, et al., *Cancer Res*. 52: 6380-4 (1992)). The antibodies were reactive with two immunodominant regions located at the carboxy-and amino-termini of the protein, outside the mutational "hot spot" region (Id.).

The detection of antibodies directed against immunodominant epitopes suggests that such antibodies are actually autoantibodies, as they are directed against normal p53 sequences. In turn, this finding implies that the low level of p53 in normal cells is "ignored" by the immune system, which means that immunotherapies directed against p53 would likely cause little or no damage to normal cells.

The concept of autoimmunity to p53 as a possible therapeutic principle is also supported by the in vitro arousal of CTL responses against a wild type p53 peptide presented by the HLA A2.1 MHC class I molecule. In the relevant study, CTLs against a mutant p53 peptide presented by HLA A2.1 were also obtained.

Responses against both peptides were obtained with responding T lymphocytes from healthy donors. The extent to which these CTLs can recognize HLA-matched tumor cells with p53 overexpression mutants was not tested, however. Interestingly, no CTLs were obtained by stimulation with a p53 self-peptide that binds HLA A2.1 with even higher affinity, suggesting that this peptide may have induced immunological tolerance. (See Melief and Kast, *Curr. Op. Immunol.* 5: 709-13 (1993)).

b. Her-2/Neu

Her-2/Neu, which is also known as c-erbB-2, is a proto-oncogene that encodes a 185 kDa transmembrane receptor glycoprotein with tyrosine-specific kinase activity. Expression of this protein is enhanced in a number of breast and ovarian tumors and correlates with tumor aggressiveness, suggesting that it may play an important role in tumor growth. (See, e.g., Ioannides, et al., *Cellular Immunol.* 151: 225-234 (1993).) The Her-2/Neu protein has also been described as a growth factor receptor-like protein. (See, e.g., DiFiore, et al., *Science* 237: 178-182 (1987); Bargmann, et al., *Nature* 319: 226-230 (1986); Yamamoto, et al., *Nature* 319: 230-234 (1986).)

Her-2/Neu is similar in structure and sequence to the epidermal growth factor receptor (Coussens, et al., *Science* 230: 1132 (1985)). The Her-2/neu oncogene (also referred to as erbB-2) is amplified and overexpressed in approximately 30% of human breast and ovarian tumors, and the overexpression of the Her-2/Neu protein correlates with a poor prognosis in these diseases (Slamon, et al., *Science* 244: 707 (1989)).

Recent in vitro experiments submit that at least three antigenic epitopes are recognized on ovarian cancer cells by tumor-specific CTL (Ioannides, et al., *J. Immunol*. 146: 1700 (1991)). Another study has proposed that the sensitivity of ovarian epithelial tumor cells to CTL-mediated lysis is associated with the level of expression of Her-2/Neu, intimating that this oncogene product may serve as a source of tumor-associated antigens or as an inducer of such peptides (Yoshino, et al., *J. Immunol*. 152: 2393 (1994)). The identity or source of these tumor-associated antigens (TAA) is unknown, but the oncogene products seem to be logical candidates. The potential relationship between Her-2/Neu expression and the immune response to ovarian cancer is unclear, however, but it has been proposed that Her-2/Neu expression may be inversely related to lymphokine-activated killer cell-mediated killing (Lichtenstein, et al., *Cancer Res*, 50: 7364 (1990)).

Another study proposes that CTL expanded from tumor-associated lymphocytes with HLA-A2$^+$ and Her-2/Neu$^+$ tumors can specifically recognize synthetic peptides corresponding to amino acids 971-980 of Her-2/Neu protein (Ioannides, et al., *Cellular Immunol*. 151: 225-234 (1993)).

2. Polypeptides

A polypeptide or peptide of the present invention is preferably derived from a protein expressed by a "target" cell or tissue—e.g., tumor cells or other malignant cells or tissues. In one embodiment, such a protein from which useful peptides may be derived is unique to target cells or tissues. Alternatively, an exemplary peptide may be derived from a protein which is expressed in "normal" cells, but is overexpressed in "abnormal" cells such as tumor cells.

For example, a polypeptide of the present invention may be derived from p53 protein, Her-2/Neu protein, or from other candidate (i.e., tumor-associated) proteins. The terms "polypeptide" and "peptide" may be used interchangeably herein.

Thus, an exemplary polypeptide of the present preferably invention corresponds in amino acid residue sequence to one or more amino acid residue sequences of a normal p53 protein, a mutated form of p53 protein, a p53 protein analogue, or a derivative of any of the foregoing. For example, a p53-derived polypeptide may have an amino acid residue sequence corresponding to the formula STPPPGTRV (SEQ ID NO 3), or a sequential subset thereof.

Another exemplary polypeptide of the present invention corresponds in amino acid residue sequence to one or more amino acid residue sequences of normal Her-2/Neu protein, a mutated form of Her-2/Neu protein, a Her-2/Neu protein analogue, or a derivative of any of the foregoing. For example, a Her-2/Neu-derived polypeptide may have an amino acid residue sequence corresponding to the formula KIFGSLAFL (SEQ ID NO 10), VMAGVGSPYV (SEQ ID NO 12), or any sequential subsets thereof.

A polypeptide of the present invention also can exhibit homology in sequence to a polypeptide portion of a protein expressed or abnormally expressed in a target cell or tissue. Preferably, a polypeptide of the present invention corresponds to a sequential subset of p53 protein or Her-2/Neu protein, wherein "sequential subset" refers to the fact that a polypeptide has an amino acid residue sequence corresponding to that of a subset of the amino acid residue sequence of a larger protein or polypeptide. For example, if "ABCDEFGH"

represented an amino acid residue sequence of a polypeptide, exemplary sequential subsets thereof would include "ABC", "BCDE", "DEFGH", "ABCDEFG", and so forth.

The present invention provides certain polypeptides that stimulate HLA class I restricted cytotoxic T lymphocyte ("CTL") responses against certain tumor antigens, particularly when such antigens are expressed in a host cell that is capable of expressing such antigens. Such polypeptides are useful in compositions and methods for the treatment, prevention, and diagnosis of tumors and malignancies—e.g., carcinoma of the breast. For example, stimulated CTLs of the present invention are able to specifically target and kill specific antigen-expressing cells, thereby preventing, impeding, or reversing the course of the relevant disease process. Novel combinations of epitopes are contemplated within the context of the present invention, such that the CTL response described in brief above, and in greater detail below, is combined with a T-helper response or multiple CTL response directed at different antigens, for example.

The polypeptides of interest are derived from various regions of tumor-related proteins or nucleotide sequences encoding same. For example, p53 peptides having the following amino acid residue sequences (or sequential subsets thereof) are contemplated herein: p53.25-35, LLPENNVLSPL (SEQ ID NO 1); p53.65-73, RMPEAAPPV (SEQ ID NO 2); p53.149-157, STPPPGTRV (SEQ ID NO 3); p53.264-272, LLGRNSFEV (SEQ ID NO 4). In addition, Her-2/Neu peptides having the following amino acid residue sequences (or sequential subsets thereof) are also contemplated herein: HER-3, KIFGSLAFL (SEQ ID NO 10); HER-6, TLQGLGISWL (SEQ ID NO 11); HER-7, VMAGVGSPYV (SEQ ID NO 12); HER-8, VLQGLPREYV (SEQ ID NO 13); and HER-9, ILLVVVLGV (SEQ ID NO 14).

In certain embodiments of the present invention, the polypeptides of interest will have the sequences just recited as well as others listed below, or will have sequences that are substantially homologous thereto. Two polypeptides are said to be substantially homologous if at least 50% of the amino acid ("aa") residues are the same in the same or analogous position. By analogous position, it is intended the relative position of the polypeptide of interest itself, regardless of any flanking polypeptide or other chemical elements that may be attached to the polypeptide of interest.

Preferred peptides employed in the subject invention, accordingly, need not be identical, but are at least substantially homologous, to the following peptides: LLPENNVLSPL (SEQ ID NO 1); RMPEAAPPV (SEQ ID NO 2); STPPPGTRV (SEQ ID NO 3); LLGRNSFEV (SEQ ID NO 4); KIFGSLAFL (SEQ ID NO 10); TLQGLGISWL (SEQ ID NO 11); VMAGVGSPYV (SEQ ID NO 12); VLQGLPREYV (SEQ ID NO 13); and ILLVVVLGV (SEQ ID NO 14).

The present invention relates to a polypeptide having substantial homology with a CTL epitope selected from the same group of polypeptides identified above. Preferred polypeptides include LLPENNVLSPL (SEQ ID NO 1); RMPEAAPPV (SEQ ID NO 2); STPPPGTRV (SEQ ID NO 3); LLGRNSFEV (SEQ ID NO 4); KIFGSLAFL (SEQ ID NO 10); TLQGLGISWL (SEQ ID NO 11); VMAGVGSPYV (SEQ ID NO 12); VLQGLPREYV (SEQ ID NO 13); and ILLVVVLGV (SEQ ID NO 14).

In particular, the present invention relates to a suitable molecule comprising a polypeptide having substantial homology with one of the CTL epitopes recited above. The molecule of the present invention comprises at least about five amino acids and as many as about 50 amino acids. A preferred range of amino acids for the molecule of the present invention is from about seven amino acids to fewer than about twenty-five amino acids. A more preferred range of amino acids is from about eight amino acids to fewer than about fifteen. An even more preferred range of amino acids is from about eight amino acids to fewer than about 13 amino acids.

It may be desirable to optimize peptides of the invention to a length of about eight to twelve amino acid residues, commensurate in size with endogenously processed peptides that are bound to major histocompatibility complex ("MHC") class I molecules on the cell surface. See generally, Schumacher et al., *Nature*, 350, 703-706 (1991); Van Bleek et al., *Nature*, 348, 213-216 (1990); Rotzschke et al., *Nature*, 348, 252-254 (1990); and Falk et al., *Nature*, 351, 290-296 (1991). Methods of selecting and generating class I MHC molecules are also disclosed in U.S. Pat. No. 5,314,813, the disclosures of which are incorporated by reference herein.

As set forth in more detail below, usually the peptides will have at least a majority of amino acids that are homologous to a corresponding portion of contiguous residues of the p53 or Her-2/Neu sequences disclosed hereinabove, and contain a CTL-inducing epitope.

The peptides of the present invention can be prepared by any suitable means, such as synthetically using standard peptide synthesis chemistry or by using recombinant DNA technology. Although the peptide preferably will be substantially free of other naturally occurring p53 or Her-2/Neu proteins and fragments thereof, in some embodiments the peptides can be synthetically conjugated to native fragments or particles, or other compounds that are nonproteinaceous. The term peptide is used interchangeably with polypeptide or oligopeptide in the present specification to designate a series of amino acids connected one to the other by peptide bonds between the alpha-amino and alpha-carboxy groups of adjacent amino acids. The polypeptides or peptides can be any suitable length, either in their neutral (actually zwitterionic) forms or in forms that are salts, and either free of modifications, such as glycosylation, side chain oxidation, or phosphorylation, or containing these modifications, subject to the condition that the modification not destroy the biological activity of the polypeptides, as herein described.

Desirably, the peptide will be as small as possible while still maintaining substantially all of the biological activity of the larger peptides first disclosed herein. By biological activity is meant the ability to bind an appropriate MHC molecule and induce a cytotoxic T lymphocyte response against p53 or Her-2/Neu antigen or antigen mimetic. By a cytotoxic T lymphocyte response is meant a $CD8^+$ T lymphocyte response specific for an antigen of interest, wherein CD8+, MHC class I-restricted T lymphocytes are activated. The activated T lymphocytes secrete lymphokines (e.g., gamma interferon) and liberate other products (e.g., serine esterases) that inhibit viral replication in infected autologous cells or transfected cells, with or without cell killing.

Various modifications can be effected at noncritical amino acid positions within the polypeptide of interest without substantially disturbing its biological activity. Such modifications include, but are not limited to, substitutions, deletions and additions of other peptidyl residues, $C_1$-$C_7$ alkyl or $C_1$-$C_{10}$ aralkyl, as described herein and as appreciated in the art.

A polypeptide of the present invention may or may not be glycosylated, depending on the means of synthesis. For example, if a non-glycosylated polypeptide is preferred, it may be synthesized either directly by standard peptide synthesis techniques or by procaryotic host expression of a recombinant DNA molecule of the present invention. A eucaryotically produced polypeptide of the present invention is not typically glycosylated.

A polypeptide of the present invention can also incorporate a variety of changes, such as insertions, deletions, and substitutions of amino acid residues which are either conservative or nonconservative as long as the resulting polypeptide molecule exhibits the desired properties. The "desired properties" as referred to herein include that the polypeptide is immunogenic in a suitable host and able to generate antibodies to a desired protein, polypeptides derived therefrom, or proteins or polypeptides substantially homologous to the desired protein, whether it is present in the denatured state (as is found in an SDS-PAGE gel) or in its natural state, as expressed in or on cells. In various alternative embodiments, the desired protein may be p53, Her-2/Neu, or another protein associated with tumors or other malignancies.

A majority of the amino acids of the polypeptides of the present invention will be identical or substantially homologous to the amino acids of the corresponding portions of naturally occurring p53 or Her-2/Neu proteins or epitopes identified above, wherein the selected polypeptide can be flanked and/or modified at one or both termini as described herein.

Accordingly, a molecule of the present invention in one of its embodiments comprises a polypeptide as described hereinabove that has conjugated thereto a substance, wherein the substance is selected from the group consisting of a radiolabel, an enzyme, a fluorescent label, a solid matrix, a carrier, and a second CTL epitope. The substance can be conjugated to the polypeptide at any suitable position, including the N and C termini and points in between, depending on the availability of appropriate reactive groups in the side chains of the constituent amino acids of the polypeptide of interest. Additionally, the substance can be conjugated directly to the polypeptide or indirectly by way of a linker. Preferred radiolabels include $^3H$, $^{14}C$, $^{32}P$, $^{35}S$, $^{125}I$, and other suitable radiolabels for use in various radioimmunoassays and the like. Preferred fluorescent labels include fluorescein, rhodamine, and other suitable fluorescent labels for use in fluorescent assays and the like.

Preferred enzymes include alkaline phosphatase and other suitable enzymes useful for any suitable purpose, including as a marker in an assay procedure. Preferred solid matrices are glass, plastic, or other suitable surfaces, including various resins such as Sephadex® chromatography media and the like. Preferred carriers include immunogenic lipids, proteins, and other suitable compounds, such as a liposome or bovine serum albumin. Preferred second CTL epitopes include T-helper specific antigens, antigens that would foster a B cell response, and other suitable antigens that stimulate CTLs.

Additional amino acids can be added to the termini of a peptide of the present invention to provide for ease of linking peptides one to another, for coupling to a carrier, support or a larger peptide, for reasons discussed herein, or for modifying the physical or chemical properties of the peptide, and the like. Suitable amino acids, such as tyrosine, cysteine, lysine, glutamic or aspartic acid, and the like, can be introduced at the C-or N-terminus of the peptide. In addition, a peptide of the present invention can differ from the natural sequence by being modified by terminal-$NH_2$ acylation, e.g., acetylation, or thioglycolic acid amidation, terminal-carboxy amidation, e.g., ammonia, methylamine, etc. In some instances these modifications may provide sites for linking to a support or other molecule, thereby providing a linker function.

It is understood that the p53 or Her-2/Neu peptides of the present invention or analogs or homologs thereof that have cytotoxic T lymphocyte stimulating activity may be modified as necessary to provide certain other desired attributes—e.g., improved pharmacological characteristics—while increasing or at least substantially retaining the biological activity of the unmodified peptide. For instance, the within-described peptides can be modified by extending, decreasing or substituting amino acids in the peptide sequence by, for example, the addition or deletion of suitable amino acids on either the amino terminal or carboxy terminal end, or both, of peptides derived from the sequences disclosed herein.

When a polypeptide of the present invention incorporates conservative substitutions of the sequences corresponding to the p53 or Her-2/Neu proteins or polypeptides depicted above, the substituted amino acid residues are replaced by another, biologically similar amino acid residue such that the resulting polypeptide has an amino acid residue sequence that is different from (other than) a sequence of p53 or Her-2/Neu. Some examples of conservative substitutions include substitution of a hydrophobic residue such as isoleucine, valine, leucine or methionine for another hydrophobic residue. Also, a polar residue such as arginine, glycine, glutamic acid, aspartic acid, glutamine, asparagine, and the like, can be conservatively substituted for another member of this group.

Still another aspect of a polypeptide incorporating conservative substitutions occurs when a substituted amino acid residue replaces an unsubstituted parent amino acid residue. Examples of substituted amino acids may be found at 37 C.F.R. § 1.822(b)(4), which species are incorporated herein by reference.

The peptides may be modified to enhance substantially the CTL inducing activity, such that the modified peptide analogs have CTL activity greater than a peptide of the wild-type sequence. For example, it may be desirable to increase the hydrophobicity of the N-terminus of a peptide, particularly where the second residue of the N-terminus is hydrophobic and is implicated in binding to the HLA restriction molecule. By increasing hydrophobicity at the N-terminus, the efficiency of the presentation to T cells may be increased. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

Therefore, peptides of the present invention may be subject to various modifications, such as insertions, deletions, and substitutions, either conservative or non-conservative, where such modifications provide for certain advantages in their use. By "conservative substitution" is meant replacing an amino acid residue with another that is biologically and/or chemically similar, e.g., one hydrophobic residue for another, or one polar residue for another. The substitutions include combinations such as Gly, Ala; Val, Ile, Leu; Asp, Glu; Asn, Gin; Ser, Thr; Lys, Arg; and Phe, Tyr. Preferably, the portion of the sequence that is intended to mimic substantially a p53 or Her-2/Neu cytotoxic T lymphocyte-stimulating epitope will not differ by more than about 20% from the sequence of at least one portion or segment of p53 protein or Her-2/Neu protein, except where additional amino acids may be added at either terminus for the purpose of modifying the physical or chemical properties of the peptide for, for example, ease of linking or coupling, and the like.

Within the peptide sequences identified by the present invention, including the representative peptides listed above, there are residues (or those that are substantially functionally equivalent) that allow a particular peptide to retain its biological activity, i.e., the ability to stimulate a class I-restricted cytotoxic T-lymphocytic response against cells that express p53 or Her-2/Neu antigen. These residues can be identified by suitable single amino acid substitutions, deletions, or insertions, followed by suitable assays, such as testing for cytotoxic activity by so-stimulated CTLs.

In addition, the contributions made by the side chains of the residues can be probed via a systematic replacement of individual residues with a suitable amino acid, such as Gly or Ala. Systematic methods for determining which residues of a linear amino acid sequence are required for binding to a specific MHC protein, one of the characteristics of the peptides of the present invention, are known. See, for instance, Allen et al., Nature 327: 713-717; Sette et al., Nature 328: 395-399; Takahashi et al., J. Exp. Med. 170: 2023-2035 (1989); and Maryanski et al., Cell 60: 63-72 (1990).

Peptides that tolerate multiple amino acid substitutions generally incorporate small, relatively neutral molecules, e.g., Ala, Gly, Pro, or similar residues. The number and types of residues that can be substituted, added or subtracted will depend on the spacing necessary between the essential epitopic points and certain conformational and functional attributes that are sought. By types of residues, it is intended, e.g., to distinguish between hydrophobic and hydrophilic residues, among other attributes. If desired, increased binding affinity of peptide analogs to its MHC molecule for presentation to a cytotoxic T-lymphocyte can also be achieved by such alterations. Generally, any spacer substitutions, additions or deletions between epitopic and/or conformationally important residues will employ amino acids or moieties chosen to avoid stearic and charge interference that might disrupt binding.

Peptides that tolerate multiple substitutions while retaining the desired biological activity may also be synthesized as D-amino acid-containing peptides. Such peptides may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the present invention provides methods for identifying other epitopic regions associated with said peptide regions capable of inducing MHC-restricted cytotoxic T lymphocyte responses against tumor cells or tissues. The methods comprise obtaining peripheral blood lymphocytes (PBL) from affected and/or unaffected individuals and exposing (i.e., stimulating) the PBL cells with synthetic peptide or polypeptide fragments derived from a peptide region (e.g., p53 derivatives such as p53.25-35, LLPENNVLSPL (SEQ ID NO 1); p53.65-73, RMPEAAPPV (SEQ ID NO 2); p53.149-157, STPPPGTRV (SEQ ID NO 3); and p53.264-272, LLGRNSFEV (SEQ ID NO 4)). Peptides derived from Her-2/Neu proteins are useful in this regard as well, and include exemplary peptides such as HER-3, KIFGSLAFL (SEQ ID NO 10); HER-6, TLQGLGISWL (SEQ ID NO 11); HER-7, VMAGVGSPYV (SEQ ID NO 12); HER-8, VLQGLPREYV (SEQ ID NO 13); and HER-9, ILLVVVLGV (SEQ ID NO 14).

Pools of overlapping synthetic peptides randomly selected from the p53 or Her-2/Neu protein's amino acid residue sequence, each typically about 8 to 20 residues long, preferably 8-12 residues, can be used to stimulate the cells. Alternatively, as exemplified hereinbelow, peptides fitting a binding motif for CTL-directed antigens of a particular HLA class I allele (Falk et al., Nature 351: 290-296 (1991)) were selected for testing. It is contemplated that peptides fitting the analogous binding motifs for other HLA class I alleles may be identified by following the methods disclosed herein, and accordingly are viewed as part of the present invention. (See, e.g., Guo et al., Nature 360: 364-366 (1992); Jardetzky et al., Nature 353: 326-329 (1991).)

Active peptides can be selected from pools that induce cytotoxic T lymphocyte activity. The ability of the peptides to induce specific cytotoxic activity is determined by incubating the stimulated PBL cells with autologous labeled (e.g., $^{51}$Cr) target cells (such as HLA matched macrophages, T cells, fibroblasts or B lymphoblastoid cells) expressing p53 or Her-2/Neu proteins, polypeptides, or derivatives thereof (or subgenomic fragments thereof), such that the targeted antigen is synthesized endogenously by the cell (or the cell is pulsed with the peptide of interest), and measuring specific release of label.

Once a peptide having an epitopic region that stimulates a cytotoxic T lymphocyte response is identified, the MHC restriction element of the response can be determined and/or confirmed. This involves incubating the stimulated PBL or short term lines thereof with a panel of (labeled) target cells or known HLA types that have been pulsed with the peptide of interest, or appropriate controls. The HLA allele(s) of cells in the panel that are lysed by the CTL are compared to cells not lysed, and the HLA restriction element(s) for the cytotoxic T lymphocyte response to the antigen of interest is identified.

Carbone et al. (J. Expo. Med. 167: 1767 (1988)) have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native Her-2/Neu proteins, for example, would be undesirable in the development of anti-Her-2/Neu peptide therapeutics and vaccine compositions, methods to circumvent this potential limitation are preferably used. For example, a sequential restimulation of cytotoxic T cells may be employed according to the present invention to identify and select T cells with a higher affinity for naturally processed antigen than for a synthetic peptide. Short term cytotoxic T lymphocyte lines are established by restimulating activated PBL.

Cells stimulated with peptide are preferably restimulated with peptide and recombinant or native p53 or Her-2/Neu antigen, e.g., a Her-2/Neu-derived peptide. Cells having activity may also be stimulated with an appropriate T cell mitogen, e.g., phytohemagglutinin (PHA). The restimulated cells are provided with irradiated allogeneic PBLs as an antigen nonspecific source of T cell help, and the appropriate antigen.

To expand selectively the population of cytotoxic T lymphocytes that recognize, e.g., native Her-2/Neu antigen and to establish long term lines, a sample of PBL from a patient is first stimulated with peptide and recombinant or native tumor-related antigen, followed by restimulation with HLA-matched B lymphoblastoid cells that stably express the corresponding tumor-related antigen polypeptide. The cell lines are re-confirmed for the ability to recognize endogenously synthesized antigen using autologous and allogeneic B-lymphoblastoid or other cells transfected or infected so as to produce the appropriate antigen.

Having identified different peptides of the invention that contribute to inducing anti-tumor cytotoxic T lymphocyte responses in one or more patients or HLA types, in some instances it may be desirable to join two or more peptides in a composition, either by chemical linkage or as a physical mixture. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g. p53-derived peptides STPPPGTRV (SEQ ID NO 3) and LLGRNSFEV (SEQ ID NO 4), which peptides can be combined in a "cocktail" to provide enhanced immunogenicity for cytotoxic T lymphocyte responses. Moreover, suitable peptides of one p53 or Her-2/Neu region can be combined with suitable peptides of other p53 or Her-2/Neu regions, respectively, from the same or different protein, particularly when a second or subsequent peptide has a MHC restriction element different from the first. The present disclosure thus includes exemplary proteins, polypeptides, and epitope sequences derived from various p53 or Her-2/Neu regions.

This composition of peptides can be used effectively to broaden the immunological coverage provided by therapeutic, prophylactic, or diagnostic methods and compositions of the present invention for the benefit of a diverse population. For example, the different frequencies of HLA alleles among prevalent ethnic groups (Caucasian, asian and african blacks) are shown in the following table. Therapeutic or vaccine compositions of the invention may be formulated to provide potential therapy or immunity to as high a percentage of a population as possible.

HLA ALLELE FREQUENCIES AMONG PREVALENT ETHNIC GROUPS

| HLA Allele | EUC | NAC | AFR | JPN |
|---|---|---|---|---|
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28[1] | 7.7 | 9.9 | 16.6 | 1.1 |

Abbreviations: EUC, European Caucasian; NAC, North American Caucasian; AFR, African blacks; JPN, Japanese.
[1]A28 represents the two alleles A268 and A269.

The peptides of the present invention may further be combined via linkage to form polymers (multimers), or can be formulated in a composition without linkage, as an admixture. Where the same peptide is linked to itself, thereby forming a homopolymer, a plurality of repeating epitopic units are presented. When the peptides differ, heteropolymers with repeating units are provided, forming a cocktail of, for example, epitopes specific to different tumor antigen segments, different epitopes to the same protein or gene region, different epitopes to different proteins or gene regions, different HLA restriction specificities, and/or a peptide that contains T helper epitopes. In addition to covalent linkages, non-covalent linkages capable of forming intermolecular and intrastructural bonds are included.

Linkages for homo- or hetero-polymers or for coupling to carriers can be provided in a variety of ways. For example, cysteine residues can be added at both the amino-and carboxy-termini, where the peptides are covalently bonded via controlled oxidation of the cysteine residues. Also useful are a large number of heterobifunctional agents that generate a disulfide link at one functional group end and a peptide link at the other, including N-succinimidyl-3-(2-pyridyl-dithio) proprionate (SPDP). This latter reagent creates a disulfide linkage between itself and a cysteine residue in one protein and an amide linkage through the amino on a lysine or other free amino group in the other. A variety of such disulfide/amide forming agents are known. See, for example, *Immun. Rev.* 62: 185 (1982).

Other bifunctional coupling agents form a thioether rather than a disulfide linkage. Many of these thioether forming agents are commercially available (from, for example, Aldrich Chemical Company, Inc., Milwaukee, Wis.) and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl-4-(n-maleimidomethyl)cyclohexane-1-carboxylate (SMCC). It will be understood that suitable linkage does not substantially interfere with either of the linked groups to function as described, e.g., as an anti-tumor cytotoxic T cell determinant/stimulant, peptide analogs, or T helper determinant/stimulant.

In another aspect of the present invention, the peptides of the invention can be combined or coupled with other suitable peptides that present anti-tumor T-helper cell epitopes, i.e., epitopes that stimulate T cells that cooperate in the induction of cytotoxic T cells to tumor antigens, such as those derived from p53 or Her-2/Neu protein. The T-helper cells can be either the T-helper 1 or T-helper 2 phenotype, for example.

The peptides of the present invention can be prepared using any suitable means. Because of their relatively short size (generally, fewer than 50 amino acids, and preferably fewer than 20), the peptides can be synthesized in solution or on a solid support in accordance with conventional peptide synthesis techniques. Various automatic synthesizers are commercially available (for example, from Applied Biosystems) and can be used in accordance with known protocols. See, for example, Stewart and Young, *Solid Phase Peptide Synthesis* (2d. ed., Pierce Chemical Co., 1984); Tam et al., *J. Am. Chem. Soc.* 105: 6442 (1983); Merrifield, *Science* 232: 341-347 (1986); and Barany and Merrifield, *The Peptides* (Gross and Meienhofer, eds., Academic Press, New York, 1979), 1-284.

Alternatively, suitable recombinant DNA technology may be employed for the preparation of the peptides of the present invention, wherein a nucleotide sequence that encodes a peptide of interest is inserted into an expression vector, transformed or transfected into a suitable host cell and cultivated under conditions suitable for expression. These procedures are generally known in the art, as described generally in Sambrook et al., *Molecular Cloning, A Laboratory Manual* (2d ed., Cold Spring Harbor Press, Cold Spring Harbor, New York, 1989), and *Current Protocols in Molecular Biology* (Ausubel et al., eds., John Wiley and Sons, Inc., New York, 1991), and U.S. Pat. Nos. 4,237,224, 4,273,875, 4,431,739, 4,363,877 and 4,428,941, for example.

Thus, recombinant DNA-derived proteins or peptides, which comprise one or more peptide sequences of the invention, can be used to prepare the anti-tumor cytotoxic T cell epitopes identified herein or identified using the methods disclosed herein. For example, a recombinant p53-derived peptide of the present invention may be prepared in which the p53 amino acid sequence is altered so as to present more effectively epitopes of peptide regions described herein to stimulate a cytotoxic T lymphocyte response. By this means, a polypeptide is used that incorporates several T cell epitopes into a single polypeptide.

As the coding sequence for peptides of the length contemplated herein can be synthesized by chemical techniques, for example, the phosphotriester method of Matteucci et al., *J. Am. Chem. Soc.*, 103, 3185 (1981), modifications can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available.

For expression of fusion proteins, the coding sequence will be provided with operably linked start and stop codons, promoter and terminator regions and usually a replication system to provide an expression vector for expression in a suitable cellular host. For example, promoter sequences compatible with bacterial hosts are provided in plasmids containing convenient restriction sites for insertion of the desired coding sequence. The resulting expression vectors are transformed into suitable bacterial hosts, yeast or mammalian cell hosts may also be used, employing suitable vectors and control sequences.

It is also preferable that the polypeptide is antigenic when expressed on cells or in its denatured state so that antibodies immunoreactive with the desired protein molecule also immunoreact with a polypeptide of the present invention. Accordingly, a polypeptide of the present invention can also be used to generate a variety of useful antibodies by means described herein. A polypeptide of the present invention may also be used to specifically trigger an immune response—e.g., to generate specific cytotoxic T lymphocytes (CTLs). These and other utilities of the polypeptides will be apparent from the discussions provided hereinbelow.

A polypeptide of the present invention can be synthesized by any of the peptide synthetic techniques known to those skilled in the art. A summary of some of the techniques available can be found in J. M. Stuard and J. D. Young, "Solid Phase Peptide Synthesis", W. H. Freeman, Co., San Francisco (1969), J. Meinhofer, "Hormonal Proteins and Peptides" Vol. 2, pp. 46, Academic Press (New York) 1983, and U.S. Pat. No. 4,631,211, which description is incorporated herein by reference. When a polypeptide desired for use in the present invention is relatively short (less than about 50 amino acid residues in length) direct peptide synthetic techniques are generally favored, usually by employing a solid phase technique such as that of Merrifield (*JACS* 85: 2149 (1963)).

A polypeptide of the present invention can also be synthesized by recombinant DNA techniques. Such recombinant techniques are favored especially when the desired polypeptide is relatively long (greater than about 50 amino acids residues in length). When recombinant DNA techniques are employed to prepare a polypeptide of the present invention, a DNA segment coding for the desired polypeptide is incorporated into a preselected vector that is subsequently expressed in a suitable host. The expressed polypeptide, containing at least one of the amino acid residue sequences corresponding to p53 or Her-2/Neu proteins or polypeptides identified above, is preferably purified by a routine method such as gel electrophoresis, immunosorbent chromatography, and the like.

3. Hybridomas and Antibody Compositions a. Hybridomas

Hybridomas of the present invention are those which are characterized as having the capacity to produce an antibody, including a monoclonal antibody, of the present invention. Methods for producing hybridomas producing (secreting) antibody molecules having a desired immunospecificity, i.e., having the ability to immunoreact with a particular protein, an identifiable epitope on a particular protein and/or a polypeptide, are generally well known in the art. For example, useful methods are described by Niman et al., *PNAS USA* 80: 4949-4953 (1983), and by Galfre et al., *Meth. Enzymol.* 73: 3-46 (1981). Other methods are described in U.S. Pat. Nos. 5,180,806, 5,114,842, 5,204,445, and RE 32,011, the disclosures of which are incorporated by reference herein.

A hybridoma cell is typically formed by fusing an antibody-producing cell and a myeloma or other self-perpetuating cell line. Such a procedure was described by Kohler and Milstein, *Nature* 256: 495-497 (1975).

Typically, hybridomas of the present invention are produced by using, in the above techniques as an immunogen, a substantially pure p53 or Her-2/Neu protein, polypeptide, homolog, or a sequential subset of a polypeptide of the present invention.

b. Inocula

In another embodiment, a protein or polypeptide of this invention, an antigenicaily related variant thereof, or a protein or polypeptide at least 75% homologous to at least a portion of a p53 or Her-2/Neu protein or polypeptide identified herein is used in a pharmaceutically acceptable aqueous diluent composition to form an inoculum that, when administered in an effective amount, is capable of inducing antibodies that immunoreact with a p53 or Her-2/Neu protein or polypeptide.

The word "inoculum" in its various grammatical forms is used herein to describe a composition containing a p53 or Her-2/Neu protein or polypeptide of this invention as an active ingredient used for the preparation of antibodies against a p53 or Her-2/Neu protein or polypeptide.

When a polypeptide is used to induce antibodies it is to be understood that the polypeptide can be used alone, or linked to a carrier as a conjugate, or as a polypeptide polymer, but for ease of expression, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As previously noted, one or more additional amino acid residues can be added to the amino-or carboxy-termini of the polypeptide to assist in binding the polypeptide to a carrier. Cysteine residues added at the amino-or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.* 147: 318-326 (1983) and the like, or the use of carbodiimide technology as in the use of a water-soluble carbodiimide to form amide links to the carrier. For a review of protein conjugation or coupling through activated functional groups, see Auramcas, et al., *Scand. J. Immunol.* 8 (*Suppl.* 7): 7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, and cholera toxoid, as well as polyamino acids such as poly (D-lysine: D-glutamic acid), and the like.

The choice of carrier is more dependent upon the ultimate use of the inoculum and is based upon various criteria. For example, a carrier that does not generate an untoward reaction in the particular animal to be inoculated should be selected.

The present inoculum contains an effective, immunogenic amount of a p53 or Her-2/Neu protein or polypeptide of this invention. As noted above, a smaller polypeptide may be used as a conjugate (i.e., linked to a carrier). The effective amount of polypeptide or protein per unit dose depends, among other things, on the species of animal inoculated, the body weight of the animal, and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "dose" or "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared by dispersing a polypeptide, polypeptide-conjugate, or protein in a physiologically tolerable (acceptable) diluent or vehicle such as water, saline or phosphate-buffered saline to form an aqueous composition. For example, inocula containing p53 or Her-2/Neu peptide(s) may be prepared from substantially pure p53 or Her-2/Neu protein, respectively, by dispersion in the same physiologically tolerable diluents. Such diluents are well known in the art and are discussed, for example, in *Remington's Pharmaceutical Sciences*, 16th Ed., Mack Publishing Company, Easton, Pa. (1980) at pages 1465-1467.

Inocula may also include an adjuvant as a component of the diluent.

Adjuvants such as complete Freund's adjuvant (CFA), incomplete Freund's adjuvant (IFA) and alum are materials well known in the art, and are available commercially from several sources.

c. Antibodies and Compositions

Also contemplated within the present invention is an antibody composition that immunoreacts with an instant protein or polypeptide. An antibody composition immunoreacts with the protein or polypeptide either associated with cellular surfaces or free from cellular structures. Thus, an antibody composition binds to one or more epitopes presented by the protein or polypeptide on the exterior surface of cells or to the epitopes of cell-free polypeptides or proteins.

A preferred antibody composition of the invention immunoreacts with a p53 or Her-2/Neu protein or polypeptide molecule, preferably one presented on the cell surface. Preferred antibody compositions in this regard are monoclonal antibodies (mAbs), although polyclonal antibodies are also preferred.

Briefly, a preferred antibody composition is generated by immunizing mice with a protein or polypeptide of this invention. The antibodies generated are screened for binding affinity for a polypeptide of the instant invention, such as the p53 or Her-2/Neu polypeptides disclosed herein. The presently-disclosed polypeptides and proteins can also be used for screening the antibodies. The within-disclosed antibodies are expected to immunoreact with both sequential subsets of the relevant protein as well as with the complete protein itself.

A preferred antibody composition as contemplated herein is typically produced by immunizing a mammal with an inoculum containing human p53 protein, Her-2/Neu protein, or a polypeptide of the present invention, thereby inducing in the mammal antibody molecules having the appropriate immunospecificity for the immunogenic polypeptide. The antibody molecules are then collected from the mammal, screened and purified to the extent desired using well known techniques such as, for example, immunoaffinity purification using the immunogen immobilized on a solid support. The antibody composition so produced can be used, inter alia, in the diagnostic methods and systems of the present invention to detect expression of the instant polypeptides on the surface of cells, e.g., tumor cells in patients with small cell lung cancer.

A monoclonal antibody composition (mAb) is also contemplated by the present invention, as noted before. The phrase "monoclonal antibody composition" in its various grammatical forms refers to a population of antibody molecules that contain only one species of antibody combining site capable of immunoreacting with a particular antigen. The instant mAb composition thus typically displays a single binding affinity for any antigen with which it immunoreacts. However, a given monoclonal antibody composition may contain antibody molecules having two different antibody combining sites, each immunospecific for a different antigenic determinant, i.e., a bispecific monoclonal antibody. One preferred antibody composition of the present invention is typically composed of antibodies produced by clones of a single cell (i.e., a hybridoma) that secretes (produces) one kind of antibody molecule.

The present invention contemplates a method of forming a monoclonal antibody molecule that immunoreacts with a tumor-associated (e.g., p53 or Her-2/ Neu) protein or polypeptide of the present invention. The method comprises the steps of:

(a) Immunizing an animal with a tumor-associated protein or polypeptide of this invention or a protein homologous thereto. Use of at least a portion (e.g., a sequential subset) of tumor-associated protein as the immunogen is preferred. The immunogen may be a protein taken directly from a subject animal species. However, the antigen can also be linked to a carrier protein such as keyhole limpet hemocyanin, particularly when the antigen is small, such as a polypeptide consisting essentially of a sequential subset of an amino acid residue sequence disclosed herein. The immunization is typically performed by administering the sample to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the immunogen.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein-Barr virus (EBV), simian virus 40 (SV40), polyoma virus and the like, RNA viruses such as Moloney murine leukemia virus (Mo-MuLV), Rous sarcoma virus and the like, myeloma cells such as P3X63-Ag8.653, Sp2/0-Ag14 and the like.

In preferred embodiments, treatment with the transforming agent results in the production of an "immortalized" hybridoma by fusing the suspended spleen cells with mouse myeloma cells from a suitable cell line, e.g., SP-2, by the use of a suitable fusion promoter. The preferred ratio is about 5 spleen cells per myeloma cell in a suspension containing about $10^8$ spienocytes. A preferred fusion promoter is polyethylene glycol having an average molecule weight from about 1000 to about 4000 (commercially available as PEG 1000, etc.); however, other fusion promoters known in the art may be employed.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The clning is preferably performed in a tissue culture medium that does not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 0.3-0.5) in each separate container (e.g., each well of a microtiter plate). The medium is one (e.g., HAT medium) that does not sustain the drug-resistant (e.g., 8-azaguanine resistant) unfused myeloma cell line.

(e) The tissue culture medium of the cloned transformants is analyzed (immunologically assayed) to detect the presence of antibody molecules that preferentially react with the instant tumor-associated proteins or polypeptides or cells bearing the relevant receptor molecule. This is accomplished using well known immunological techniques.

(f) A desired transformant is then selected and grown in an appropriate tissue culture medium for a suitable length of time, followed by recovery (harvesting) of the desired antibody from the culture supernatant by well known techniques. A suitable medium and length of culturing time are also well known or are readily determined.

To produce a much greater concentration of slightly less pure monoclonal antibody, the desired hybridoma can be transferred by injection into mice, preferably syngenic or semisyngenic mice. The hybridoma causes formation of antibody-producing tumors after a suitable incubation time, which results in a high concentration of the desired antibody (about 5-20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al., *Virol*. 8: 396 (1959)) supplemented with 4.5 gm/l glucose, 20 mM glutamine, and 20% fetal calf serum. A preferred inbred mouse strain is BALB/c.

Methods for producing the instant hybridomas which generate (secrete) the antibody molecules of the present invention are well known in the art and are described further herein. Particularly applicable descriptions of relevant hybridoma technology are presented by Niman et al., *Proc. Natl. Acad. Sci. USA* 80: 4949-4953 (1983), and by Galfre et al., *Meth. Enzymol*. 73: 3-46 (1981), which descriptions are incorporated herein by reference.

A monoclonal antibody can also be produced by methods well known to those skilled in the art of producing chimeric antibodies. Those methods include isolating, manipulating, and expressing the nucleic acid that codes for all or part of an immunoglobulin variable region including both the portion of the variable region comprising the variable region of immunoglobulin light chain and the portion of the variable region comprising the variable region of immunoglobulin heavy chain. Methods for isolating, manipulating, and expressing the variable region coding nucleic acid in procaryotic and eucaryotic hosts are disclosed in the following, the disclosures of which are incorporated by reference herein: Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol*. 4: 1730-1737 (1984); Beher et al., *Science* 240: 1041-1043 (1988); Skerra et al., *Science* 240: 1030-1041 (1988); and Oriandi et al., *PNAS U.S.A.* 86: 3833-3837 (1989). Typically the nucleic acid codes for all or part of an immunoglobulin variable region that binds a preselected antigen (ligand). Sources of such nucleic acids are well known to one skilled in the art and, for example, can be obtained from a hybridoma producing a monoclonal antibody that binds the preselected antigen, or the preselected antigen can be used to screen an expression library coding for a plurality of immunoglobulin variable regions, thus isolating the nucleic acid.

A further preferred method for forming the instant antibody compositions involves the generation of libraries of Fab molecules using the method of Huse et al., *Science* 246: 1275 (1989). In this method, mRNA molecules for heavy and light antibody chains are isolated from the immunized animal. The mRNAs are amplified using polymerase chain reaction (PCR) techniques. The nucleic acids are then randomly cloned into lambda phage to generate a library of recombined phage particles. The phage are used to infect an expression host such as *E. coli*. The *E. coli* colonies and corresponding phage recombinants can then be screened for those producing the desired Fab fragments. Preferred lambda phage vectors are λgt11 and λzap 2.

An antibody molecule-containing composition according to the present invention can take the form of a solution or suspension. The preparation of a composition that contains antibody molecules as active ingredients is well understood in the art. Typically, such compositions are prepared as liquid solutions or suspensions, however, solid forms suitable for solution in, or suspension in, liquid can also be prepared. The preparation can also be emulsified. The active therapeutic ingredient is often mixed with excipients which do not interfere with the assay and are compatible with the active ingredient. Suitable excipients are, for example, water, saline, dextrose, glycerol, ethanol, and the like, and combinations thereof. In addition, if desired, the composition may contain minor amounts of auxiliary substances such as wetting or emulsifying agents, pH buffering agents and the like, which enhance the effectiveness of the active ingredient.

An antibody molecule composition may further be formulated into a neutralized acceptable salt form. Acceptable salts include the acid addition salts (formed with the free amino groups of the antibody molecule) that are formed with inorganic acids such as, for example, hydrochloric or phosphoric acids, or such organic acids as acetic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

4. Therapeutic Compositions

A preferred preparation of a CTL epitope (see Section 2 above), in whatever form, is as a pharmaceutical composition. Similarly, a preferred preparation of in vitro-or in vivo-stimulated CTLs of the present invention, which are intended to be reintroduced to a host, is also as a pharmaceutical composition. In particular, a pharmaceutical composition of the present invention is comprised of one or more molecules which include a polypeptide having substantial homology with a CTL epitope selected from the group of epitopes listed hereinabove, or the polypeptide itself, and a pharmaceutically acceptable carrier or excipient.

One skilled in the art will appreciate that suitable methods of administering a compound to a mammal (e.g. a human patient) for the treatment of a tumor or other malignant condition, for example, which would be useful in the method of of the present invention, are available. Although more than one route can be used to administer a particular compound or composition, a particular route may provide a more immediate and more effective reaction than another route. Accordingly, the described methods provided herein are merely exemplary and are in no way limiting.

Generally, the peptides (or activated CTLs) of the present invention as described above will be administered in a pharmaceutical composition to an individual having a tumor or malignant condition. Those receiving treatment via the methods and compositions of the present invention may be treated with the presently-disclosed peptides and compositions separately or in conjunction with other treatments, as appropriate.

In therapeutic applications, compositions are administered to a patient in an amount sufficient to elicit an effective cytotoxic T lymphocyte response to a specific tumor antigen or antigens and to cure or at least partially arrest tumor-associated symptoms and/or complications. An amount adequate to accomplish this is defined as a "therapeutically or prophylactically effective dose" which may also be described as an "immune response provoking amount." Amounts effective for a therapeutic or prophylactic use will depend on a variety of factors. For example, such factors include the stage and severity of the disease being treated, the age, weight, and general state of health of the patient, and the judgment of the prescribing physician. The size of the dose will also be determined by the peptide composition, method of administration, timing and frequency of administration as well as the existence, nature, and extent of any adverse side-effects that might accompany the administration of a particular compound (or stimulated CTLs) and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is often increased by small increments until the optimum effect under the circumstances is reached. The present inventive method typically will involve the administration of about 0.1 μg to about 50 mg of one or more of the compounds described above per kg body weight of the individual. For a 70 kg patient, dosages of from about 10 μg to about 100 mg of peptide would be more commonly used, followed by booster dosages from about 1 μg to about 1 mg of peptide over weeks to months, depending on a patient's CTL response, as determined by measuring tumor-specific CTL activity in PBLs obtained from the patient. For the reintroduction of stimulated CTLs, which are preferably derived from the patient, typically, a dose would range upward from 1% of the population (number) of cells removed up to all of them (i.e., 100%).

It should be kept in mind that the peptides and compositions of the present invention may generally be employed in serious disease states, that is, life-threatening or potentially life-threatening situations. In such cases, in view of the minimization of extraneous substances and the relative nontoxic nature of the peptides, it is possible—and may be considered desirable by the treating physician—to administer substantial excesses of these peptide compositions. Single or multiple administrations of the within-disclosed compositions can be carried out with dose levels and pattern being selected by the treating physician. In any event, preferred pharmaceutical formulations should provide a quantity of cytotoxic T-lymphocyte-stimulating peptides of the invention sufficient to effectively treat the patient.

For therapeutic use, administration should begin at the first sign of the tumor or malignant condition, or shortly after diagnosis, and continue until the patient's symptoms are substantially abated and for a period thereafter. In well-established or chronic cases, loading doses followed by maintenance or booster doses may be required. Treatment of an affected individual with the compositions of the invention may hasten resolution of the condition in acutely affected individuals.

The pharmaceutical compositions for therapeutic treatment as disclosed herein are generally intended for parenteral, topical, oral or local administration and typically comprise a pharmaceutically acceptable carrier and an amount of the active ingredient sufficient to cause shrinkage or death of the tumor or other malignant tissue, for example. The carrier may be any of those conventionally used and is limited only by physico-chemical considerations, such as solubility and lack of reactivity with the compound, and by the route of administration.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsuiphonic, for example.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The choice of excipient will be determined in part by the particular epitope and epitope formulation chosen, as well as by the particular method used to administer the composition. Accordingly, there is a wide variety of suitable formulations of a pharmaceutical composition according to the present invention. The following formulations for oral, aerosol, parenteral, subcutaneous, intravenous, intramuscular, intraperitoneal, rectal, and vaginal administration are merely exemplary and are in no way limiting.

Preferably, the pharmaceutical compositions are administered parenterally, e.g., intravenously, subcutaneously, intradermally, or intramuscularly. Thus, the invention provides compositions for parenteral administration that comprise a solution of the cytotoxic T-lymphocyte stimulatory peptides dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. (See, e.g., Banker and Chalmers (eds.), *Pharmaceutics and Pharmacy Practice*, J. B. Lippincott Company, Philadelphia, Pa., pp. 238-250, (1982), and Toissel, *ASHP Handbook on Injectable Drugs* (4th ed.), pp. 622-630 (1986).) Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan mono-oleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the present invention for application to skin.

Formulations suitable for oral administration require extra considerations considering the peptidyl nature of the epitopes and the likely breakdown thereof if such compounds are administered orally without protecting them from the digestive secretions of the gastrointestinal tract. Such a formulation can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard-or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The molecules and/or peptides of the present invention, alone or in combination with other suitable components, can be made into aerosol formulations to be administered via inhalation. For aerosol administration, the cytotoxic T-lymphocyte stimulatory peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compounds and polymers useful in the present inventive methods may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In some embodiments, it may be desirable to include in the pharmaceutical composition at least one component that primes CTL generally. Lipids have been identified that are capable of priming CTL in vivo against viral antigens, e.g., tripalmitoyl-S-glycerylcysteinly-seryl-serine ($P_3CSS$), which can effectively prime tumor-specific cytotoxic T lymphocytes when covalently attached to an appropriate peptide. (See, e.g., Deres et al., *Nature* 342: 561-564 (1989). Peptides of the present invention can be coupled to $P_3CSS$, for example and the lipopeptide administered to an individual to specifically prime a cytotoxic T lymphocyte response to a particular tumor cell or tissue. Further, as the induction of neutralizing antibodies can also be primed with $P_3CSS$ conjugated to a peptide that displays an appropriate epitope, e.g., certain p53 epitopes, the two compositions can be combined to elicit more effectively both humoral and cell-mediated responses to tumors or other malignant cells or tissues.

The concentration of cytotoxic T-lymphocyte stimulatory peptides of the present invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected. Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compounds of the present invention may be formulated as inclusion complexes, such as cyclodextrin inclusion complexes, or liposomes. Liposomes serve to target the peptides to a particular tissue, such as lymphoid tissue or malignant cells or tissues. Liposomes can also be used to increase the half-life of the peptide compositions.

Liposomes useful according to the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor (preferably one prevalent among lymphoid cells, such as monoclonal antibodies which bind to the CD45 antigen), or with other therapeutic or immunogenic compositions. Thus, liposomes filled with a desired peptide of the invention can be directed to the site of lymphoid or tumor cells, where the liposomes then deliver the selected therapeutic/immunogenic peptide compositions.

Liposomes for use in the invention are typically formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bibeng.* 9: 467 (1980), and U.S. Pat. Nos. 4,235,871, 4,501,728, 4,837,028 and 5,019,369, the disclosures of which are incorporated herein by reference.

For targeting to the immune cells, a ligand to be incorporated into the liposome can include, for example, antibodies or fragments thereof specific for cell surface determinants of the desired immune system cells. A liposome suspension containing a peptide may be administered intravenously, locally, topically, etc. in a dose that varies according to the mode of administration, the peptide being delivered, the stage of disease being treated, etc.

In another aspect, the present invention is directed to vaccines that contain as an active ingredient an immunogenically effective amount of a cytotoxic T-lymphocyte stimulating peptide, as described herein. The peptide(s) may be introduced into a host—preferably a mammal, e.g. a murine species or a human—linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of tumor cells or tissues (e.g. p53, Her-2/Neu).

Useful carriers are well known in the art, and include, e.g., keyhole limpet hemocyanin, thyroglobulin, albumins (e.g., human serum albumin), tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum or materials well known in the art.

Also, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for a tumor-associated or tumor-specific antigen, and the host becomes at least partially immune to or resistant to the development of the tumor or malignancy to which the antigens relate.

Vaccine compositions containing the peptides of the invention are administered to a patient susceptible to or otherwise at risk of developing the relevant tumor or malignancy, to enhance the patient's own immune response capabilities. Such an amount is defined to be a "immunogenically effective dose" or a "prophylactically effective dose." In this use, the precise amounts again depend on the patient's state of health and weight, the mode of administration, the nature of the formulation, etc., but generally range from about 1.0 µg to about 500 mg per 70 kilogram patient, more commonly from about 50 µg to about 200 mg per 70 kg of body weight.

The peptides of the present invention are preferably administered to individuals of an appropriate HLA type. For example, for vaccine compositions for HLA-A2 individuals, the following peptides can be administered usefully: p53.25-35, LLPENNVLSPL (SEQ ID NO 1); p53.65-73, RMPEAAPPV (SEQ ID NO 2); p53.149-157, STPPPGTRV (SEQ ID NO 3); p53.264-272, LLGRNSFEV (SEQ ID NO 4); HER-3, KIFGSLAFL (SEQ ID NO 10); HER-6, TLQGLGISWL (SEQ ID NO 11); HER-7, VMAGVGSPYV (SEQ ID NO 12); HER-8, VLQGLPREYV (SEQ ID NO 13);

and HER-9, ILLVVVLGV (SEQ ID NO 14). Peptides that are substantially homologous to the foregoing may also be usefully administered according to the present invention.

For therapeutic or immunization purposes, the peptides of the invention can also be expressed by attenuated viral hosts, such as vaccinia. This approach involves the use of vaccinia virus as a vector to express nucleotide sequences that encode the p53 or Her-2/Neu peptides of the invention. Upon introduction into a host, the recombinant vaccinia virus expresses the tumor-related peptide (e.g., p53 or Her-2/Neu peptide) and thereby elicits a host cytotoxic T lymphocyte response to an appropriate tumor-related peptide or protein. Vaccinia vectors and methods useful in immunization protocols are described in, e.g., U.S. Pat. No. 4,722,848. Another vector is BCG (Bacille Calmette Guerin). BCG vectors are described in Stover et al., Nature 351: 456-460 (1991). A wide variety of other vectors useful for therapeutic administration or immunization of the peptides of the invention will be apparent to those skilled in the art from the description herein.

The compositions and methods of the claimed invention may also be employed for ex vivo therapy, wherein, as described briefly above, a portion of a patient's lymphocytes are removed, challenged with a stimulating dose of a peptide of the present invention, and the resultant stimulated CTLs are returned to the patient. Accordingly, in more detail, ex vivo therapy as used herein concerns the therapeutic or immunogenic manipulations that are performed outside the body on lymphocytes or other target cells that have been removed from a patient. Such cells are then cultured in vitro with high doses of the subject peptides, providing a stimulatory concentration of peptide in the cell medium far in excess of levels that could be accomplished or tolerated by the patient. Following treatment to stimulate the CTLs, the cells are returned to the host, thereby treating the tumor or other malignancy. The host's cells may also be exposed to vectors that carry genes encoding the peptides, as described above. Once transfected with the vectors, the cells may be propagated in vitro and/or returned to the patient. The cells that are propagated in vitro may be returned to the patient after reaching a predetermined cell density.

In one method, in vitro CTL responses to tumor-associated proteins (e.g. p53 or Her-2/Neu) are induced by incubating in tissue culture a patient's CTL precursor cells (CTLP) together with a source of antigen-presenting cells (APC) and the appropriate immunogenic peptide. After an appropriate incubation time (typically 1-4 weeks), in which the CTLP are activated and mature and expand into effector CTL, the cells are infused back into the patient, where they will destroy their specific target cell (e.g., a tumor-related-antigen-expressing cell such as a cell expressing Her-2/ Neu). To optimize the in vitro conditions for the generation of specific cytotoxic T cells, the culture of stimulator cells is typically maintained in an appropriate serum-free medium. Peripheral blood lymphocytes are isolated conveniently following simple venipuncture or leukapheresis of normal donors or patients and used as the responder cell sources of CTLp. In one embodiment, the appropriate APC's are incubated with about 10-100 μM of peptide in serum-free media for four hours under appropriate culture conditions. The peptide-loaded APC are then incubated with the responder cell populations in vitro for 5 to 10 days under optimized culture conditions.

Positive CTL activation can be determined by assaying the cultures for the presence of CTLs that kill radiolabeled target cells, both specific peptide-pulsed targets as well as target cells expressing endogenously processed form of tumor-associated (e.g., p53 or Her-2/Neu) antigen as further discussed below. Specifically, the MHC restriction of the CTL of a patient can be determined by a number of methods known in the art. For instance, CTL restriction can be determined by testing against different peptide target cells expressing appropriate or inappropriate human MHC class I. The peptides that test positive in the MHC binding assays and give rise to specific CTL responses are identified as immunogenic peptides. The induction of CTL in vitro requires the specific recognition of peptides that are bound to allele specific MHC class I molecules on APC. Peptide loading of empty major histocompatibility complex molecules on cells allows the induction of primary CTL responses. Because mutant cell lines do not exist for every MHC allele, it may be advantageous to use a technique to remove endogenous MHC-associated peptides from the surface of APC, followed by loading the resulting empty MHC molecules with the immunogenic peptides of interest. The use of non-transformed, non-affected cells, and preferably, autologous cells of patients as APC is desirable for the design of CTL induction protocols directed towards development of ex vivo CTL therapies. Typically, prior to incubation of the APCs with the CTLp to be activated, an amount of antigenic peptide is added to the APC or stimulator cell culture, of sufficient quantity to become loaded onto the human Class I molecules to be expressed on the surface of the APCs. Resting or precursor CTLs are then incubated in culture with the appropriate APCs for a time period sufficient to activate the CTLs. Preferably, the CTLs are activated in an antigen-specific manner. The ratio of resting or precursor CTLs to APCs may vary from individual to individual and may further depend upon variables such as the amenability of an individual's lymphocytes to culturing conditions and the nature and severity of the disease condition or other condition for which the described treatment modality is used. Preferably, however, the CTL:APC ratio is in the range of about 30:1 to 300:1. The CTL/APC may be maintained for as long a time as is necessary to stimulate a therapeutically useable or effective number of CTL.

Activated CTL may be effectively separated from the APC using one of a variety of known methods. For example, monoclonal antibodies specific for the APCs, for the peptides loaded onto the stimulator cells, or for the CTL (or a segment thereof) may be utilized to bind their appropriate complementary ligand. Antibody-tagged molecules may then be extracted from the admixture via appropriate means, e.g., via well-known immunoprecipitation or immunoassay methods.

Effective, cytotoxic amounts of the activated CTLs can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$ to about $5 \times 10^7$ cells used in mice.

Methods of reintroducing cellular components are known in the art and include procedures such as those exemplified in U.S. Pat. No. 4,844,893 to Honsik, et al. and U.S. Pat. No. 4,690,915 to Rosenberg, the disclosures of which are incorporated herein by reference. For example, administration of activated CTLs via intravenous infusion is typically appropriate.

Therapeutic compositions of the present invention contain a physiologically tolerable carrier together with at least one species of therapeutic agent of this invention as described herein, dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a tumor-associated agent (e.g., a polypeptide) of the present invention, typically an amount of at least 0.1 weight percent of agent per weight of total therapeutic composition. A weight percent is a ratio by weight of tumor-associated agent to total composition. Thus, for example, 0.1 weight percent is 0.1 grams of agent per 100 grams of total composition.

A therapeutically effective amount of a tumor-associated agent-containing composition, or beneficial compound therein, is a predetermined amount calculated to achieve the desired effect, i.e., to effectively benefit the individual to whom the composition is administered, depending upon the benefit to be conferred. Thus, an effective amount can be measured by improvements in one or more symptoms associated with the condition of the lymphoproliferative disease occurring in the patient.

Thus, the dosage ranges for the administration of a tumor-associated agent (e.g., a polypeptide) of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted by the individual physician in the event of any complication.

The compositions are administered in a manner compatible with the dosage formulation, and in a therapeutically effective amount. A therapeutic amount of a disclosed composition of this invention is an amount sufficient to produce the desired result, and can vary widely depending upon the disease condition and the potency of the therapeutic compound. The quantity to be administered depends on the subject to be treated, the capacity of the subject's system to utilize the active ingredient, and the degree of therapeutic effect desired. Precise amounts of active ingredient required to be administered depend on the judgment of the practitioner and are peculiar to each individual. However, suitable dosage ranges for systemic application are disclosed herein and depend on the conditions of administration. Suitable regimes for administration are also variable, but are typified by an initial administration followed by repeated doses at one or more hour intervals by a subsequent administration.

5. Therapeutic Methods

Various therapeutic methods are also contemplated by the present invention.

For example, it has now been discovered that peptides derived from p53 and Her-2/Neu proteins are associated with specific tumors (or malignancies) and are capable of being used to stimulate or activate CTLs and may also function as "targeting agents", i.e., activated CTLs are "directed" to seek out cells or tissues expressing or displaying such peptides. Thus, the presently-disclosed compositions and methods expand and enhance treatment options available in numerous conditions in which more conventional therapies are of limited efficacy.

The therapeutic molecules described herein and compositions including same have a number of uses, and may be used in vitro or in vivo. For example, the compositions may be used prophylactically or therapeutically in vivo to disrupt tumor growth or proliferation. Other useful therapeutic methods disclosed herein contemplate that tumor cells will be destroyed via administration of the therapeutic agents and compositions of the present invention.

The present invention also contemplates methods for determining the efficacy of the within-disclosed therapeutic compositions and methods. Exemplary methods for confirming efficacy are described in the Examples hereinbelow. It is expressly to be understood that there are several methods available for determining the effectiveness of the within-described peptides, compositions and therapeutic methods.

The present invention also contemplates methods of isolating "resting" or precursor CTLs. Resting (or precursor) CTL cells—i.e., T cells that have not been activated to target a specific antigen—are preferably extracted from a patient prior to incubation of the CTL cells with the transformed cultures of the present invention. It is also preferred that precursor CTL cells be harvested from a patient prior to the initiation of other treatment or therapy which may interfere with the CTL cells' ability to be specifically activated. For example, if one is intending to treat an individual with a neoplasia or tumor, it is preferable to obtain a sample of cells and culture same prior to the initiation of chemotherapy or radiation treatment. Methods of isolating precursor CTLs are disclosed in U.S. Pat. No. 5,314,813 to Peterson, et al., the disclosures of which are incorporated by reference herein.

Methods of extracting and culturing lymphocytes are well known. For example, U.S. Pat. No. 4,690,915 to Rosenberg describes a method of obtaining large numbers of lymphocytes via lymphocytopheresis. Appropriate culturing conditions used are for mammalian cells, which are typically carried out at 37° C.

Various methods are also available for separating out and/or enriching cultures of precursor CTL cells. Some examples of general methods for cell separation include indirect binding of cells to specifically-coated surfaces. In another example, human peripheral blood lymphocytes (PBL), which include CTL cells, are isolated by Ficoll-Hypaque gradient centrifugation (Pharmacia, Piscataway, N.J.). PBL lymphoblasts may be used immediately thereafter or may be stored in liquid nitrogen after freezing in FBS containing 10% DMSO (Sigma Chemical Co., St. Louis, Mo.), which conserves cell viability and lymphocyte functions.

Alternative methods of separating out and/or enriching cultures of precursor cells include the following example. After lymphocyte-enriched PBL populations are prepared from whole blood, sub-populations of CTL lymphocytes are isolated therefrom by affinity-based separation techniques directed at the presence of the CTL receptor antigen. These affinity-based techniques include flow microfluorimetry, including fluorescence-activated cell sorting (FACS), cell adhesion, and like methods. (See, e.g., Scher and Mage, in *Fundamental Immunology*, W. E. Paul, ed., pp. 767-780, River Press, NY (1984).) Affinity methods may utilize anti-CTL receptor antibodies as the source of affinity reagent. Alternatively, the natural ligand, or ligand analogs, of CTL receptor may be used as the affinity reagent. Various anti-T cell and anti-CTL monoclonal antibodies for use in these methods are generally available from a variety of commercial sources, including the American Type Culture Collection (Rockville, Md.) and Pharmingen (San Diego, Calif.). Depending upon the antigen designation, different antibodies may be appropriate. (For a discussion and review of nomenclature, antigen designation, and assigned antibodies for human leucocytes, including T cells, see Knapp, et al., *Immunology Today* 10: 253-258 (1989).) For example, monoclonal antibodies OKT4 (anti-CD4, ATCC No. CRL 8002) OKT 5 (ATCC Nos. CRL 8013 and 8016), OKT 8 (anti-CD8, ATCC No. CRL 8014), and OKT 9 (ATCC No. CRL 8021) are identified in the ATCC Catalogue of Cell Lines and Hybridomas (ATCC, Rockville, Md.) as being reactive with human T lymphocytes, human T cell subsets, and activated T cells, respectively. Various other antibodies are available for identifying and isolating T cell species.

Preferably, the PBLs are then purified. For example, Ficoll gradients may be utilized for this purpose.

6. Expression Vectors

The choice of vector to which a nucleotide sequence or segment of the present invention is operatively linked depends directly, as is well known in the art, on the functional properties desired, e.g., protein expression, and the host cell to be transformed, these being limitations inherent in the art of constructing recombinant nucleic acid molecules. However, a vector contemplated by the present invention is at least capable of directing the replication, and preferably also expression, of the gene encoding a protein or polypeptide or the present invention included in nucleic acid segments to which it is operatively linked.

In preferred embodiments, a vector contemplated by the present invention includes a procaryotic replicon, i.e., a nucleic acid sequence having the ability to direct autonomous replication and maintenance of the recombinant nucleic acid molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the beneficial protein gene in a bacterial host cell, such as *E. coli*, transformed therewith. A promoter is an expression control element formed by a nucleic acid sequence that permits binding of RNA polymerase and transcription to occur. Promoter sequences compatible with bacterial hosts are typically provided in plasmid vectors containing convenient restriction sites for insertion of a nucleic acid segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eukaryotic cells, preferably those compatible with mammalian cells, can also be used to form the recombinant nucleic acid molecules for use in the present invention. Mammalian cell expression vectors are well known in the art and are available from several commercial sources. Typically, such vectors are provided containing convenient restriction sites for insertion of the desired nucleic acid segment, and provide the signals required for gene expression in a mammalian cell. Typical of such vectors are the pREP series vectors and pEBVhis available from Invitrogen (San Diego, Calif.), the vectors pTDT1 (ATCC #31255), pCP1 (ATCC #37351) and pJ4W (ATCC #37720) available from the American Type Culture Collection (ATCC) and the like mammalian expression vectors.

For controlling expression in mammalian cells, viral-derived promoters are most commonly used. For example, frequently used promoters include polyoma, adenovirus type 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 base pair sequence extending from the HindIII restriction site toward the BgII site located in the viral origin of replication. Also contemplated is using the promoter sequences normally associated with the desired sequence for expression, e.g., adenovirus 2. Origins of replication may be provided either by construction of the vector to include an exogenous origin, such as may be derived from SV40 or other viral sources such as polyoma, baculovirus, or adenovirus or may be provided by the host cell chromosomal replication mechanism. The latter is sufficient for integration of the expression vector in the host cell chromosome.

Adenovirus-based vectors are described in greater detail in published PCT application no. WO94/17832, the disclosures of which are incorporated by reference herein. Other useful vectors are described in the Examples hereinbelow.

A vector of the present invention is a nucleic acid (preferably DNA) molecule capable of autonomous replication in a cell and to which a DNA segment, e.g., gene or polynucleotide, can be operatively linked so as to bring about replication of the attached segment. In the present invention, one of the nucleotide segments to be operatively linked to vector sequences encodes at least a portion of a mammalian Class I MHC molecule. Preferably, the entire peptide-coding sequence of the MHC gene is inserted into the vector and expressed; however, it is also feasible to construct a vector which also includes some non-coding MHC sequences as well. Preferably, non-coding sequences of MHC are excluded. Alternatively, a nucleotide sequence for a soluble ("sol") form of an Class I MHC molecule may be utilized; the "sol" form differs from the non-sol form in that it contains a "stop" codon inserted at the end of the alpha 3 domain or prior to the transmembrane domain. Another preferred vector includes a nucleotide sequence encoding at least a portion of a mammalian β2 microglobulin molecule operatively linked to the vector for expression. It is also feasible to construct a vector including nucleotide sequences encoding both a Class I MHC molecule and a β2 microglobulin.

A preferred vector comprises a cassette that includes one or more translatable DNA sequences operatively linked for expression via a sequence of nucleotides adapted for directional ligation. The cassette preferably includes DNA expression control sequences for expressing the polypeptide or protein that is produced when a translatable DNA sequence is directionally inserted into the cassette via the sequence of nucleotides adapted for directional ligation. The cassette also preferably includes a promoter sequence upstream from the translatable DNA sequence, and a polyadenylation sequence downstream from the mammalian MHC sequence. The cassette may also include a selection marker, albeit it is preferred that such a marker be encoded in a nucleotide sequence operatively linked to another expression vector sequence.

An expression vector is characterized as being capable of expressing, in a compatible host, a structural gene product such as a mammalian Class I MHC polypeptide, a β2 microglobulin, or both. In particular, expression vectors disclosed herein are capable of expressing human Class I MHC molecules and/or human β2 microglobulin.

As used herein, the term "vector" refers to a nucleic acid molecule capable of transporting between different genetic environments another nucleic acid to which it has been operatively linked. Preferred vectors are those capable of autonomous replication and expression of structural gene products present in the nucleotide (DNA) segments to which they are operatively linked.

As used herein with regard to DNA sequences or segments, the phrase "operatively linked" means the sequences or segments have been covalently joined into one piece of DNA, whether in single or double stranded form. The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In various embodiments, a vector is utilized for the production of polypeptides useful in the present invention, including MHC variants and antigenic peptides. Such vectors are preferably utilized in conjunction with bacterial "host" cells adapted for the production of useful quantities of proteins or polypeptides. Such vectors may include a prokaryotic replicon i.e., a nucleotide sequence having the ability to direct autonomous replication and maintenance of the recombinant DNA molecule extra-chromosomally in a prokaryotic host cell, such as a bacterial host cell, transformed therewith. Such replicons are well known in the art. In addition, those embodiments that include a prokaryotic replicon may also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable nucleotide sequences. Exemplary vectors include the plasmids pUC8, pUC9, pUC18, pBR322, and pBR329 available from BioRad Laboratories (Richmond, Calif.), pPL and pKK223 available from Pharmacia (Piscataway, N.J.), and pBS and M13mp19 (Stratagene, La Jolla, Calif.). Other exemplary vectors include pCMU (Nilsson, et al., *Cell* 58: 707 (1989)). Other appropriate vectors may also be synthesized, according to known methods; for example, vectors pCMU/K$^b$ and pCMUII used in various applications herein are modifications of pCMUIV (Nilsson, et al., supra).

A sequence of nucleotides adapted for directional ligation, i.e., a polylinker, is a region of the expression vector that (1) operatively links for replication and transport the upstream and downstream nucleotide sequences and (2) provides a site or means for directional ligation of a nucleotide sequence into the vector. Typically, a directional polylinker is a sequence of nucleotides that defines two or more restriction endonuclease recognition sequences, or restriction sites. Upon restriction cleavage, the two sites yield cohesive termini to which a translatable nucleotide sequence can be ligated to the expression vector. Preferably, the two restriction sites provide, upon restriction cleavage, cohesive termini that are non-complementary and thereby permit directional insertion of a translatable nucleotide sequence into the cassette. In one embodiment, the directional ligation means is provided by nucleotides present in the upstream nucleotide sequence, downstream nucleotide sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

A translatable nucleotide sequence is a linear series of nucleotides that provide an uninterrupted series of at least 8 codons that encode a polypeptide in one reading frame. Preferably, the nucleotide sequence is a DNA sequence. In addition, there is preferably a sequence upstream of the translatable nucleotide sequence encoding a promoter sequence. Preferably, the promoter is conditional (e.g., inducible). A useful conditional promoter as disclosed herein includes a metallothionein promoter or a heat shock promoter.

Vectors may be constructed utilizing any of the well-known vector construction techniques. Those techniques, however, are modified to the extent that the translatable nucleotide sequence to be inserted into the genome of the host cell is flanked "upstream" of the sequence by an appropriate promoter and, in some variations of the present invention, the translatable nucleotide sequence is flanked "downstream" by a polyadenylation site. This is particularly preferred when the "host" cell is an insect cell and the nucleotide sequence is transmitted via transfection. Transfection may be accomplished via numerous methods, including the calcium phosphate method, the DEAE-dextran method, the stable transfer method, electroporation, or via the liposome mediation method. Numerous texts are available which set forth known transfection methods and other procedures for introducing nucleotides into cells; see, e.g., Ausubel, et al. (eds.), *Current Protocols in Molecular Biology*, John Wiley & Sons, NY (1991).

The vector itself may be of any suitable type, such as a viral vector (RNA or DNA), naked straight-chain or circular DNA (either free of, or linked to, other molecules), or a vesicle or envelope containing the nucleic acid material and any polypeptides that are to be inserted into the cell. With respect to vesicles, techniques for construction of lipid vesicles, such as liposomes, are well known. Such liposomes may be targeted to particular cells using other conventional techniques, such as providing an antibody or other specific binding molecule on the exterior of the liposome. See, e.g., A. Huang, et al., *J. Biol. Chem.* 255: 8015-8018 (1 980).

Most useful vectors contain multiple elements including one or more of the following, depending on the nature of the "host" cell—i.e., the cell being transformed: (1) an SV40 origin of replication for amplification to high copy number; (2) an efficient promoter element for high-level transcription initiation; (3) mRNA processing signals such as mRNA cleavage and polyadenylation sequences (and frequently, intervening sequences as well); (4) polylinkers containing multiple restriction endonuclease sites for insertion of "foreign" DNA; (5) selectable markers that can be used to select cells that have stably integrated the plasmid DNA; and (6) plasmid replication control sequences to permit propagation in bacterial cells. In addition to the above, many vectors also contain an inducible expression system that is regulated by an external stimulus. Sequences from a number of promoters that are required for induced transcription have been identified and engineered into expression vectors to obtain inducible expression. Several useful inducible vectors have been based on induction by β-interferon, heat-shock, heavy metal ions, and steroids (e.g. glucocorticoids). (See, e.g., Kaufman, *Meth. Enzymol.* 185: 487-511 (1990).)

In a preferred embodiment, the vector also contains a selectable marker. After expression, the product of the translatable nucleotide sequence may then be purified using antibodies against that sequence. One example of a selectable marker is neomycin resistance. A plasmid encoding neomycin resistance, such as *phshsneo, phsneo,* or *pcopneo*, may be included in each transfection such that a population of cells that express the gene(s) of choice may be ascertained by growing the transfectants in selection medium.

In a preferred embodiment, the translatable nucleotide sequence may be incorporated into a plasmid with an appropriate controllable transcriptional promoter, translational control sequences, and a polylinker to simplify insertion of the translatable nucleotide sequence in the correct orientation, and may be expressed in a eukaryotic cell, such as a cell from a murine species, or in a prokaryotic cell, such as *E. coli*, using conventional techniques. Preferably, there are 5' control sequences defining a promoter for initiating transcription and a ribosome binding site operatively linked at the 5' terminus of the upstream translatable DNA sequence. To achieve high levels of gene expression in transformed or transfected cells—for example, *E. coli*—it is necessary to use not only strong promoters to generate large quantities of mRNA, but also ribosome binding sites to ensure that the mRNA is efficiently translated.

In *E. coli*, for example, the ribosome binding site includes an initiation codon (AUG) and a sequence 3-9 nucleotides long located 3-11 nucleotides upstream from the initiation codon (Shine et al., *Nature* 254: 34 (1975)). The sequence AGGAGGU (SEQ ID NO 39), which is called the Shine-Dalgarno (SD) sequence, is complementary to the 3' end of *E. coli* 16S mRNA. Binding of the ribosome to mRNA and the sequence at the 3' end of the mRNA can be affected by several factors, including (1) the degree of complementarity between the SD sequence and 3' end of the 16S tRNA; and (2) the spacing and possibly the DNA sequence lying between the SD sequence and the AUG. (See, e.g., Roberts et al., *PNAS USA* 76: 760 (1979a); Roberts et al., *PNAS USA* 76: 5596 (1979b); Guarente et al., *Science* 209: 1428 (1980); and Guarente et al., *Cell* 20: 543 (1980).)

Optimization is generally achieved by measuring the level of expression of genes in plasmids in which this spacing is systematically altered. Comparison of different mRNAs shows that there are statistically preferred sequences from positions −20 to +13 (where the A of the AUG is position 0; see, e.g., Gold et al., *Ann. Rev. Microbiol.* 35: 365 (1981)). Leader sequences have also been shown to influence translation dramatically (Roberts et al., 1979 a, b supra). Binding of the ribosome may also be affected by the nucleotide sequence following the AUG, which affects ribosome binding. (See, e.g., Taniguchi et al., *J. Mol. Biol.* 118: 533 (1978).)

One vector which may be used according to the present invention includes a heat shock promoter. Such promoters are known in the art; for example, see Stellar, et al., *EMBO J.* 4: 167-171 (1985). If this promoter is used, it is also preferred to add a polyadenylation site.

One vector suggested for use according to the present invention is a plasmid; more preferably, it is a high-copy-number plasmid. It is also desirable that the vector contain an inducible promoter sequence, as inducible promoters tend to limit selection pressure against cells into which such vectors (which are often constructed to carry non-native or chimeric nucleotide sequences) have been introduced. It is also preferable that the vector of choice be best suited for expression in the chosen host.

Other suitable vectors include retroviral vectors, canary virus vectors, adenovirus and adenovirus-derived vectors, and the like. For example, for a review of gene transfer by using retroviral vectors, see International Applications WO 92/07943 and WO 92/07959, the disclosures of which are hereby incorporated by reference.

A cassette in a DNA expression vector of this invention is the region of the vector that forms, upon insertion of a translatable DNA sequence, a sequence of nucleotides capable of expressing, in an appropriate host, a fusion protein of this invention. The expression-competent sequence of nucleotides is referred to as a cistron. Thus, the cassette preferably comprises DNA expression control elements operatively linked to one or more translatable DNA sequences. A cistron is formed when a translatable DNA sequence is directionally inserted (directionally ligated) between the control elements via the sequence of nucleotides adapted for that purpose. The resulting translatable DNA sequence, namely the inserted sequence, is, preferably, operatively linked in the appropriate reading frame.

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

Thus, a DNA expression vector of this invention provides a system for cloning translatable DNA sequences into the cassette portion of the vector to produce a cistron capable of expressing a fusion protein of this invention.

Successfully transformed cells, e.g., cells that contain a rDNA or cDNA molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.* 98: 503 (1975) or Berent et al., *Biotech.* 3: 208 (1985).

In addition to directly assaying for the presence of recombinant nucleic acid, successful transfection or transformation can be confirmed by well known immunological methods for the presence of expressed protein. For example, cells successfully transformed with an expression vector produce proteins which then can be assayed directly by immunological methods or for the presence of the function of the expressed protein. Other methods of confirming successful transfection or transformation are described in the Examples section.

7. Cell Lines

A preferred cell line of the present invention is capable of continuous growth in culture and capable of expressing mammalian Class I MHC molecules on the surface of its cells. Any of a variety of transformed and non-transformed cells or cell lines are appropriate for this purpose, including bacterial, yeast, insect, and mammalian cell lines. (See, e.g., *Current Protocols in Molecular Biology*, John Wiley & Sons, NY (1991), for summaries and procedures for culturing and using a variety of cell lines, e.g., *E. coli* and *S. cerevisiae*.)

Preferably, the cell line is a eukaryotic cell line. More preferably, the cell line is a mammalian cell line.

In a preferred embodiment, the cell line is a transformed cell line capable of expressing mammalian Class I MHC genes; more preferably, human Class I MHC genes are expressible by the cell line. It is also contemplated that the cell line be capable of expressing mammalian β2 microglobulin, and preferably, that the expressed β2 microglobulin is human β2. A preferred cell line of the present invention is capable of stable or transient expression.

A vector may be utilized to transform/transfect a cell line according to the present invention. Many vectors are available which are useful in the transformation/transfection of cell lines; these vectors are discussed in greater detail above.

In one embodiment, the cDNAs encoding MHC and those encoding β2 microglobulin are operatively linked to separate expression plasmids and are cotransfected into the cultured cells. Alternatively, the cDNAs encoding MHC and β2 microglobulin may be operatively linked to the same expression plasmid and cotransfected via that same plasmid. In another variation, cDNAs encoding MHC, β2 microglobuiin, and a cytokine such as IL2 are operatively linked to expression plasmids and are cotransfected into a cell line of the present invention.

Successfully transformed cells, i.e., cells that contain an expressible human nucleotide sequence according to the present invention, can be identified via well-known techniques. For example, cells resulting from the introduction of a cDNA or rDNA of the present invention can be cloned to produce monoclonal colonies. Cells from those colonies can be harvested, lysed, and their DNA content examined for the presence of the rDNA using a method such as that described by Southern, *J. Mol. Biol.* 98: 503 (1975). In addition to directly assaying for the presence of rDNA, successful transformation or transfection may be confirmed by well-known immunological methods when the rDNA is capable of directing the expression of a subject chimeric polypeptide. For example, cells successfully transformed with an expression vector may produce proteins displaying particular antigenic properties which are easily determined using the appropriate antibodies. In addition, successful transformation/transfection may be ascertained via the use of an additional vector bearing a marker sequence, such as neomycin resistance, as described hereinabove.

In order to prepare the culture for expression of MHC molecules, the culture may first require stimulation, e.g., via $CuSO_4$ induction, for a predetermined period of time. After a suitable induction period—e.g., about 12-48 hours, peptides may be added at a predetermined concentration (e.g., about 100 μg/ml). Peptides may be prepared as discussed hereinafter. After a further incubation period—e.g., for about 12 hours at the appropriate temperature—the culture is ready for use in the activation of CD8 cells. While this additional incubation period may be shortened or perhaps admitted, it is our observation that the culture tends to become increasingly stable to temperature challenge if it is allowed to incubate for a time prior to addition of resting or precursor CTL (CD8) cells.

Nutrient media useful in the culturing of transformed host cells are well known in the art and can be obtained from numerous commercial sources. In embodiments wherein the host cell is mammalian, a "serum-free" medium is preferably used.

8. Diagnostic Methods and Systems

In one embodiment, the present invention contemplates a method for detecting antibodies—including autoantibodies—to specific proteins and polypeptides, or polypeptide portions thereof. The assays disclosed herein may also be used to detect molecules that are homologs or analogs of such proteins and polypeptides, as well.

Assays according to the present invention may, for example, be made specific for antibodies relating to tumor cells or tissues by a proper selection of appropriate antigens and antibodies. For example, an assay system according to the present invention may be used to detect antibodies to p53 proteins, polypeptides, or portions thereof. Alternatively, an assay according to the present invention may be useful in the detection of antibodies to Her-2/Neu proteins, polypeptides, or portions thereof. Typically, the assay methods involve detecting antibodies present in a body sample, such as a body fluid sample (e.g., blood).

Assays for detecting antigens—e.g., proteins and polypeptides—are also contemplated herein. For example, the present invention discloses methods for identifying proteins or polypeptides associated with tumors or other malignant cells and tissues.

In one exemplary method, the relative binding affinity of a reagent molecule for its target species is conveniently determined as described herein using the method of flow microfluorometry (FMF.). Thus, cells expressing the target antigen, e.g., a p53-derived or a Her-2/Neu-derived peptide, are indicated whenever the fluorescence intensity associated with the cells due to binding of the instant fluorescent-labeled antibodies to cell surface antigens exceeds a predefined threshold level. The labeled antibodies are typically fluorescein isothiocyanate-conjugated (FITC), although other well known fluorescent labels may be used.

Another aspect of the present invention is directed to a method of provoking an immune response to a p53 or Her-2/Neu antigen, comprising contacting a suitable cytotoxic T lymphocyte with an immune response provoking effective amount of a molecule comprising a peptide selected from the group of CTL epitopes recited hereinabove. All of the variations recited hereinabove regarding the molecule of the present invention and the polypeptide that such a molecule includes may be used in the context of the method of provoking an immune response.

Such a contact between the CTL epitope-containing molecule, which may be the CTL epitope alone or a complex of radiolabeled CTL epitope, for example, or some other CTL epitope analog as described above, and a CTL may occur in vitro or in vivo. Accordingly, after having effected such a contact, after which the CTLs are stimulated with respect to the antigen with which it was placed in contact, the CTLs may then be returned to the originating host (e.g. a patient in need of treatment), for a therapeutic purpose, as further discussed below.

A diagnostic purpose, of course, is satisfied whether the contacted cells are returned to the host or not. That purpose is to answer whether the CTLs of the host can bind the tested epitope (however configured) and, if so, be stimulated by it. Indeed, the present invention contemplates various assay methods for detecting, in a population of lymphocytes of a mammal, cytotoxic T cells that respond to a T cell epitope of a tumor antigen, which is understood to be a consequence of a classic ligand-receptor binding phenomenon. The present invention further contemplates assays for the determination of the strength of such binding, using methods well known in the field of ligand-receptor interaction.

Thus, one aspect of the present invention is directed to a method of detecting—in the lymphocytes of a mammal—cytotoxic T cells that respond to a particular T cell epitope of a tumor-associated antigen such as p53 or Her-2/Neu. This method, referred to herein as "Diagnostic 1", comprises the steps of: (a) contacting target cells with a molecule comprising at least one of the peptides selected from the group of epitopes recited hereinabove, wherein the target cells are of the same HLA class as the lymphocytes to be tested for the cytotoxic T cells; (b) contacting the lymphocytes to be tested for the cytotoxic T cells with a molecule comprising at least one of the peptides selected from the same group of epitopes listed hereinabove, or ones substantially homologous thereto, under conditions sufficient to restimulate the tumor-specific CTL to respond to appropriate target cells; and (c) determining whether the tested lymphocytes exert a cytotoxic effect on the target cells, thereby indicating the presence of CTL that recognize a T-cell epitope of a tumor-associated protein (e.g., p53 or Her-2/Neu).

Another preferred embodiment is directed to a method of detecting (in lymphocytes of a mammal) CTLs that have receptors that can bind to a particular T cell epitope of tumor-related antigen such as p53 or Her-2/Neu. This second embodiment, referred to herein as "Diagnostic 2", comprises the following steps: (a) contacting the lymphocytes to be tested for the CTLs with a molecule comprising a suitable label and at least one of the peptides selected from the same group of epitopes listed hereinabove, or ones substantially homologous thereto, under suitable conditions of time, temperature, humidity, salts, nutrients, and pH sufficient to restimulate the tumor-specific CTL to respond to appropriate target cells; (b) harvesting such contacted cells and washing with medium in the absence of the labeled molecule sufficient to remove any unbound labeled molecule; and (c) measuring the bound labeled molecule using suitable measuring means. Step (b) may alternatively be accomplished by lysing the cells using a hypotonic solution with or without unlabeled molecule or other means known in the art, and preparing a membrane fraction that is free of unbound labeled molecule.

A suitable label used in the context of this method includes radioactive isotope tagged molecules, wherein constituent nonradioactive atoms of the molecule have been replaced with radioactive ones, such as $^3$H, $^{14}$C, or $^{35}$S, or if a benzene ring or other suitable group is included in the molecule, $^{125}$I can be affixed thereto. Other suitable labels include fluorescent groups such as fluorescein isothiocyanate or rhodamine isothiocyanate, that can be affixed covalently to appropriate amino acid side groups using methods well known in the art, as well as enzymes that can convert a substrate from one color to another, such as alkaline phosphatase. A suitable measuring means includes a scintillation gamma ray, or Geiger counter and the like, as well as a spectrophotometer, even just a color chart for eyeball comparisons of a reaction color to published standards that indicate certain concentrations of bound ligand, i.e., peptide.

Specific methods used for procuring the cells from a patient, culturing them, and determining the existence and/or extent of cytotoxicity of a given population of cells are well known in the art. It is also contemplated that the contacting of host lymphocytes occurring in the aforedescribed diagnostic procedures may take place in vivo on in vitro. If the contacting takes place in vivo, then it is preferred that when one is using "Diagnostic 1", step (a) and (c) take place in vitro. If the method identified herein as "Diagnostic 2" is selected, steps (b) and (c) also take place in vitro. Accordingly, the present invention provides for the detection of human CTL, for instance in blood or other tissues of patients known or suspected to be producing antibodies to tumor-specific antigens—e.g., antibodies to p53-derived peptides—by appropriately adapting methods known for detecting other human CTL. (See, e.g., Clerici, et al., *J. Immunol.* 146: 2214-2219 (1991).) Additionally, the present invention provides methods for the detection of cells having receptors specific to the peptides of the present invention.

The assays of this invention are also useful for determining whether the immune system of a mammal has been provoked by the above recited epitopes of p53, Her-2/Neu, or other tumor-specific antigens, thereby determining whether the occurrence and magnitude of such a response can be correlated with either the occurrence of a tumor or other malignancy (i.e., for diagnosis) or the severity of the pathogenic effect of the malignancy or tumor (i.e., as a prognostic indicator).

Accordingly, a peptide of the invention may be used to determine the susceptibility of a particular individual to a treatment regimen that employs a peptide (or derivative thereof) of the present invention, and thus may be helpful in modifying an existing treatment protocol or in determining the prognosis for an affected individual. In addition, the presently-disclosed peptides may be used to monitor the effectiveness of a particular therapeutic protocol.

The contact between a molecule of the present invention (in any of its various forms) and CTL that has been described above as an in vitro procedure also preferably occurs in vivo—i.e., in a mammal, including murine species, humans and other mammalian species—as further described in the Examples that follow. Introduction of the CTL epitope, in one of its hitherto-described forms, may be usefully provided to an individual afflicted with a tumor or other malignancy.

A method for detecting an antigenic protein or polypeptide of the present invention preferably comprises formation of an immunoreaction product between the protein or polypeptide and an anti-polypeptide antibody molecule, as disclosed herein. The antigen to be detected may be present in a vascular fluid sample or in a body tissue sample. The immunoreaction product is detected by methods well-known to those skilled in the art. Numerous clinical diagnostic chemistry procedures may be utilized to form the detectible immuno-complexes.

Alternatively, a protein or polypeptide ligand (non-antibody composition) for a within-disclosed tumor-associated receptor or polypeptide may be used in the within-described assay methods. Thus, while exemplary assay methods are described herein, the invention is not so limited.

One useful method comprises admixing a body sample, preferably one obtained from a human donor or patient, containing cells and/or fluid to be analyzed with one of the within-described antibody compositions that are capable of immunoreacting with Her-2/Neu or p53 proteins or polypeptides. The cell sample may also be washed prior to the admixing step. The immunoreaction admixture thus formed is maintained under appropriate assay conditions—e.g., biological assay conditions—for a time period sufficient for any cells expressing the antigen, or for any soluble antigen, to immunoreact with antibodies in the antibody composition to form an antibody-receptor immunocomplex. The immunoreaction product (immunocomplex) is then separated from any unreacted antibodies present in the admixture. The presence, and if desired, the amount of immunoreaction product formed is then determined. The amount of product formed may then be correlated with the amount of receptors expressed by the cells, or with the amount of soluble antigen expressed.

Determination of the presence or amount of immunoreaction product formed depends upon the method selected for identifying the product. For instance, a labeled antibody may be used to form a labeled immunocomplex with a protein or polypeptide of the present invention (e.g., a p53-derived polypeptide). The labeled immunocomplex may be quantitated by methods appropriate for detecting the respective label—e.g., fluorescent labels, radioactive labels, biotin labels and the like—as discussed hereinbelow. Alternatively, an unlabeled antibody may be used to form an unlabeled immunocomplex, which is subsequently detected by immunoreacting a labeled antibody recognizing the unlabeled antibody with the unlabeled immunocomplex. The immunocomplex thereby becomes labeled and may be detected as described above.

Biological conditions used in the instant assays are those that maintain the biological activity of the antibody and proteins or polypeptide molecules of this invention. Those conditions include a temperature range of about 4° C. to about 45° C., preferably about 37° C., at a pH value range of about 5 to about 9, preferably about 7, and an ionic strength varying from that of distilled water to that of about one molar sodium chloride, preferably about that of physiological saline. Methods for optimizing such conditions are well known in the art.

In a preferred embodiment, a body sample to be analyzed is withdrawn from a donor or patient and apportioned into aliquots. At least one aliquot is used for the determination of antigen expression using an antibody composition of the present invention. If desired, a second aliquot may be used for determining reactivity of a control antibody with the sample. The analyses may be performed concurrently but are usually performed sequentially.

In a further aspect of the invention, data obtained in the instant assays are recorded via a tangible medium, e.g., computer storage or hard copy versions. The data can be automatically input and stored by standard analog/digital (A/D) instrumentation that is commercially available. Also, the data can be recalled and reported or displayed as desired for best presenting the instant correlations of data. Accordingly, instrumentation and software suitable for use with the present methods are contemplated as within the scope of the present invention.

The antibody compositions and methods of the invention afford a method of diagnosing the presence of tumor cells or malignant cells in individuals suspected of, or at risk of, various types of tumors or cancers (e.g., small cell lung cancer) and other diseases in which expression of an identifiable protein or polypeptide is correlated with the disease state. Accordingly, a method of monitoring a patient's response to treatment is further contemplated in which a marker for the disease is detectable and/or detected. The method comprises admixing a body sample containing cells to be assayed for expression of a tumor-associated marker with an antibody composition of the present invention, according to an assay method as described above. The admixture is maintained for a time period sufficient to form an immunoreaction product under predefined reaction conditions. The amount of immunoreaction product formed is correlated to an initial disease state. These steps are repeated at a later time during the treatment regimen, thereby permitting determination of the patient's response to treatment, with a decrease in the number of cells expressing the disease-associated protein or polypeptide indicating an improvement in the disease state.

Diagnostic systems for performing the described assays are also within the scope of the present invention. A diagnostic system of the present invention is preferably in kit form and includes, in an amount sufficient for at least one assay, a composition containing antibody molecules of the present invention (or fragments thereof) as a separately packaged reagent. The antibody molecules may be labeled, or a labeling reagent may be separately packaged and included within the kit, wherein the label is capable of indicating whether or not an immunoreaction product is present. Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be admixed, maintenance time periods for reagent/sample admixtures, temperature, buffer conditions, and the like.

In one embodiment, a diagnostic system is contemplated for use in assaying for the presence of tumor-associated proteins and/or polypeptides, whether or not said proteins/polypeptides are expressed on cell surfaces.

An exemplary kit is thus provided as an enclosure (package) comprising a container for novel agents of the present invention. In one example, such agents comprise antibody combining site-containing molecules which are capable of immunoreacting with tumor associated molecules on cells in a cell sample. The term "antibody combining site" refers to that structural portion of an antibody molecule comprised of a heavy and light chain variable and hypervariable regions that specifically binds (immunoreacts with) antigen. Typically, a kit will also contain a labeled antibody probe that immunoreacts with the immunocomplex formed, e.g., when an antibody and its cognate receptor, protein, or polypeptide immunoreact.

In another variation, a kit according to the present invention is provided as an enclosure (package) that comprises a container including antibody combining site-containing molecules capable of immunoreacting with ligand molecules, whether or not the ligand molecules are attached to, or free of, cellular material in the test sample. Typically, the kit also contains a labeled antibody probe that immunoreacts with the immunocomplex of the antibody combining site-containing molecule and the ligand molecule.

The label may be any of those commonly available, including, without limitation, fluorescein, phycoerythrin, rhodamine, $^{125}$I, and the like. Other exemplary labels include $^{111}$In, $^{99}$Tc, $^{67}$Ga, and $^{132}$I and nonradioactive labels such as biotin and enzyme-linked antibodies. Any label or indicating means that may be linked to or incorporated in an antibody molecule is contemplated as part of an antibody or monoclonal antibody composition of the present invention. A contemplated label may also be used separately, and those atoms or molecules may be used alone or in conjunction with additional reagents. Many useful labels of this nature are known in clinical diagnostic chemistry.

The linking of labels to polypeptides and proteins is also well known. For instance, antibody molecules produced by a hybridoma may be labeled by metabolic incorporation of radioisotope-containing amino acids provided as a component in the culture medium. See, for example, Galfre et al., *Meth. Enzymol.* 73: 3-46 (1981). The techniques of protein conjugation or coupling through activated functional groups are particularly applicable. See, for example, Aurameas, et al., *Scand. J. Immunol.* 8. *Suppl.* 7: 7-23 (1978), Rodwell et al., *Biotech.* 3: 889-894 (1984), and U.S. Pat. No. 4,493,795 (the latter of which is incorporated by reference herein).

An instant diagnostic system may also include a specific binding agent. A "specific binding agent" is a chemical species capable of selectively binding a reagent species of the present invention but is not itself an antibody molecule of the present invention. Exemplary specific binding agents are antibody molecules, complement proteins or fragments thereof, protein A and the like that react with an antibody molecule of this invention when the antibody is present as part of the immunocomplex described above. In preferred embodiments the specific binding agent is labeled. However, when the diagnostic system includes a specific binding agent that is not labeled, the agent is typically used as an amplifying means or reagent. In these embodiments, a labeled specific binding agent is capable of specifically binding the amplifying means when the amplifying means is bound to a complex containing one of the instant reagents.

For example, a diagnostic kit of the present invention may be used in an "ELISA" format to detect the presence or quantity of a tumor-associated protein or polypeptide in a body sample or body fluid sample such as serum, plasma or urine or a detergent lysate of cells, e.g., a 10 mM CHAPS lysate. "ELISA" refers to an enzyme-linked immunosorbent assay that employs an antibody or antigen bound to a solid phase and an enzyme-antigen or enzyme-antibody conjugate to detect and quantify the amount of antibody or antigen present in a sample. A description of the ELISA technique is found in Chapter 22 of the 4th Edition of *Basic and Clinical Immunology* by D. P. Sites et al., published by Lange Medical Publications of Los Altos, Calif. in 1982; and in U.S. Pat. Nos. 3,654,090; No. 3,850,752; and No. 4,016,043, which disclosures are incorporated herein by reference.

In preferred embodiments, the antibody or antigen reagent component may be affixed to a solid matrix to form a solid support that is separately packaged in the subject diagnostic systems. The reagent is typically affixed to the solid matrix by adsorption from an aqueous medium, although other modes of affixation well known to those skilled in the art may be used, such as specific binding methods. For example, an instant anti-tumor-associated-polypeptide antibody may be affixed to a surface and used to assay a solution containing tumor-associated molecules or cells expressing or displaying such molecules. Alternatively, tumor-associated proteins, their homologs, polypeptide fragments of tumor-associated proteins or their homologs, and whole or partially lysed cells expressing any of the foregoing may be affixed to the surface and used to screen a solution for antibody compositions that immunoreact with the affixed species.

Useful solid matrix materials in this regard include the derivatized cross-linked dextran available under the trademark SEPHADEX from Pharmacia Fine Chemicals (Piscataway, N.J.), agarose in its derivatized and/or cross-linked form, polystyrene beads about 1 micron to about 5 millimeters in diameter (available from Abbott Laboratories of North Chicago, Ill.), polyvinyl chloride, polystyrene, cross-linked polyacrylamide, nitrocellulose-or nylon-based webs such as sheets, strips or paddles, tubes, plates, the wells of a microtiter plate such as those made from polystyrene or polyvinylchloride, and the like.

The reagent species, labeled specific binding agent or amplifying reagent of any diagnostic system described herein may be provided in solution, as a liquid dispersion or as a substantially dry powder, e.g., in lyophilized form. Where the indicating means is an enzyme, the enzyme's substrate may also be provided in a separate package of a kit or system. Usually, the reagents are packaged under an inert atmosphere. A solid support such as the before-described microtiter plate and one or more buffers may also be included as separately packaged elements in this diagnostic assay system.

The diagnostic system is usually contained in a conventional package. Such packages include glass and plastic (e.g., polyethylene, polypropylene and polycarbonate) bottles, vials, plastic and plastic-foil laminated envelopes and the like.

It should also be understood that various combinations of the embodiments described herein are included within the scope of the present invention. Other features and advantages of the present invention will be apparent from the descriptions hereinabove, from the Examples to follow, and from the claims.

EXAMPLES

The following examples are intended to illustrate, but do not limit, the present invention.

Example 1

CTL-Mediated Lysis of Target Cells Expressing p53-Specific Peptides

A. Preparation of HLA-A2.1/$K^b$-restricted p53 Peptide-Specific Cytotoxic T Lymphocytes (CTL)

Cytotoxic T lymphocytes (CTL) specific for p53 peptide were prepared by designing and synthesizing peptides derived from p53 which are capable of being bound by HLA A2.1 molecules, immunizing HLA-A2.1/$K^b$ (A2.1/$K^b$) transgenic mice in vivo with the p53 peptide, and generating p53 peptide-specific CTL cell lines derived from the immunized transgenic mice. Details of these procedures are as outlined below.

1. Preparation of p53 Peptides
a. Peptide Design

Peptides which comprise 8 to 11 amino acid residues in length can be accommodated within the peptide binding groove of the HLA molecule. The length of the bound peptide is restricted by the interaction of the amino and carboxyl termini of the peptide with the extremities of the peptide binding groove (Madden et al., *Nature* 353: 321-325 (1991)). Amino acid residue sequence analysis of MHC I-bound peptides has revealed conservation of amino acid residues at defined amino acid residue positions (Falk, et al., *Nature* 351: 290-296 (1991)). These amino acid residues are believed to interact with pockets in the MHC I peptide binding groove (Madden et al. *Nature* 351: 321-325 (1991); Fremont et al. *Science* 257: 919-927 (1992)).

The p53-derived peptides are based on the naturally-occurring sequence of the human p53 gene. The peptides are designated according to the amino acid residue position from which they are derived, e.g., "p53.25-35" represents amino acid residues from position 25 to 35 of the human p53 gene sequence (Hinds, et al., *Cell Growth Diff.* 1: 571 (1990)). The p53-derived peptides p53.25-35 and p53.65-73 are described in Houbiers, et al., *Eur. J. Immunol.* 23: 2072-2077 (1993). Peptides p53.264-272 and p53.149-157 were designed as described below.

The p53.264-272 and p53.149-157 peptides were based on 8-11 amino acid A2-restricted peptide motifs (Falk, et al., *Nature* 351: 290 (1991); Hunt, et al., *Science* 255: 1261 (1992)). The peptide motif designates a leucine, isoleucine, methionine, valine, alanine, or threonine at the second amino acid residue position and a valine, leucine, isoleucine, alanine, methionine, or threonine at the carboxy terminal amino acid residue position. The second and carboxy terminal amino acid residue positions serve as anchor residues whereby the peptide interacts with the peptide binding groove. The naturally-occurring amino acid residue sequence of human p53 was thus examined for sequential subsets of amino acid residues which correspond to the A2-restricted peptide motif. The p53-derived peptides disclosed herein do not represent all of the peptides which correspond to this motif; rather, they are considered exemplary. Therefore, the invention should not be considered to be limited to the peptides disclosed herein.

The amino acid residue sequence of the p53-specific peptides used as immunogens following this motif are listed with their respective SEQ ID NOS in Table 1. Also given are the amino acid residue sequences of additional peptides used as control peptides for binding to A2. For example, the HIVpol 510-518 peptide is derived from the polymerase gene of the Human Immunodeficiency Virus (HIV), from amino acid residue 510 to 518. It was selected as it has been reported to bind efficiently to A2. The FLU NP 365-373 peptide, derived from the influenza A matrix peptide from amino acid residue 365 to 373, has previously been shown to bind to H-2D$^b$. The VSV N 52-59 peptide is derived from a nuclear protein from Vesicular Stomatitis Virus (VSV), and included amino acid residues 52 to 59; this peptide has been described as binding to K$^b$.

TABLE 1

| Peptide Designation | Amino Acid Residue Position | Amino Acid Residue Sequence | SEQ ID NO |
| --- | --- | --- | --- |
| p53.25-35 | 25-35 | LLPENNVLSPL | 1 |
| p53.65-73 | 65-73 | RMPEAAPPV | 2 |
| p53.149-157 | 149-157 | STPPPGTRV | 3 |
| p53.264-272 | 264-272 | LLGRNSFEV | 4 |
| HIV pol 510-518 | 510-518 | ILKEPVHGV | 5 |
| FLU NP 365-373 | 365-373 | ASNENMETM | 6 |
| VSV N 52-59 | 52-59 | RGYVYQGL | 7 | b. Peptide Synthesis and Analysis

The peptides listed in Table 1 were synthesized on a peptide synthesizer (430A; Applied Biosystems, Foster, Calif.) as previously described (Sette, et al. *J. Immunol.* 142: 35 (1989)). The peptides were routinely determined to be of 70-95% purity.

2. In Vitro Binding of p53-Specific Peptides to A2.1/K$^b$

The efficiency with which each p53-specific peptide and control peptide (test peptide) was bound by A2.1/K$^b$ was determined in a competitive binding assay. In this assay, each test peptide was incubated with target cells which express A2.1/K$^b$ on the cell surface in the presence of a peptide derived from the influenza A virus matrix protein (influenza A-specific peptide) which appears to bind efficiently to A2.1/K$^b$ (Vitiello, et al., *J. Exp. Med.* 173: 1007-1015 (1991)). During this incubation, the test peptide and influenza A-specific peptide compete for binding to the A2.1/K$^b$. The efficiency with which the A2.1/K$^b$ bound the influenza A-specific peptide was then determined by incubating the target cells with influenza A-specific CTL (effector cells) and assaying for lysis of the target cells. If the A2.1/K$^b$ bound the test peptide to a higher degree than the influenza A-specific peptide, inefficient influenza A-specific CTL-mediated lysis of the target cells would result. If the A2.1/K$^b$ had bound the influenza A-specific peptide to a higher degree than the test peptide, efficient lysis of the target cells would result. The efficiency with which the target cells bind the test peptide can thus be expressed as the percent inhibition of influenza A-mediated lysis of the target cells. The ratio of effector to target cells was varied within each experiment to demonstrate the dose-dependent relationship between the effector and target cells.

Additional peptides were also assayed to provide further evidence that the peptides were binding specifically to the A2 molecule. For example, the peptide HIV pol 510-518 has previously been shown to bind efficiently to A2. It was therefore predicted that binding of this peptide to A2 would inhibit efficient binding of the influenza A-specific peptide to A2 and reduce the ability of the influenza A-specific CTL to lyse the target cells. The peptides VSV N 52-59 and FLU NP 365-373 have been shown to bind to K$^b$ and H-2D$^b$, respectively, but not to A2. It was thus predicted that these latter two peptides would not bind to A2 efficiently and would therefore allow the influenza A-specific peptide to bind to A2. The binding of the influenza A-specific peptide to A2 would result in the efficient lysis of the target cells by influenza A-specific CTL. The amino acid residue sequences of the control peptides and their respective SEQ ID NOS are given in Table 1.

a. Preparation of A2.1/K$^b$ Transgenic Mice

The A2.1/K$^b$ transgenic mice used in these examples were generated previously and are described in Vitiello, et al. Id. Briefly, A2.1/K$^b$ transgenic mice were produced using a standard protocol (Hogan, et al., *Manipulating the Mouse Embryo: A Laboratory Manual*, Cold Spring Harbor Laboratory, Cold Spring Harbor, N.Y. (1986)). The A2.1/K$^b$ chimeric gene (Irwin, et al., *J. Exp. Med.* 170: 1091 (1989)) was injected into fertilized eggs obtained by crossing (C57BL/6× DBA/2)F$_1$ mice. Transgenic mouse lines were established by identifying mice that had integrated the transgene as detected by tail DNA dot blot analysis (Sambrook et al. (eds), *Molecular Cloning: A Laboratory Manual*, Cold Spring Harbor, N.Y. (1989)). The selection of two transgenic lines, identified as "66" and "372", was based upon cell surface expression of the A2.1/K$^b$ gene determined by FACS analysis as described below. Line 66 was made homozygous and was renamed Line "6". A transgenic mouse from line 6 was used in the examples described herein.

b. Detection of Cell Surface Expression of A2

Cell surface expression of A2.1/K$^b$ was determined as described in Irwin, et al. (Id.). Spleen cells (about 10$^6$ cells) or about 0.5 ml peripheral blood was collected from the transgenic mouse tail vein and treated with 5 ml Tris-buffered ammonium chloride to lyse the red blood cells. The remaining cells were washed and resuspended in RPMI 10% supplemented with 2.5 microgram/milliliter (μg/ml) Con A, 250 nanogram/milliliter (ng/ml) ionomycin, 3 ng/ml PMA (phorbol myristate acetate; Sigma, St. Louis, Mo.), and 5% volume/volume (v/v) culture supernatant of Con A-activated rat splenocytes. The samples were incubated at a cell density of 3×10$^6$ cells/well in a volume of 2 ml for 3 days at 37° C. in a humidified 5% CO$_2$ atmosphere.

The cell-surface expression of A2.1/K$^b$ on the spleen or peripheral blood cells of transgenic mice or on the Con A-stimulated cells described above was verified by flow cytometry (FACS IV; Becton Dickinson & Co., Mountain View, Calif.) according to the manufacturer's instructions. The biotinylated HLA-A2.1-specific monoclonal antibody MA2.1 (McMichael, et al. *Hum. Immunol*. 1: 121 (1980)) and phycoerythrin-conjugated streptavidin (Biomeda, Foster City, Calif.) were used in conjunction with the FACS analysis.

c. Preparation of A2.1/$K^b$-Restricted Influenza A Peptide-Specific CTL

Influenza A virus peptide-specific CTL (effector cells) capable of efficiently lysing target cells displaying influenza A-specific peptide bound to A2.1/$K^b$ on their surface were generated as previously described for other p53-derived peptides in Vitieilo, et al., Id. The influenza A-specific peptide used in these studies was derived from amino acid residues 58 to 66 of the influenza A virus matrix protein and is thus identified herein as M1 (58-66) (influenza A-specific peptide; GILG-FVFTL; SEQ ID NO 8). The M1 (58-66) peptide is alternatively called "G-matrix peptide" as noted in subsequent experiments; since M1 (58-66) and G-matrix peptides have the same amino acid residue sequence, they are therefore given the same SEQ ID NO. The influenza A-specific CTL identified is designated both as "Clone 12" and "A clone 12". Clone 12 (A clone 12) is capable of specifically lysing target cells which have M1(58-66) bound to A2 on the surfaces of cells. Clone 12 is used in binding inhibition assays as described herein to determine whether a specific peptide has been bound to A2 on the surface of cells.

d. Preparation of Target and Stimulator Cells

The target cells used in the peptide binding inhibition assay express A2.1/$K^b$ on their cell surfaces. The target cells are incubated with a selected peptide and an influenza A-specific peptide to allow the peptides to compete for binding to A2.1/$K^b$. Binding of the peptide to A2.1/$K^b$ is demonstrated by subsequently assaying for the ability of influenza A-specific CTL to lyse the target cells.

Stimulator cells were used in the maintenance of peptide-specific CTL populations as described in Example 1A2d. Preparation of these cells is described below.

1) EA2 Cells

The EA2 target cells used in the binding inhibition assays are also used as stimulator cells in the maintenance of peptide-specific CTL populations. The EA2 cells described herein are produced from EL-4 murine thymoma cells originally derived from C57BL/6 mice.

The EL-4 cells are stably transfected with the A2.1/$K^b$ chimeric gene as previously described (Irwin, et al., *J. Exp. Med*. 170: 1091 (1989)). Briefly, pSV2 plasmids containing the chimeric construct A2.1/$K^b$ were cotransfected with the pSV2 neo plasmid containing the neomycin resistance gene (Clontech, Palo Alto, Calif.) into the EL-4 cell line. Approximately $10^7$ EL-4 cells in 1 ml phosphate buffered saline (PBS) were mixed with 10 μg of pSV2 plasmid containing the chimeric A2.1/$K^b$ gene and 2 μg of pSV2 neo plasmid in a 1-mi cuvette. Cells were transfected by electroporation using an X-Cell 450 transfection apparatus (Promega Biotec, Madison, Wis.), with a 50-msec discharge, constant voltage (400 mV), and capacitors charged to 800 mfd.

Transfected EL-4 cells were grown In RPM 1640 containing 10% fetal calf serum (FCS), 2 mM L-glutamine, 50 μg/ml gentamicin, and $5 \times 10^{-5}$ M β-mercaptoethanol (RPMI 10%). After a 24 hour incubation, transfected EL-4 cells were selected for neomycin resistance by the addition of 400 μg/ml of G418 (Gibco Laboratories, Grand Island, N.Y.). Neomycin-resistant cells were subcloned and tested for cell surface expression of A2.1/$K^b$ by FACS analysis as described in Example 1A2b.

The expression of neomycin-resistant cells was compared to untransfected EL-4 cells using an A2.1-specific monoclonal antibody and a Fc fragment-specific, F(ab')$^2$ FITC-conjugated goat anti-mouse IgG (Pel-Freez Biologicals, Rogers, Ark.). The resultant EA2 cell line was maintained in RPMI 10% with 250 /μg/ml of G418. Cell surface expression of A2.1/$K^b$ by the EA2 cell line was periodically verified by FACS analysis as described in Example 1A2b.

2) Jurkat Cells

Jurkat (American Tissue Culture Collection (ATCC) CRL 8163) is a human T cell leukemia cell line that does not express A2.1. Jurkat cells used as stimulator cells in the maintenance of peptide-specific CTL populations were stably transfected with the A2.1/$K^b$ chimeric gene (Irwin, et al., *J. Exp. Med*. 170: 1091 (1989)) as described above for the EL-4 cells, with the following modifications. During the transfection, the capacitors were charged to 1,450 mfd and during selection, the transfected cells were selected with 800 μg/ml G418.

e. Binding Inhibition Assay

In the binding inhibition assay, target cells displaying A2.1/$K^b$ were radiolabeled, incubated with test peptide and influenza A-specific peptide, and then assayed for binding of the influenza A-specific peptide to A2.1/$K^b$. Binding of the test peptide to A2.1/$K^b$ was determined by incubation with influenza A-specific CTL and assayed for lysis of the target cells in a cytotoxicity assay. Lysis of the target cells indicated that the A2.1/$K^b$ on the surface of the target cells had bound the peptide which corresponds to the peptide-specific CTL. Thus, the binding of test peptide to the target cells could be detected by the competitive inhibition of binding of the influenza A-specific peptide as evidenced by a decrease in the ability of the influenza A-specific CTL to lyse the target cells.

The A2.1/$K^b$-expressing EA2 cells (target cells) were radiolabeled by incubating $1.2 \times 10^6$ target cells with 150 μCi $^{51}$Cr (Na$^{51}$CrO$_4$; Amersham, Arlington Heights, Ill.) at 37° C. for 1.5 hours. During the labeling, target cells were also incubated in the presence of 10 μg p53-specific peptide (Table 2) and 0.1 μg influenza A-specific peptide. Unincorporated $^{51}$Cr and unbound peptide was removed by washing three times. The $^{51}$Cr-labeled target cells were resuspended in RPMI 10%.

Approximately $10^4$ $^{51}$Cr-labeled target cells were incubated with $3 \times 10^3$ influenza A-specific CTL (effector cells) to give a ratio of effector cells to target cells of 0.3 to 1 (E:T=0.3:1) in 200 μl of RPMI 10% in 96-well U-bottom microtiter plates (Costar, Cambridge, Mass.) for 6 hours at 37° C. Control reactions in which labeled target cells were incubated in the absence of effector cells were incubated in parallel to determine the amount of $^{51}$Cr which was spontaneously released during the incubation. The maximum amount of $^{51}$Cr released was determined by complete lysis of the cells with 5% (v/v) Tween-20. 100 μl of the supernatant was removed from each sample and the amount of $^{51}$Cr released during the incubation was determined by counting the samples in a gamma counter.

TABLE 2

| Influenza A-specific peptide (0.1 μg) | p53-specific peptide (10 μg) | SEQ ID NO of p53-specific peptide |
|---|---|---|
| +$^1$ | —$^2$ | |
| + | p53.25-35 | 1 |
| + | p53.65-73 | 2 |
| + | p53.149-157 | 3 |
| + | p53.264-272 | 4 |

TABLE 2-continued

| Influenza A-specific peptide (0.1 µg) | p53-specific peptide (10 µg) | SEQ ID NO of p53-specific peptide |
|---|---|---|
| + | HIV pol 510-518 | 5 |
| + | VSV N 52-59 | 7 |
| + | FLU NP 365-373 | 6 |

[1] "+" indicates that the given amount of this peptide was incubated with the target cells
[2] "—" indicates that this peptide was not added The percent specific lysis (%-SL) given in FIG. 1 for each of the p53-specific and control peptides was determined using the following formula: 100×(experimental−spontaneous release)/(maximum−spontaneous release)=percent specific lysis.

As indicated in FIG. 1, the influenza A-specific peptide—in the absence of exogenous p53-specific peptide and VSV N52-59 and FLU NP 365-373 peptides—gave comparable values and effected the highest percent specific lysis (%-SL). As noted above, VSV N52-59 and FLU NP 365-373 peptides are known to bind to $K^b$ and H-2$D^b$, respectively, but not to A2.1/$K^b$. It was therefore predicted that these peptides would not bind to A2.1/$K^b$, thereby allowing the influenza A-specific peptide to bind A2.1/$K^b$ and influenza A-mediated CTL lysis of the target cells to occur.

As also indicated in FIG. 1, the p53-derived and HIV pol peptides efficiently bound to A2.1/$K^b$. This is evidenced by the low efficiency with which the influenza A-specific CTL lysed the target cells.

3. Preparation and Maintenance of p53 Peptide-Specific CTL Cell Lines

A2.1/$K^b$ transgenic mice from Example 1A2a were immunized simultaneously with p53-specific and HBc-specific peptides. An HBc-specific peptide, derived from Hepatitis B virus core protein and comprising amino acid residue numbers 128 to 140 (TPPAYRPPNAPIL; SEQ ID NO 9), has been found to induce a CD4 T cell helper response (Sette, et al., *J. Immunol.* 153: (1994)).

Spleen cells were harvested and p53-specific peptide reactive CTL populations were recovered. The p53-specific peptide CTL populations were maintained by weekly restimulation with their respective p53-specific peptide presented on the surface of target cells in the presence of irradiated spleen cells and T cell growth factor (TCGF).

p53 peptide-specific CTL cell lines were prepared and maintained as follows. Each A2.1/$K^b$ transgenic mouse was immunized subcutaneously in the base of the tail with 100 µg p53-specific peptide and 120 µg HBc-specific peptide in 100 µl Incomplete Freund's Adjuvant (IFA).

A2.1/$K^b$ lipopolysaccharide (LPS)-blasts, to be used for in vitro restimulation of mouse-derived spleen cells, were prepared from unprimed A2.1/$K^b$ transgenic mice by suspending splenocytes in medium containing 25 µg/ml LPS and 7 µg/ml dextran sulfate. Cultures were established with 1.5×10$^6$ splenocytes/ml in a total volume of 30 ml and incubated at 37° C. for 72 hours in standing T75 flasks (Sette, et al., *J. Immunol.* 153, (1994)). Prior to restimulation, the LPS-blasts were incubated in the presence of 5 µg of a p53-specific peptide and 10 µg human β2-microglobulin (Calbiochem, La Jolla, Calif.) and irradiated (about 3,000 rad).

Murine spleen cells, collected 10 days after immunization, were restimulated in vitro with the irradiated A2.1/$K^b$ LPS-blasts which had bound the p53-specific peptide. The resultant p53-specific peptide CTL populations were maintained in vitro via weekly restimulation. Stimulator cells, EA2 cells expressing A2.1/$K^b$ (EA2/$K^b$), or Jurkat cells expressing A2.1/$K^b$ (JA2/$K^b$), were irradiated (about 20,000 rad), incubated with 15 µM of the p53-specific peptide for 1 hour at 37° C., and washed three times to remove unbound peptide. CTL populations were restimulated by incubation with the irradiated EA2/$K^b$ or JA2/$K^b$ stimulator cells with the bound p53-specific peptide at a concentration of 0.1-0.2×10$^8$ cells/well in the presence of irradiated (3,000 rad) C57/BL6 spleen cells in the presence of 2% (v/v) TCGF. TCGF was prepared by stimulating rat spleen cells with 5 µg con A for 2 days and then collecting the supernatant containing TCGF. Con A is inactivated by incubation of the supernatant with 1 gram/ml (gm/ml) α-methyl mannoside prior to incubation with the CTL populations.

CTL specific for p53 peptides p53.25-35, p53.65-73, p53.149-157, and p53.264-272 were generated using the methods described above and are designated CTL A2.1/$K^b$ 25, CTL A2.1/$K^b$ 65, CTL A2.1/$K^b$ 149, CTL A2.1/$K^b$ 264, respectively. CTL specific for the influenza A matrix peptide (M1 (55-66)) was generated by methods similar to those described above and in Vitiello, et al., Id. CTL specific for M1 (55-66) was designated "A clone 12" (which may be abbreviated "Clone 12").

B. p53-Specific Peptide CTL-Mediated Lysis of Target Cells

The sensitivity of target cells with either exogenously or endogenously derived p53 peptide bound to A2.1/$K^b$ on their surface to p53 peptide-specific CTL was evaluated in a cytotoxicity assay. The details are as follows.

1. p53-Specific Peptide CTL-Mediated Lysis of Target Cells with Exogenously Derived p53-Specific Peptide The sensitivity of target cells with p53-specific peptide bound to A2.1/$K^b$ on their surface to p53 peptide-specific CTL was evaluated by the standard $^{51}$Cr-release cytotoxicity assay as described in Example 1A2e. Briefly, target cells with p53-specific peptide bound to A2.1/$K^b$ on their surface were radiolabeled with $^{51}$Cr and incubated with peptide-specific CTL (effector cells). After incubation, the supernatant was assayed for the release of $^{51}$Cr from the labeled target cells. The release of $^{51}$Cr is correlated with lysis of the target cells and thus is an indication of the sensitivity of the target cells to lysis by the peptide-specific CTL.

EA2 cells transfected with A2.1/$K^b$ were incubated with 2 µg of the p53-specific peptides (p53.25-35, p53.65-73, p53.149-157, or p53.264-272) while being radiolabeled with $^{51}$Cr as described above in Example 1A2e. The p53-specific peptide-bearing radiolabeled EA2 cells (target cells) were then incubated in the presence of the corresponding p53-specific peptide CTL (effector cells) which had been prepared and maintained as described in Example 1A3.

Separate reactions comprising different ratios of effector to target cells (E:T) of 10:1, 3:1, 1:1, 0.3:1, 0.1:1, and 0.03:1 were prepared. The amount of $^{51}$Cr release was determined as described in Example 1A2e and is illustrated in FIGS. 2A through 2D, expressed as percent specific lysis plotted against the ratio of effector to target cells (E:T).

As can be seen in FIGS. 2A through 2D, CTL A2.1/$K^b$ 25, CTL A2.1/$K^b$ 65, CTL A2.1/$K^b$ 149, and CTL A2.1/$K^b$ 264 specifically lyse EA2.1/$K^b$ target cells to which the respective p53-derived peptide is bound. Target cells without bound p53 peptide are not specifically lysed by their respective CTL.

2. p53 Peptide-Specific CTL-Mediated Lysis of Target Cells With Endogenously Derived p53-Specific Peptide p53-peptide specific CTL were assayed for their ability to specifically lyse target cells which had been transfected with A2.1/$K^b$ and a gene expressing a mutant form of human p53

(Harlow, et al., *Mol. Cell. Biol.* 5: 1601 (1985)). Thus, the p53 peptides which are bound to the surface of the target cells by A2.1/K$^b$ are derived endogenously from the human mutant p53 gene and not exogenously by incubation with p53 peptides as described in Example 1B1.

The p53 gene product regulates the growth rate of cells. In tumor cells, the p53 gene generally contains one or more mutations in the encoded amino acid residue sequence and thus expresses a mutant form of human p53. Some mutant forms of human p53 affect the growth rate of cells. The EL-4 target cells were transfected with a mutant p53 gene rather than a wild-type p53 gene to prevent the transformed p53 from altering the growth rate of the transfected cells. In addition, tumor cells often express high levels of p53 and therefore have high levels of p53-derived peptides bound to HLA molecules and expressed on the cell surface.

The human mutant p53 gene expressed in the transfected target cells is processed into antigenic peptide fragments by intracellular processing of the protein and bound to A2.1/K$^b$ on the surface of the target cells. The presence of the human mutant p53-derived peptides bound to A2.1/K$^b$ on the surface of the target cells may be detected by incubation of the target cells with p53-specific peptide CTL. If the p53-derived peptide on the surface of the target cells is recognized by the p53-specific peptide CTL, lysis of the radiolabeled target cells will occur and be detected by the release of the radiolabel.

a. Preparation of Target Cells

1) Transfection of EA2 Cells with Human Mutant p53

EA2 target cells (EL-4 cells stably transfected with A2.1/K$^b$; see Example 1A2d1) were stably transfected with pC53-Cx4.2N3 according to the procedures described in Example 1A2d1. pC53-Cx4.2N3 encodes a human p53 gene containing a mutation in the nucleotide sequence encoding the amino acid residue at position 273 of the human p53 gene which alters the naturally-occurring arginine to a histidine (Harlow, et al., Id).

2) Transfection of Saos-2 Cells with Human Mutant p53

Saos-2 cells (ATCC HTB-85) are derived from human osteogenic sarcoma cells which have deletions of the p53 gene (Dittmer, et al., *Nature Gen.* 4: 42 (1993)) and naturally express A2 on their cell surface. Saos-2 cells were used as target cells in the standard $^{51}$Cr release cytotoxicity assays described herein to demonstrate peptide-specific CTL-mediated lysis of Saos-2 cells which display the peptide on their cell surface.

Saos-2 cells were stably transfected with a plasmid which expresses a human mutant p53 gene with an Arg -His mutation at amino acid residue 175 to produce a cell line identified herein as Saos-2/175 (Dittmer, et al., Id). The plasmid contains a mutation in the nucleotide sequence encoding the amino acid residue at position 175 of human p53 which alters the naturally-occurring arginine (Arg) amino acid residue to a histidine (His) amino acid residue.

The phenotype of the Saos-2 cells and stably transfected Saos-2/175 cells was verified periodically by FACS analysis as described in Example 1A2b. The expression of A2 was verified by reactivity with the A2-specific monoclonal antibody PA2.1 (ATCC HB 117). The expression of the human mutant p53 gene was verified by reactivity of immunoprecipitates of soluble cellular protein extracts with the PAb1801 monoclonal antibody (Oncogene Science, Uniondale, N.Y.) as described in Dittmer, et al., Id .

b. Cytotoxicity Assay to Detect Target Cell Lysis

The target cells EA2K$^b$ and EA2K$^b$.1 p53 (273) were assayed for the presence of endogenous p53 peptide on their surface by a cytotoxicity assay as described in Example 1A2e. The target cells were radiolabeled as described in Example 1A2e, but without the addition of exogenous p53 peptide. Target cells (T) were incubated with p53 peptide-specific effector cells (E) at E:T ratios of 60:1, 20:1, 6:1, 2:1, 0.6:1, and 0.2:1 (60, 20, 6, 2, 0.6, and 0.2). The effector cells assayed were CTL A2/K$^b$ 25, CTL A2/K$^b$ 65, CTL A2/K$^b$ 149, CTL A2/K$^b$ 264, and CTL CD8×A2/K$^b$ HIV pol 9K. Reactions were performed and the percent specific lysis determined as described in Example 1A2e.

The results are illustrated in FIGS. 3A through 3E as percent specific lysis (%-SL) by E:T ratio. A review of FIGS. 3A and 3B indicates that neither CTL A2K$^b$25 nor CTL A2K$^b$65 lysed target cells which express (EA2K$^b$.1 p53 (273)) or which do not express endogenous p53 (EA2K$^b$).

Next, the target cells EA2K$^b$ and EA2K$^b$.1 p53 (273) were incubated with exogenous p53.149-157 peptide during the labeling reaction (EA2K$^b$+p53.149-157 and EA2K$^b$.1 p53 (273)+p53.149-157) and incubated with CTL A2K$^b$ 149, CTL A2K$^b$ 264, and CTL CD8×A2K$^b$ HIV-pol 9K. The results are illustrated in FIGS. 3C through 3E as percent specific lysis (%-SL) plotted against the E:T ratio.

Figure 3A:
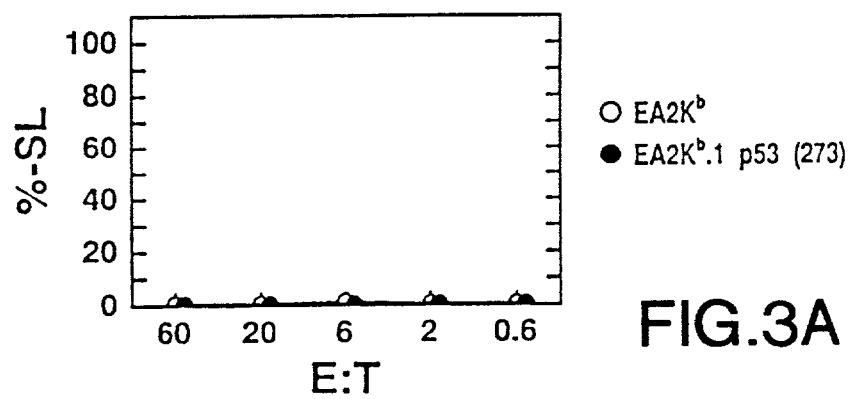
FIG. 3A illustrates lysis of target cells with CTL A2K$^b$ 25. The results of EA2K$^b$ (open circles) and EA2K$^b$ with A2/K$^b$- bound endogenous p53 peptides expressed from a human p53 gene with a mutation at amino acid residue 273 (EA2K$^b$.1 p53 (273); closed circle) are given.
Figure 3B:
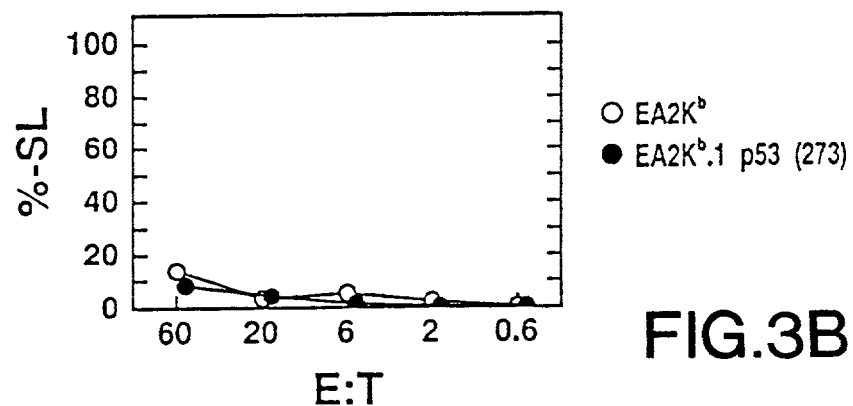
FIG. 3B illustrates lysis of target cells with CTL A2K$^b$ 65. The results of EA2K$^b$ (open circle) and EA2K$^b$.1 p53 (273) (closed circle) are given.
Figure 3C:
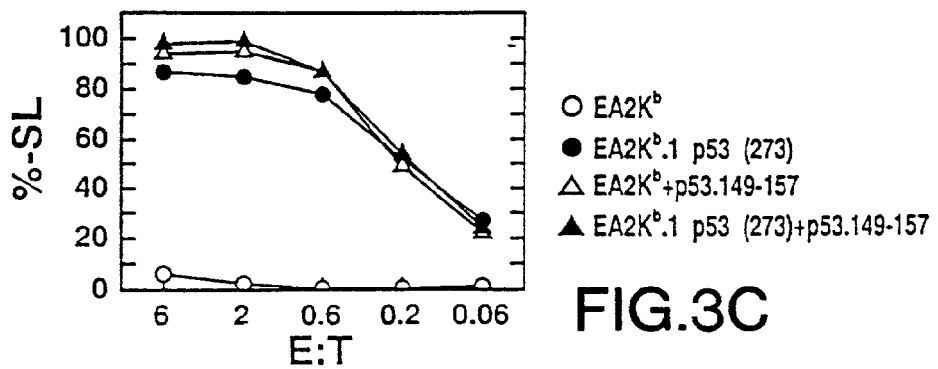
FIG. 3C illustrates lysis of target cells with CTL A2K$^b$ 149. The results of EA2K$^b$ (open circle), EA2K$^b$.1 p53 (273) (closed circle), p53 peptide p53.149-157 peptide bound to A2.1/K$^b$ on the surface of the EA2K$^b$ cells (EA2K$^b$+p53.149-157; open triangle), and EA2K$^b$.1 p53 (273) with p53 peptide p53.149-157 peptide bound to A2.1/K$^b$ on the surface of the EA2K$^b$.1p53 (273) (EA2K$^b$.1 p53 (273)+p53.149-157; closed triangle) cells are given.
Figure 3D:
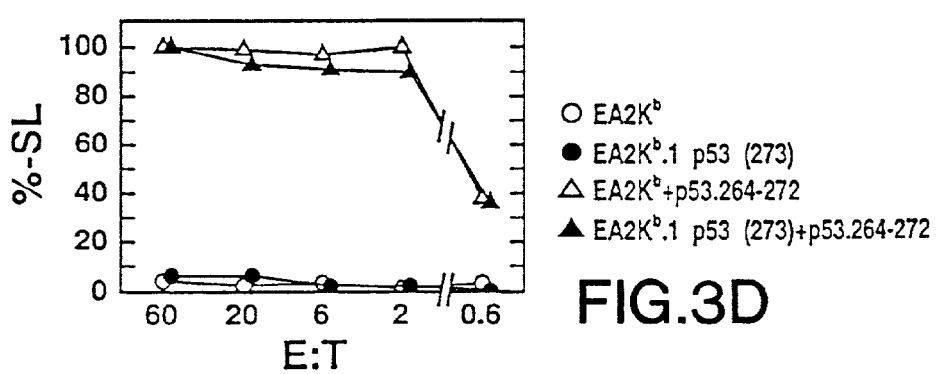
FIG. 3D illustrates lysis of target cells with CTL A2K$^b$ 264. The results of EA2K$^b$ (open circle), EA2K$^b$.1 p53 (273) (closed circle), p53 peptide p53.264-272 peptide bound to A2.1/K$^b$ on the surface of the EA2K$^b$ cells (EA2K$^b$+p53.264-272; open triangle), and EA2K$^b$.1 p53 (273) p53.264-272 peptide bound to A2.1/K$^b$ on the surface of the EA2K$^b$ cells (EA2K$^b$.1 p53 (273)+p53.264-272; closed triangle) are given.
Figure 3E:
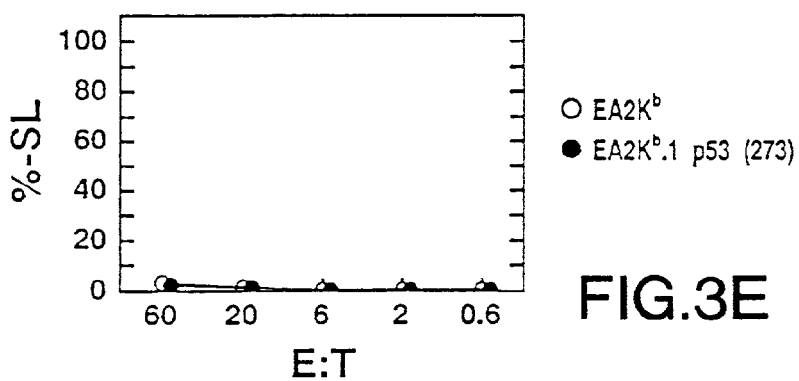
FIG. 3E illustrates lysis of target cells with CTL that were generated from transgenic mice immunized with the HIV pol 510-518 peptide (CTL CD8×A2K$^b$ HIV-pol). The results of EA2K$^b$ (open circle) and EA2K$^b$.1 p53 (273) (closed circle) are given.

The results illustrated in FIGS. 3C and 3D with CTL A2K$^b$ 149 and CTL A2K$^b$ 264, respectively, clearly demonstrate an increase in lysis of target cells expressing endogenous p53 (EA2K$^b$.1 p53 (273)) when compared with target cells which do not express p53 (EA2K$^b$). These effects are apparent at all E:T ratios examined, i.e., from an E:T ratio of 60:1 to one of 0.2:1. An increase in the lysis of target cells expressing endogenous p53 (EA2K$^b$.1 p53 (273)) when compared to target cells which do not express p53 (EA2K$^b$) is not apparent with CTL A2K$^b$ 149 and CTL A2K$^b$ 264. As illustrated in FIG. 3E, CTL CD8×A2K$^b$ HIV-pol 9K did not appear to lyse either of the target cells assayed (EA2K$^b$ and EA2K$^b$.1 p53 (273)).

c. Cytotoxicity Assay to Detect Target Cell Lysis

Target cells Saos-2 and Saos-2/175 were assayed for the presence of endogenous p53 peptide on their surface by a cytotoxicity assay as described in Example 1A2e. The target cells were radiolabeled as described, but without the addition of exogenous p53 peptide. Target cells (T) were incubated with p53 peptide-specific effector cells (E) at E:T ratios of 60:1, 20:1, 6:1, 2:1, 0.6:1, and 0.2:1 (60, 20, 6, 2, 0.6, and 0.2). The effector cells assayed were CTL A2/K$^b$ 25, CTL A2/K$^b$ 65, CTL A2/K$^b$ 149, CTL A2/K$^b$ 264, and CTL CD8×A2/K$^b$ HIV pol 9K. Reactions were performed and the percent specific lysis (%-SL) determined as described in Example 1A2e.

Figure 4A:
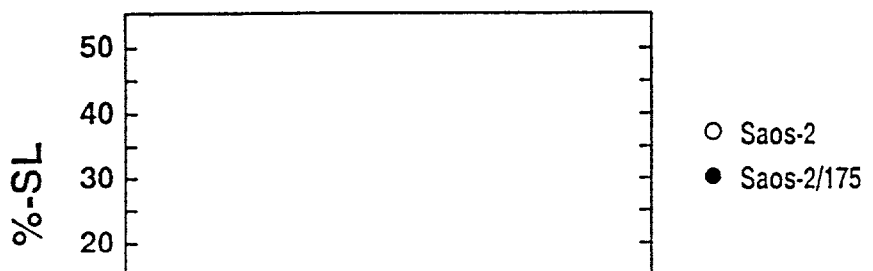
FIG. 4A illustrates lysis of target cells with CTL A2K$^b$ 25. The results using Saos-2 target cells alone (Saos-2; open circle) and Saos-2 target cells which express a human mutant p53 gene with a mutation at amino acid residue 175 (Saos-2/ 175; closed circle) are shown.
Figure 4B:
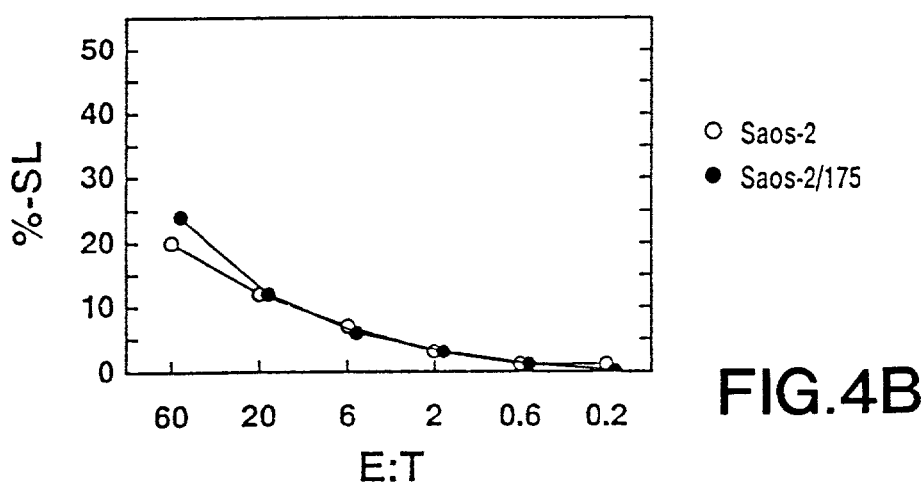
In FIG. 4B, lysis of target cells with CTL A2K$^b$ 65 is illustrated. The results using Saos-2 (open circle) and Saos-2/175 (closed circle) target cells are given.

Results of the foregoing assays are illustrated in FIGS. 4A through 4F. FIGS. 4A and 4B show that a very slight increase in lysis was seen with the CTL A2K$^b$ 25 effector cells, with a somewhat more moderate increase seen when CTL A2K$^b$ 65 effector cells were present.

Figure 4C:
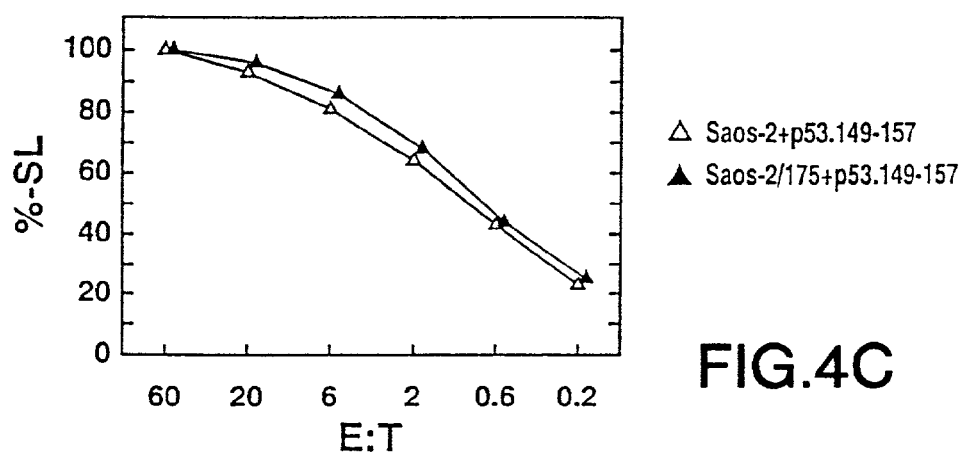
FIG. 4C illustrates lysis of target cells with CTL A2K$^b$ 149. The results obtained with Saos-2 (open triangle) and Saos-2/ 175 target cells with the p53.149-157 peptide bound to A2 on their cell surface (Saos-2/175+p53.149-157; closed triangle) are shown.

Next, the target cells Saos-2 and Saos-2/175 were incubated with exogenous p53.149-157 peptide during the labeling reaction (Saos-2+p53.149-157 and Saos-2/175+p53.149-157) and with CTL A2/K$^b$ 149. The results are illustrated in FIG. 4C as percent specific lysis plotted against the ratio of effector to target cells (E:T). Both populations of target cells were lysed in significant numbers, as shown.

Figure 4D:
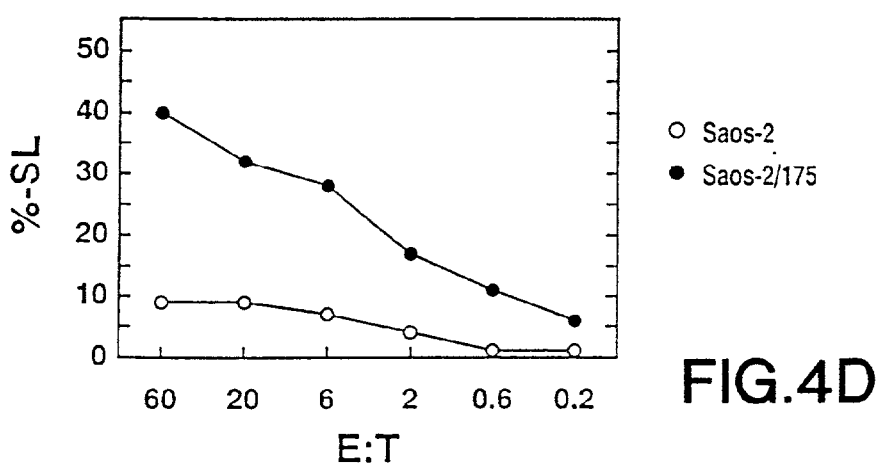
FIG. 4D illustrates lysis of target cells with CTL A2K$^b$ 149. The results of Saos-2 (open circle) and Saos-2/175 (closed circle) target cells are given.
Figure 4E:
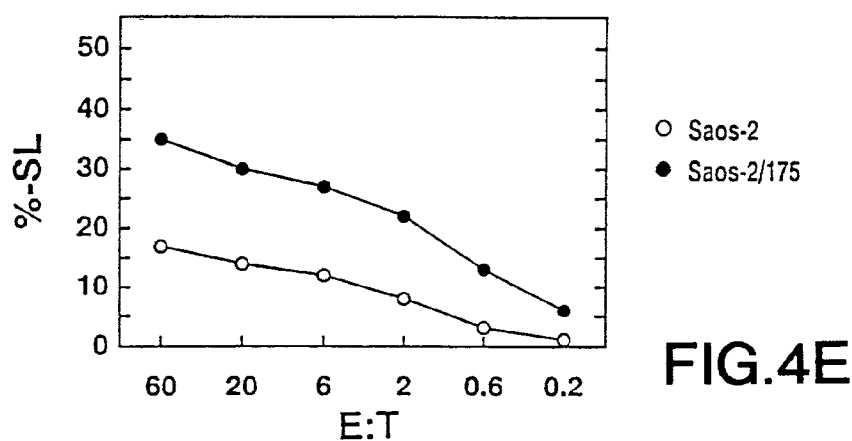
FIG. 4E illustrates lysis of target cells with CTL A2K$^b$ 264. The results of Saos-2 (open circle) and Saos-2/175 (closed circle) target cells are illustrated.

The results illustrated in FIGS. 4D and 4E with CTL A2/K$^b$ 149 and CTL A2/K$^b$ 264 effector cells, respectively, clearly demonstrate an increase in the number of target cells lysed which express endogenous p53 (Saos-2/175) when compared to target cells which do not express p53. This effect is apparent at all E:T ratios examined from E:T of 60:1 to 0.2:1. An increase in the number of target cells lysed which express endogenous p53 when compared to target cells which do not express p53 is not apparent with the remaining CTL examined. In addition, it is noted that target cells with and without expression of endogenous p53 which are incubated with exogenous p53.149-157 result in a higher percent specific lysis than target cells without exogenous p53.149-175.

Figure 4F:
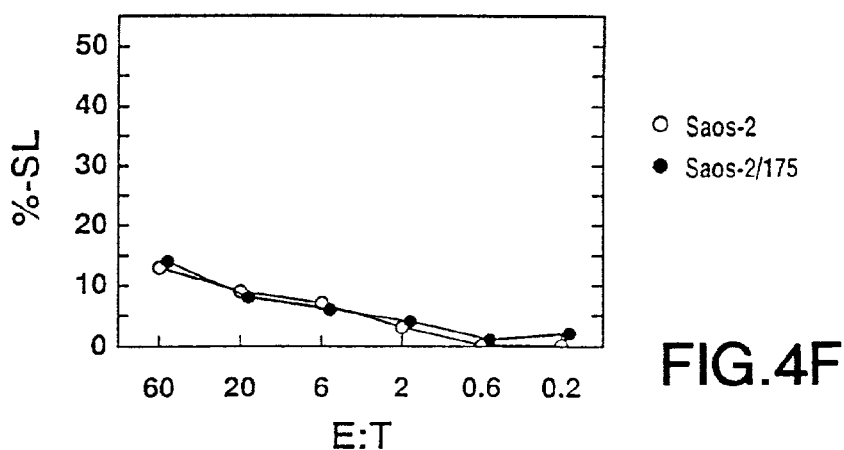
FIG. 4F illustrates lysis of target cells with CTL CD8×A2K$^b$ HIV-pol. The results of Saos-2 (open circle) and Saos-2/175 (closed circle) target cells are shown.

FIG. 4F illustrates lysis of target cells with CTL CD8× A2K$^b$ HIV-pol 9K; again, Saos-2 (open circle) and Saos-2/175 (closed circle) target cells are used. As shown in FIG. 4F, however, CTL CD8×A2K$^b$ HIV-pol 9K did not appear to induce significant lysis of either of the target cell populations assayed.

The foregoing results indicate that CTL populations capable of specifically lysing target cells which have either exogenous or endogenous p53 peptide bound to A2 on the cell surface can be generated by in vivo immunization with peptides derived from p53 which conform to a predetermined A2 binding motif. The specific lysis of these target cells by CTL populations can be demonstrated by comparing target cells which do or do not have exogenous or endogenous peptides. In addition, the presence or absence of a peptide bound to A2 on the cell surface can be demonstrated by the inhibition binding assays described herein.

Example 2

CTL-Mediated Lysis of Target Cells Expressing Her-2/Neu-Specific Peptides

A. CTL-Mediated Lysis of Target Cells with Bound Her-2/Neu-Derived Peptides

Her-2/Neu peptide-specific CTL were prepared by designing and synthesizing peptides derived from Her-2/Neu capable of being bound by HLA A2.1 molecules, immunizing A2KbxCD8 transgenic mice in vivo with Her-2/Neu peptides, and generating Her-2/Neu peptide-specific CTL cell lines derived from the immunized transgenic mice.

1. Preparation of Her-2/Neu Peptide Immunogens

Her-2/Neu-specific peptides were designed following the same motif described for the p53 peptides (see Example 1A1a) and are listed with their respective amino acid residue positions and SEQ ID NOS in Table 3. Her-2/Neu-specific peptides were synthesized and analyzed as described in Example 1A1b.

TABLE 3

| Peptide Designation | Amino Acid Residue Position | Amino Acid Residue Sequence | SEQ ID NO |
|---|---|---|---|
| HER-3 | 369-377 | KIFGSLAFL | 10 |
| HER-6 | 444-453 | TLQGLGISWL | 11 |
| HER-7 | 773-782 | VMAGVGSPYV | 12 |
| HER-8 | 546-555 | VLQGLPREYV | 13 |
| HER-9 | 661-669 | ILLVVVLGV | 14 |

2. Preparation of A2KbxCD8 Transgenic Mice

A2KbxCD8 transgenic mice were prepared by crossing an A2.1/K$^b$ transgenic mouse prepared as described in Example 1A2a with a transgenic mouse which expresses human CD8 (hCD8). The hCD8 transgenic mice were produced according to standard protocols (Hogan, et al., *Manipulating the Mouse Embryo: A Laboratory Manual*, Cold Spring Harbor Laboratory, Cold Spring Harbor, N.Y. (1986)). The transgene expression vector (p1013) contains the murine p56$^{lck}$ proximal promoter and either the full-length hCD8α or hCD8β cDNA sequence and modified by the polymerase chain reaction (PCR) amplification to add a BamHI restriction site, to facilitate insertion into the vector (Garvin et al., *Int. Immunol.* 2: 173-180 (1990)).

DNA fragments containing the nucleotide sequences encoding either hCD8α or hCD8β between two NotI restriction sites were microinjected either separately or together into C57BL/6×SJL)F2 embryos (Irwin, et al., *J. Exp. Med.* 170: 1091 (1989)) to generate lines with differential expression. Transgenic mouse lines were established by identifying mice that had integrated the transgenes as detected by tail DNA dot blot analysis (Sambrook, Id.). Transgenic founder mice were then backcrossed to C57BL/6 mice which have the H-2b haplotype. Five transgenic lines were selected based upon cell surface expression of hCD8 as determined by FACS analysis, as described below.

1) Detection of Cell Surface Expression of hCD8

Cell surface expression of hCD8 was determined by FACS analysis as described in Example 1A2b for the cell surface expression of A2.1 K$^b$. FITC-conjugated, phycoerythrin-conjugated and biotin-conjugated antibodies (Pharmingen, San Diego, Calif.) reactive with human CD8, murine CD8, and murine CD4 were used to stain cell suspensions from thymus and spleen derived from the transgenic mice. The overlapping emitted fluorescence from the three conjugated antibodies was compensated for according to the manufacturer's instructions. The stained cells were analyzed with a FACScan (Becton Dickinson; Mountain View, Calif.) instrument utilizing Lysis II software on total cell populations or on cells which stained positive with antibody against hCD8.

3. In Vitro Binding of Her-2/Neu Peptides to A2.1/K$^b$

The efficiency with which A2.1/K$^b$ bound the Her-2/Neu-derived peptides was determined in binding inhibition assays with an influenza A-derived peptide and influenza A peptide-specific CTL, as described in Example 1A2e for the p53-derived peptides.

EA2 target cells transfected with A2.1/K$^b$ and maintained as described in Example 1A2d1 were incubated with the exogenous Her-2/Neu-derived peptides listed in Table 3 (as described in Example 1A2e. The binding inhibition assay with influenza A-specific CTL, influenza A-specific peptide, and radiolabeled target cells with bound Her-2/Neu derived peptides was performed as described in Example 1A2e. The effector:target (E:T or E/T) cell ratios were 10:1, 3:1, 1:1, 0.3:1, and 0.1:1. Results of the binding inhibition assay are illustrated in FIG. 5 and are expressed as the percent specific lysis (alternatively expressed as % $^{51}$Cr released) plotted against the E/T ratio of influenza A-specific CTL clone 12.

Figure 5:
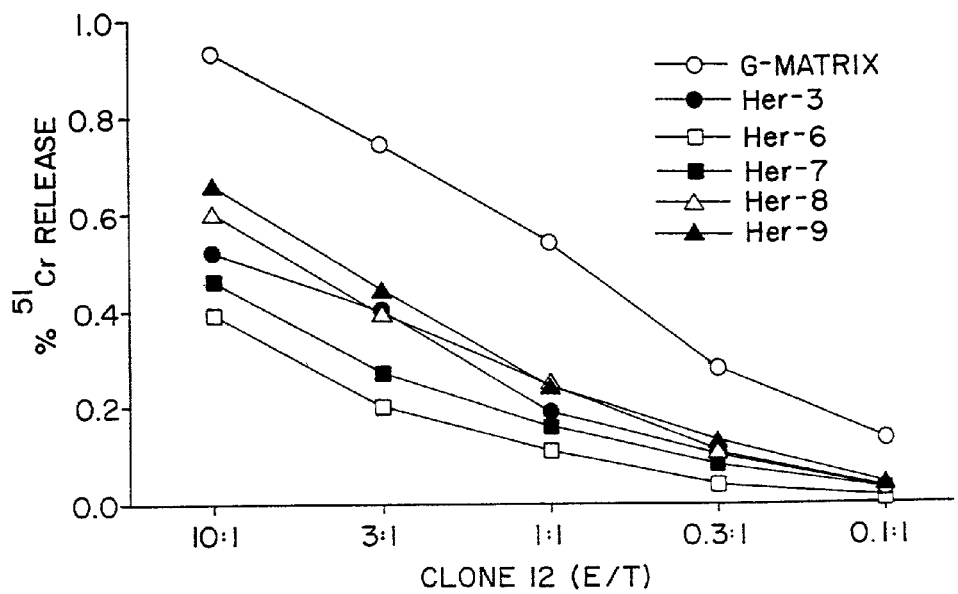
FIG. 5 illustrates CTL-mediated lysis of target cells which have specific peptides derived from Her-2/Neu bound to the cell surface as described in Example 2A3. The percent specific lysis (% $^{51}$Cr Release) is given on the Y-axis and the ratio of effector to target cells (Clone 12 (E/T)) is given on the X-axis. The CTL (Clone 12) was generated from transgenic mice immunized with the influenza G-matrix peptide (SEQ ID NO 8) as described in Example 1A2c. The G-matrix and M1(58-66) peptide have the same amino acid residue sequence. The results of the G-matrix peptide (G-MATRIX; open circle), Her-2/Neu peptides Her-3 (closed circle), Her-6 (open box), Her-7 (closed box), Her-8 (open triangle), and Her-9 (closed triangle) bound to A2.1/K$^b$ on the surface of the EA2K$^b$ target cells are given.

The results shown in FIG. 5 indicate that the influenza A-specific CTL were most effective at lysing target cells which had bound the influenza A-derived peptide (G-MATRIX, SEQ ID NO 8) to A2.1/K$^b$. The results also demonstrate that all of the Her-2/Neu-derived peptides tested inhibited the subsequent binding of the influenza A-derived peptide at approximately the same efficiency, with Her-9 binding at the highest efficiency.

These results illustrate that all of the Her-2/Neu peptides tested are capable of being bound by A2.1/K$^b$ on the surface of the EA2 target cells, as evidenced by their ability to inhibit binding of the influenza A-specific peptide to A2.1/K$^b$ the subsequent lysing of the target cells by the influenza A-specific CTL. The Her-2/Neu peptides tested were thereafter used to immunize transgenic mice, and Her-2/Neu peptide-specific CTL populations were prepared.

B. Her-2/Neu-Specific Peptide CTL-Mediated Lysis of Target Cells

1. Preparation of A2.1/$K^b$-Restricted Her-2/Neu Peptide-Specific CTL

CTL populations which are specific for Her-2/Neu-derived peptides were prepared and maintained following the methods described in Example 1A3 for the p53-derived peptides. The Her-2/Neu specific CTL populations were assayed for their ability to lyse target cells with the Her-2/Neu-specific peptide bound to A2.1/$K^b$ on the cell surface.

Figure 6:
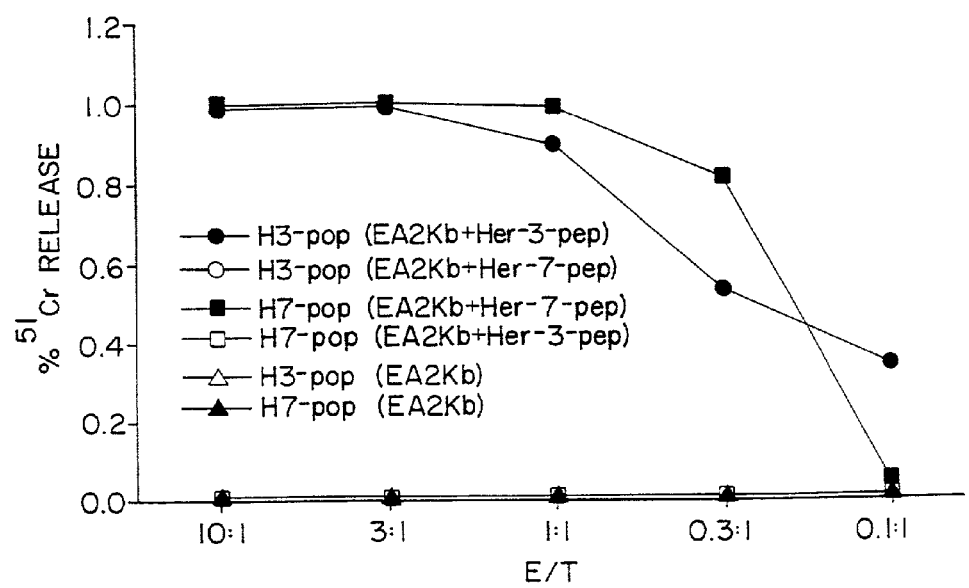
FIG. 6 illustrates CTL-mediated lysis of target cells which have specific peptides derived from Her-2/Neu bound to the cell surface as described in Example 2A3. The percent specific lysis (% $^{51}$Cr release) is given on the Y-axis and the ratio of effector to target cells (E/T) is given on the X-axis. The CTL-mediated lysis of target cells with CTL that were generated from transgenic mice (A2K$^b$×CD8) immunized with the either the Her-3 or Her-7 peptide (H3-pop and H7-pop, respectively) is illustrated. The results Her-3 bound to A2.1/ K$^b$ on the surface of the EA2K$^b$ cells (EA2K$^b$+Her-3-pep (closed circle) and EA2K$^b$+Her-7-pep (open circle), respectively), and EA2K$^b$ cells without peptide (EA2K$^b$; open triangle) are given. The results of Her-7 bound to A2.1/K$^b$ on the surface of the EA2K$^b$ cells (EA2K$^b$+Her-3-pep (closed square) and EA2K$^b$+Her-7-pep (open square), respectively), and EA2K$^b$ cells without peptide (EA2K$^b$; closed triangle) are given.

2. Her-2/Neu Peptide-Specific CTL-Mediated Lysis of Target Cells With Exogenously Derived Her-2/Neu Peptides The immunogenicity of each of the Her-2/Neu derived peptides was determined via the standard $^{51}$Cr release cytotoxicity assay, as described in Example 1A2e. The effector cells used in this assay were CTL derived from the A2$K^b$xCD8 transgenic mice which had been immunized with the Her-2/Neu derived peptides Her-3 and Her-7 (H-3 pop and H-7 pop, respectively; see above). The target cells were EA2$K^b$ with (EA2$K^b$+Her-3-pep and EA2$K^b$+Her-7-pep) and without (EA2$K^b$) exogenously added Her-3 or Her-7 peptide. Results of the assay for Her-3 and Her-7 are illustrated in FIG. 6 and are illustrated and are plotted as the % $^{51}$Cr released against the ratio of effector to target (E/T) cells.

Target cells which express A2.1/$K^b$ with exogenous Her-2/Neu peptide were efficiently lysed with the corresponding Her-2/Neu-specific CTL and not with the noncorresponding Her-2/Neu-specific CTL. Target cells which express A2.1/$K^b$ were not lysed by either the Her-3 or Her-7 peptide-specific CTL in these assays.

The Her-2/Neu-specific CTL were then tested for their ability to lyse target cells which were transfected with the Her-2/Neu gene and express peptides derived from the Her-2/Neu gene bound to A2.1/$K^b$ on the surface of the cells.

3. Her-2/Neu Peptide-Specific CTL-Mediated Lysis of Target Cells With Endogenously Derived Her-2/Neu Peptides The ability of Her-2/Neu peptide-specific CTL populations to lyse target cells which express the Her-2/Neu gene and thus display Her-2/Neu-derived peptides on their surface bound to A2.1/$K^b$ was assessed in the $^{51}$Cr release cytotoxicity assay.

EA2 target cells, transfected with the A2.1/$K^b$ gene, were also transfected with a plasmid encoding the Her-2/Neu gene (Di Fiore, et al., *Science* 237: 178 (1987)). Expression of the Her-2/Neu gene in EA2 cells provides a means for the endogenous processing and display of peptides derived from the Her-2/Neu gene bound to A2.1/$K^b$ on the surface of the EA2 cells.

Figure 7:
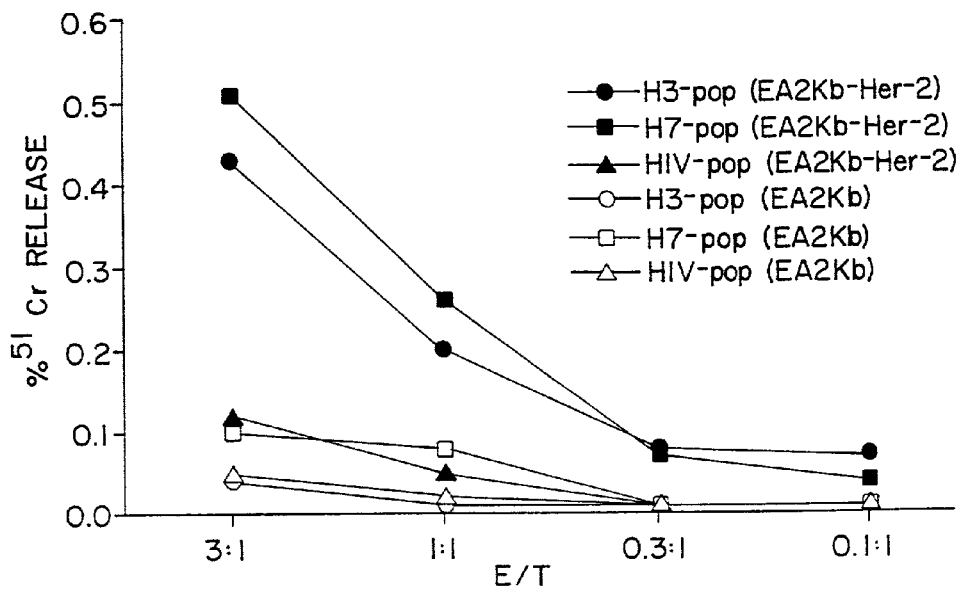
FIG. 7 illustrates CTL-mediated lysis of target cells which express endogenous Her-2/Neu specific peptides bound A2.1/ K$^b$ on the cell surface (EL4-A2K$^b$ Transfected With the Her-2/Neu Gene) as described in Example 2B2. The percent specific lysis (% $^{51}$Cr Release) is given on the Y-axis and the ratio of effector to target cells (E/T) is given on the X-axis. CTL were generated from transgenic mice (A2K$^b$×CD8) immunized with the an HIV-derived peptide (SEQ ID NO 5) (HIV-pop). The results of the Her3 (H3-pop) CTL-mediated lysis of target cells EA2K$^b$ (EA2K$^b$; open circle) and EA2K$^b$ with A2/K$^b$-bound endogenous Her-2/Neu peptides expressed from a Her-2/Neu gene (EA2K$^b$-Her-2; closed circle), Her7 (H7-pop) CTL-mediated lysis of target cells EA2K$^b$ (EA2K$^b$; open square) and EA2K$^b$ with A2/K$^b$-bound endogenous Her-2/Neu peptides (EA2K$^b$-Her-2; closed square), HIVpol (HIV-pop) CTL-mediated lysis of target cells $EA2K^b$ ($EA2K^b$; open triangle) and $EA2K^b$ with $A2/K^b$-bound endogenous Her-2/Neu peptides ($EA2K^b$-Her-2; closed triangle), are given.

The ability of CTL populations specific to the Her-3 and Her-7 peptides to lyse target cells expressing Her-2/Neu derived peptides on their surface was determined in the standard $^{51}$Cr release cytotoxicity assay described in Example 1A2e. The effector cells used in this assay were CTL derived from A2KbxCD8 transgenic mice immunized with the Her-3 and Her-7 peptides, as described in Example 1A3. The target cells were EA2$K^b$ with and without endogenously expressed and processed Her-2/Neu protein. The ratio of E:T was 10:1, 3:1, 1:1, 0.3:1, and 0.1:1. In addition, CTL which were specific to the HIV peptide, prepared as described in Example 1A3, were assayed. Results of the assay are shown in FIG. 7 and are described as the % $^{51}$Cr released plotted against the ratio of effector to target (E/T) cells.

The results of this experiment clearly demonstrate that the Her-3 and Her-7 specific CTL (H-3 and H-7 pop) efficiently lysed the target cells cotransfected with A2.1/$K^b$ and the Her-2/Neu gene (EA2$K^b$-Her-2). The specificity of the lysis of the cells by Her-2/Neu-specific CTL was demonstrated by the inefficient lysis of the cotransfected target cells by the HIV-specific CTL (HIV-pop). The ability of the CTL population to lyse the target cells is dependent on the display of the peptide bound to the A2.1/$K^b$ molecule as demonstrated by comparison between target cells which had been with the Her-2/Neu gene (EA2$K^b$-Her-2) and target cells which had not been transfected (EA2$K^b$).

Example 3

CTL-Mediated Lysis of Target Cells Expressing Her-2/Neu-Specific Peptides

A. Her-2/Neu Peptide-Specific CTL-Mediated Lysis of Breast Carcinoma Cells

The Her-2/Neu peptide-specific CTL prepared as described in Example 2B1 were then assayed for their ability to lyse breast carcinoma cell lines which express A2 and Her-2/Neu.

1. Preparation of Target Cells

The breast carcinoma cell lines MCF-7 (ATCC HTB 22), MDA 23.1 (ATCC HTB 26), and MDS 435 (ATCC HTB 129) were characterized phenotypically to determine if A2 was expressed on the cell by FACS analysis using the A2-specific monoclonal antibody PA2.1 (ATCC HB 1 17). MCF-7 and MDA 23.1 express A2 (and are thus designated A2$^+$) while MDS 435 does not express A2 (and is thus designated A2$^+$). In addition, the cell lines were characterized for cell surface expression of Her-2 by FACS analysis with c-Neu (AB-5) monoclonal antibody (Oncogene Science, Uniondale, N.Y.). The c-Neu antibody reacts with an epitope of Her-2/Neu on the cell surface and does not cross-react with the human EGF-receptor. All three cell lines express Her-2/Neu and are thus designated Her$^+$.

2. Cytotoxicity Assay to Detect Lysis of Target Cells by Her-2/Neu-Specific CTL

Her-2/Neu-specific CTL (effector cells) prepared and characterized for their ability to lyse target cells with Her-2/Neu specific peptide bound to A2.1/$K^b$ (see Example 2B2), and the breast carcinoma cell lines (target cells) described in Example 3A1 were used in a $^{51}$Cr release cytotoxicity assay to determine whether Her-2/Neu specific peptide CTL are able to kill target cells expressing peptides derived endogenously from Her-2/Neu protein bound to A2 on their cell surface. Procedures and results are described herein below.

a. Lysis of Breast Carcinoma Cell Lines by Her-3 and Her-7 Peptide-Specific CTL

The ability of the Her-3 and Her-7 peptide-specific CTL populations to lyse breast cell carcinoma cell lines which express Her-2/Neu-derived peptides on their surface was determined using the standard $^{51}$Cr release cytotoxicity assay described in Example 1A2e. The effector cells used in this assay were CTL derived from the A2KbxCD8 transgenic mice, which had been immunized with either the Her-3 or Her-7 peptide as described in Example 2B1. The target cells were the breast carcinoma cell lines (MCF-7, MDA 23.1, and MDA 435) which express Her-2/Neu peptides bound to A2 on their cell surface. The Her-2/Neu peptides were derived from Her-2/Neu protein endogenously expressed by the cell line. The MCF-7 and MDA 23.1 cell lines express A2, while the MDA 435 cell line does not. The ratios of E:T were 10:1, 3:1, 1:1, 0.3:1, and 0.1:1. Results of the Her-3 and Her-7 assays are given in FIG. 8 and are described as the percent $^{51}$Cr released (Y-axis) by the ratio of effector to target cells (X-axis).

Her-3 and Her-7 peptide-specific CTL populations (H-3 pop and H-7 pop, respectively) were shown to be effective at lysing target cells having peptides derived from the endogenous Her-2/Neu gene bound to A2 on their surface (see Example 2B2). The breast carcinoma cell lines MCF-7 and MDA 23.1 express A2 on the surface of their cells, while the cell line MDA 435 does not. The breast carcinoma cell lines express the Her-2/Neu epitope recognized by a monoclonal antibody on their cell surface (Example 3A1). The breast carcinoma cell lines MCF-7 and MDA 23.1 which express A2 and Her-2/Neu were efficiently lysed by H-3 and H-7 pop. The breast carcinoma cell line MDA 435 which expresses Her-2/Neu but does not express A2 was not lysed by H-3 and H-7 pop.

b. Effect of A2 Concentration and A2-Specific Antibody on Lysis of Breast Carcinoma Cell Lines by Her-7 Peptide-Specific CTL The level of cell surface expression of A2 was increased in the MDA 23.1 breast carcinoma cell line by incubation with γ-interferon prior to incubation with Her-7 specific CTL populations to determine the effect of A2 concentration on the ability of the CTL to lyse MDA 23.1 breast carcinoma cells. In addition, the effect of an antibody which specifically binds to A2 (PA2.1, ATCC HB 117) on the ability of the Her-7 specific CTL to lyse MDA 23.1 breast carcinoma cells was assessed.

The ability of an A2-specific antibody to inhibit Her-7 peptide specific CTL populations (effector cells) lysis of MDA 23.1 cells (target cells) which express Her-2/Neu-derived peptides bound to A2 on their surface was determined in the standard $^{51}$Cr release cytotoxicity assay as described in Example 1A3. Target cells were labeled with $^{51}$Cr as described in Example 1A3 and incubated for 24 hours in RPMI 10% with 100 ng/ml γ-interferon (R & D) to increase the concentration of A2 expressed on the surface of the target cells. Radiolabeled target cells incubated with γ-interferon were incubated with Her-7 specific or HIV pol CTL (Her2-7 CTL and HIV pol CTL, respectively) in the presence and absence 0.5 μg/ml of the A2 specific antibody (+anti-A2 (Her2-7 CTL) and +anti-A2 (HIVpol CTL)). The ratios of E:T were 30:1, 10:1, 3:1, and 1:1. Results of the increase in A2 concentration on the surface of target cells and incubation in the presence of A2 specific antibody on cell lysis by Her-7 specific CTL are given in FIG. 9 and are described as the percent specific lysis by the ratio of effector to target (E:T) cells.

Figure 9:
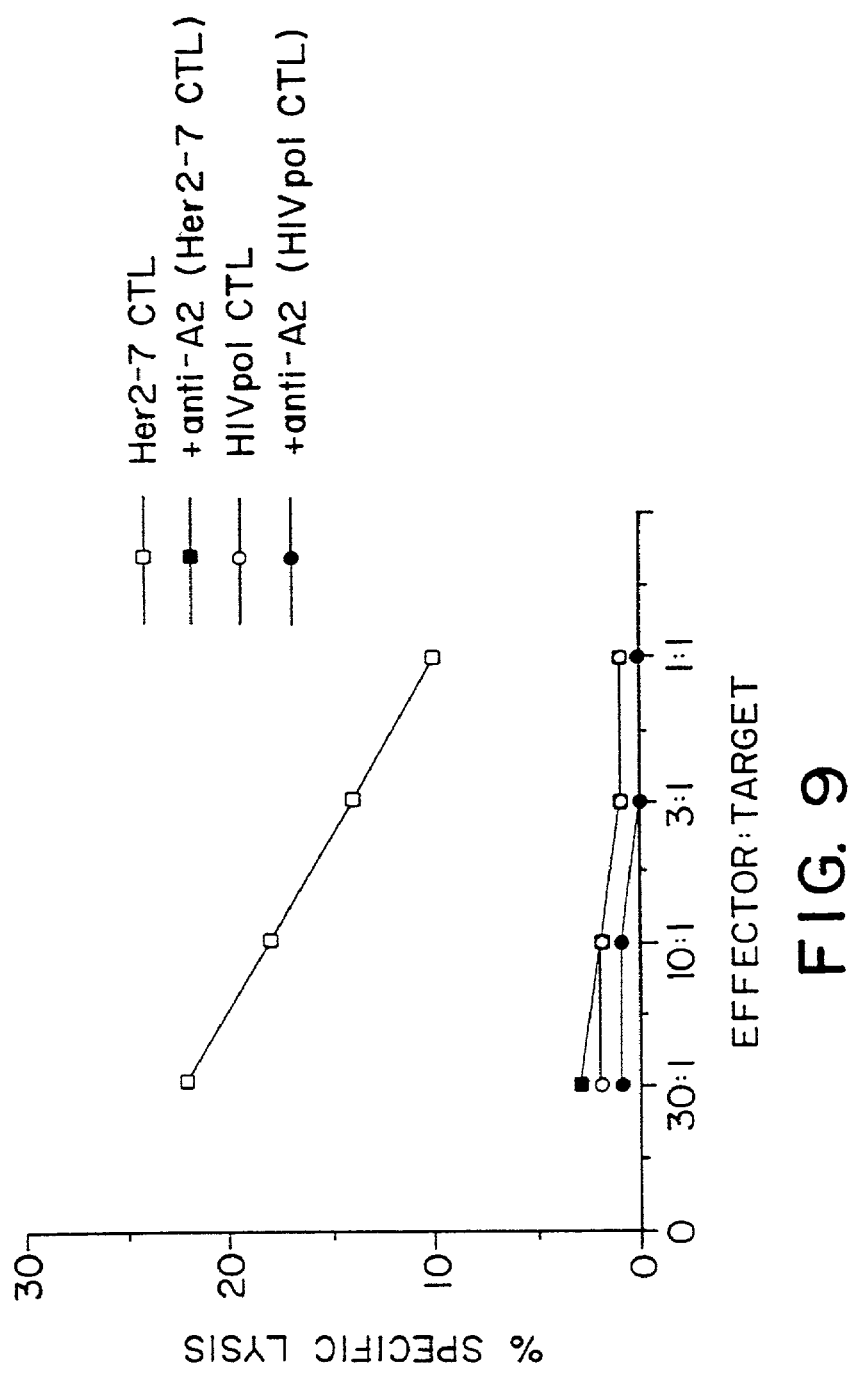
FIG. 9 illustrates the effect of A2 concentration and anti-A2 monoclonal antibody on the ability of Her-7 and HIV CTL-mediated lysis of the breast carcinoma cell line MDA-23.1 as described in Example 3. The percent specific lysis (%-SL) is given on the Y-axis and the ratio of effector to target cells (E:T) is given on the X-axis. The results of the Her-7 CTL-mediated lysis of target cells MDA 23.1 in the absence and presence of anti-A2 (Her2-7 CTL and +anti-A2 (Her2-7 CTL) (open square and closed square, respectively) and HIVpol CTL-mediated lysis of target cells MDA 23.1 in the absence and presence of anti-A2 (HIVpol CTL and +anti-A2 (HIVpol CTL) (open circle and closed circle, respectively) are given.

As illustrated in FIG. 9, incubation of target cells and CTL in the presence of the anti-A2 antibody (+anti-A2 (Her2-7 CTL) and absence of the anti-A2 antibody (Her2-7 CTL) significantly decreases the ability of the CTL to specifically lyse the target cells. In addition, the presence (+anti-A2 (HIVpol CTL) or absence (HIVpol CTL) of the anti-A2 antibody does not effect the ability of the HIV pol CTL to lyse the target cells.

Figure 8:
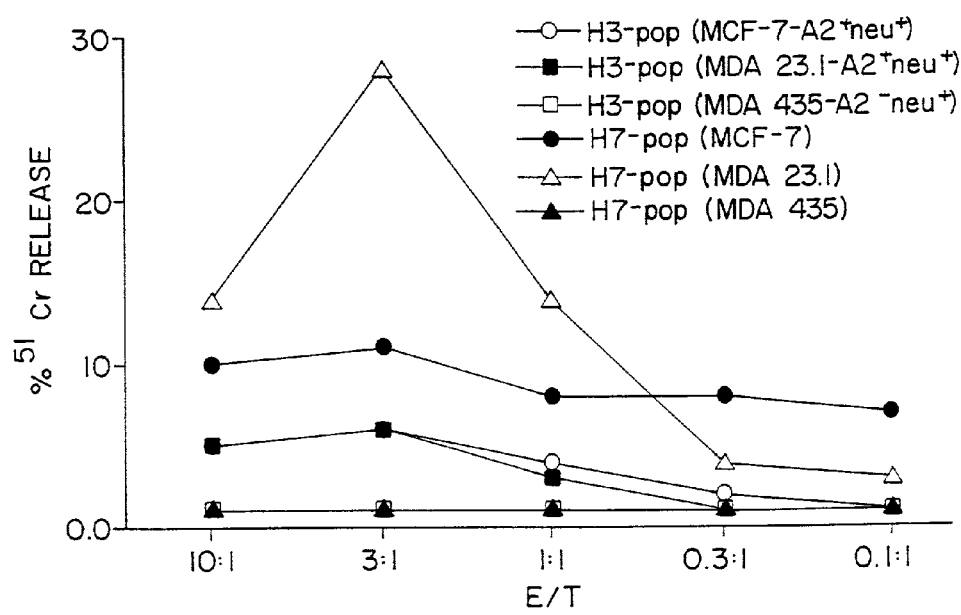
FIG. 8 illustrates Her-3, Her-7, and HIV CTL-mediated lysis of breast carcinoma cell lines as described in Example 3A2a. The percent specific lysis (% $^{51}$Cr Release) is given on the Y-axis and the ratio of effector to target cells (E/T) is given on the X-axis. The results of the Her-3 CTL-mediated lysis of target cells MCF-7, MDA 23.1, and MDA 435 (MCF-7-A2$^+$ Neu$^+$ (open circle), MDA 23.1-$^{A2+}$ Neu$^+$ (closed square), and MDA 435 A2$^+$ Neu$^+$ (open square)) and Her-7 CTL-mediated lysis of target cells MCF-7 (closed circle), MDA 23.1 (open triangle), and MDA 435 (closed triangle) which express a Her-2/Neu gene ($EA2K^b$-Her-2) are given.

A comparison of FIGS. 8 and 9 illustrates the effect of an increase in A2 concentration on the Her2-7 CTL-mediated lysis of target cells. The percent specific lysis of target cells is 28% with Her-2/Neu 7 CTL at a lower A2 concentration (FIG. 8, H7-pop (MDA 23.1), open triangle) and 14% at a higher A2 concentration (FIG. 9, H2-7 CTL, open square). Therefore, an increase in the A2 concentration results in an approximately 2-fold increase in the lysis of target cells.

Example 4

Targeting p53 as a General Tumor Antigen

The materials and methods used herein have been described in the foregoing Examples. By way of review, however, the transgenic (Tg) lines used in these studies (whose derivation has been described above) were as follows. The A2.1/K$^b$ Tg mice used herein were homozygous for both H-2b and the A2.1/K$^b$ transgene. All A2.1 Tg mice were homozygous for H-2b and heterozygous for the transgene. Mice were propagated and maintained in the vivarium at The Scripps Research Institute (La Jolla, Calif.). C57BL/6 mice were purchased from the breeding colony of The Scripps Research Institute.

Peptides were synthesized using a Gilson AMS 422 peptide synthesizer (Gilson, Middleton, Wis.), and purity was ascertained by reverse-phase HPLC analysis on a Vydac C18 column (Vydac, Hesperia, Calif.). Some peptides were also synthesized on an Applied Biosystems 430A synthesizer (Foster City, Calif.).

Previously-described transfectants utilized in these studies included EL4 A2 (EA2), EL4 A2/K$^b$ (EA2K$^b$), Jurkat A2 (JA2), Jurkat A2/K$^b$ (JA2K$^b$) (see Sherman, et al., *Science* 258: 815-181 (1992); Irwin, et al., *J. Exp. Med.* 170: 1091-1101 (1989)), Saos-2 and Saos-2 transfected with the human mutant p53 gene, Saos-2/175 (Dittmer, et al., *Nature Genet.* 42: 42-46(1993)). To obtain Ramos-A2 and T2-A2/K, 10 mg of plasmid containing genomic clones of A2.1 or A2/K$^b$ were cotransfected with pSV2neoDNA (2mg) as previously described (Irwin, et al., Id (1989)). T2 cells were obtained from Dr. Peter Cresswell; all other human cell lines were obtained from the American Type Culture Collection (ATCC) and tested by flow cytometry for the presence of HLA A2 (Irwin, et al., Id. (1989)).

High levels of p53 protein as a result of functionally homozygous mutations of the p53 gene were expressed by breast cancer cell lines MDA 231 and BT 549, the colorectal cancer cell line SW 480 and the Burkitt lymphoma cell line Ramos, whereas the breast cancer cell line MCF 7 accumulated wt-p53 protein in the cytoplasm via nuclear exclusion. (See Bartek, et al., *Oncogene* 5: 893-9 (1990); Nigro, et al., *Nature* 342: 705-8 (1989); Baker, et al., *Cancer Res.* 50: 7717-7722 (1990); Rodrigues, et al., *PNAS USA* 87: 7555-9 (1990); Gaidano, et al., *PNAS USA* 88: 5413-7 (1991); Takahashi, et al., *Mol. Carchinog.* 8: 58-66 (1993)). Both p53 alleles were deleted in the osteosarcoma cell line Saos-2 (Dittmer, et al., *Nature Genet.* 4: 42-46 (1993); Masuda, et al., *PNAS USA* 84: 7716-9 (1987); Hinds, et al., *Cell Growth Diff.* 1: 571-580 (1987)). Dendritic cells, concanavalin A (conA) and phytohemagglutinin (PHA)-activated lymphoblasts were prepared from peripheral blood mononuclear cells obtained from healthy, HLA A2.1 positive volunteer donors as described (Sallusto, et al., *J. Exp. Med.* 179: 1109-1118 (1994); Milner, *Nature* 310: 143-5 (1984)).

A. Peptide Binding to HLA-A2.1

A competition assay was used to assess binding of peptide to HLA-A2.1.

EA2 cells were pulsed with 1 mM of an A2-binding synthetic peptide representing residues 58-66 of the A/PR/8134 influenza virus matrix protein M1 and 100 mM of the indicated test peptide (Bednarek, et al., *J. Immunol.* 147: 4047-4053 (1991); Morrison, et al., *Eur. J. Immunol.* 22: 903-7 (1992)). The A2.1-binding peptide representing residues 476-484 of the reverse transcriptase of the human immunodeficiency virus type-1 (HIV-1) served as a positive control (Tsomides, et al., *PNAS USA* 88: 11276-80 (1991)). Both a H-2K$^b$-binding synthetic peptide representing residues 52-59 of the vesicular stomatitis virus nucleoprotein (VSV-N 52-59) and a H-2Db-binding synthetic peptide representing residues 366-374 of the influenza A virus (1934) nucleoprotein (Flu NP 1934 366-374) served as negative controls (Van- Bleek and Nathenson, *Nature* 348: 213-6 (1990); Rotzschke, et al., *Nature* 348: 252-4 (1990); Falk, et al., *J. Exp. Med.* 174: 425-434 (1991)). The A2.1-restricted, M1-specific CTL clone 12 (A clone 12) was assayed at various effector-to-target (E:T) ratios for lytic activity against peptide-and non-peptide-pulsed EA2 targets in a 4-hour $^{51}$Cr release assay (Irwin, et al., Id (1989)). Percent inhibition of A clone 12 mediated lysis of M1-pulsed EA2 targets by the indicated peptides was calculated at an E:T ratio of 0.3:1.

B. Peptide Priming of HLA Transgenic Mice and Propagation of CTL Lines

Mice were injected subcutaneously at the base of the tail with 100 mg of the indicated test peptide and 120 mg of the I-Ab-binding synthetic T helper peptide representing residues 128-140 of the hepatitis B virus core protein (Sette, et al., *J. Immunol.* 1534: 5586-5592 (1994)) emulsified in 100 ml incomplete Freunds adjuvant (IFA). After 10 days, spleen cells of primed mice were cultured with irradiated A2.1/$K^b$ or A2.1-Tg lipopolysaccharide (LPS) activated spleen cell stimulators that had been pulsed with the indicated priming peptide at 5 mg/ml and human β2-microglobulin at 10 mg/ml (Sherman, et al., *Science* 258: 815-818 (1992); Vitiello, et al., *J. Exp. Med.* 173: 1007-1015 (1991)). After 6 days, the resultant effector cells were assayed in a 4-hour $^{51}$Cr release assay at various E:T ratios for lytic activity against T2 or T2A2$K^b$ that had been pulsed with either the indicated priming peptide, an unrelated A2.1-binding peptide, or no peptide. Polyclonal CTL lines specific for hu-p53.149-157 (CTL A2/$K^b$ 149 and A2 149) and hu-p53.264-272 (CTL A2/$K^b$ 264 and A2 264) were established by weekly restimulation of effector CTL with irradiated JA2$K^b$ or JA2 cells that had been pulsed with 5 mg of the indicated p53 peptide, irradiated C57BL/6 spleen filler cells and 2% (vol/vol) T cell growth factor.

C. Results and Discussion

Synthetic peptides representing sequences within the hu-p53 protein were selected according to the known consensus motifs for peptides bound by A2.1. (See, e.g., Falk, et al., *Nature* 351: 290-6 (1991); Hunt, et al., *Science* 255: 1261-3 (1992); Parker, et al., *J. Immunol.* 149: 3580-7 (1992); Ruppert, et al., *Cell* 74: 929-937 (1993); Kast, et al., *J. Immunol.* 152: 3904-3912 (1994); Kubo, et al., *J. Immunol.* 152: 3913-3924 (1994); Zeh, et al., *Human Immunol.* 39: 79-86 (1994); Stuber, et al., *Eur. J. Immunol.* 24: 765-8 (1994).) Selected wt-p53 peptides were 8 to 11 amino acids in length and had at their N-terminal position either L, M, I, V, A or T (as given in single-letter code) and at their C-terminus either V, L, I, A, M, T, S or Q.

A2.1-binding was determined by a competition assay that assessed the ability of each peptide to inhibit binding of a synthetic peptide representing residues 58-66 of the A/PRI8134 (PR8) influenza virus matrix protein M1 (58-66) (Bednarek, et al., *J. Immunol.* 147: 4047-4053 (1991); Morrison, et al., *Eur. J. Immunol.* 22: 903-7 (1992)) to A2.1 on target cells (Table 4). Inhibition of M1 peptide-binding was monitored as a decrease in target cell lysis using a M1-specific, A2.1-restricted CTL clone, clone 12.

All 19 peptides with intermediate-to-high A2.1-binding activity (>23% inhibition of A2.1-binding of M1) and 3 peptides with low (10% to 22% inhibition) or no A2.1-binding activity (<10% inhibition) were tested for their immunogenicity in A2.1/$K^b$-Tg mice. Mice were primed with peptide and 10 days later, spleen cells from these mice were restimulated with peptide in vitro and tested for an A2.1/$K^b$-restricted, peptide-specific CTL response. As reported, A2.1/$K^b$-Tg mice could mount an A2.1/$K^b$-restricted CTL response specific for known A2.1-binding CTL epitopes, such as HIV-1 RT (476-484) (Table 4). (See also Sherman, et al., *Science* 258: 815-8 (1992); Vitiello, et al., *J. Exp. Med.* 173: 1007-1015 (1991); Engelhard, et al., *J. Immun.* 146: 1226-1232 (1991); Sette, et al., *J. Immunol.* 153: 5586-5592 (1994).)

Table 4 illustrates the A2.1-binding affinity and immunogenicity of various wt-p53 peptides. Selected wt-p53 peptides were synthesized and their relative A2.1-binding affinity was determined by measuring their ability to inhibit the A2.1-binding of the M1 (58-66) peptide. The immunogenicity of wt-p53 peptides and the HIV-1 RT 476-484 control peptide was determined by peptide-priming of A2.1/$K^b$-Tg mice. Two mg of peptide was used to pulse T2A2/$K^b$ targets during $^{51}$Cr labeling. Lytic activity of CTL at an E:T ratio of 60:1 was calculated as previously described (Irwin, et al., Id (1989)). Lysis of T2A2/$K^b$ pulsed with an unrelated A2.1-binding peptide was similar to that obtained for nonpeptide-pulsed T2A2/$K^b$ and did not exceed 15%. The data represent the highest amount of lytic activity obtained after peptide-priming of at least three individual mice. Residues that are homologous between hu- and mur-wt-p53 are displayed in bold type. Amino acid residues are given in single-letter code. ND denotes not determined.

TABLE 4

| Peptide | Sequence | SEQ ID NO | (%) | Lytic Activity by Peptide-Specific CTL After Priming of A2.1/$K^b$-Tg Mice[a] |
|---|---|---|---|---|
| hu-wt-p53: | | | | |
| 25-33 | LLPENNVLS | 1 | 42 | 3 |
| 25-35 | LLPENNVLSPL | 1 | 65 | 47 |
| 31-39 | VLSPLPSQA | 15(res.1-9) | 38 | 3 |
| 31-40 | VLSPLPSQAM | 15 | 23 | 0 |
| 42-50 | DLMLSPDDI | 16 | 19 | 0 |
| 43-52 | LMLSPDDIEQ | 17 | 25 | 3 |
| 65-73 | RMPEAAPPV | 2 | 62 | 85 |
| 69-76 | AAPPVAPA | 18(res.1-8) | 46 | 0 |
| 69-78 | AAPPVAPAPA | 18(res.1-10) | 41 | 0 |
| 69-79 | AAPPVAPAPAA | 18 | 4 | 0 |
| 73-81 | VAPAPAAPT | 19 | 12 | 0 |
| 78-86 | AAPTPAAPA | 20 | 51 | 0 |
| 110-119 | RLGILHSGTA | 21 | 10 | ND |
| 117-125 | GTAKSVTCT | 22 | 12 | ND |
| 121-129 | SVTCTYSPA | 23 | 8 | ND |
| 122-130 | VTCTYSPAL | 24 | 12 | ND |
| 129-137 | ALNKMFCQL | 25 | 71 | 0 |
| 136-144 | QLAKTCPVQ | 26 | 15 | ND |
| 146-155 | WVDSTPPPGT | 27 | 10 | ND |
| 149-157 | STPPPGTRV | 3 | 29 | 91 |
| 161-169 | AIYKQSQHM | 28 | 12 | ND |
| 187-195 | GLAPPQHLI | 29(res.1-9) | 62 | 1 |
| 187-197 | GLAPPQHLIRV | 29 | 14 | ND |
| 210-218 | NTFRHSVVV | 30 | 43 | 6 |
| 229-237 | CTTIHYNYM | 31 | 14 | ND |
| 255-264 | ITLEDSSGNL | 32(res.1-10) | 24 | 3 |
| 255-265 | ITLEDSSGNLL | 32 | 22 | ND |
| 263-272 | NLLGRNSFEV | 33 | 50 | 3 |
| 264-272 | LLGRNSFEV | 4 | 60 | 94 |
| 322-330 | PLDGEYFTL | 34 | 24 | 0 |
| 339-247 | EMFRELNEA | 35 | 12 | ND |
| mur-wt-p53: 261-269 | LLGRDSFEV | 36 | 75 | 10 |
| HIV-1 RT: 476-484 | ILKEPVHGV | 5 | 72 | 85 |
| VSV-N: 52-59 | RGYVYQGL | 6 | 4 | ND |
| Flu NP 1934: 366-374 | ASNENMETM | 7 | 4 | ND |

[a][Specific $^{51}$Cr release (%)]

A2.1/$K^b$-restricted CTL responses specific for hu-p53.25-35, 65-73, 149-157 and 264-272 were also detectable. The peptide specificity of these responses was evidenced by the ability of CTL to lyse cells pulsed with the immunizing peptide, but not other A2.1-binding peptides (see, e.g., FIGS. 10A and 10C).

Figure 10A:
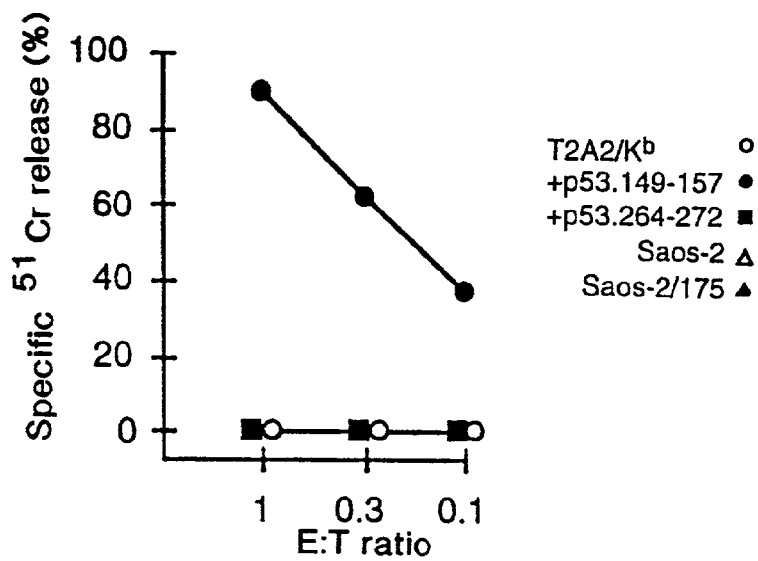
FIGS. 10A-H illustrate A2.1-restricted recognition of endogenously synthesized p53 epitopes by p53-specific CTL from A2.1/$K^b$-Tg and A2.1-Tg mice. Effector CTL were generated by peptide-priming of Tg mice.
Figure 10B:
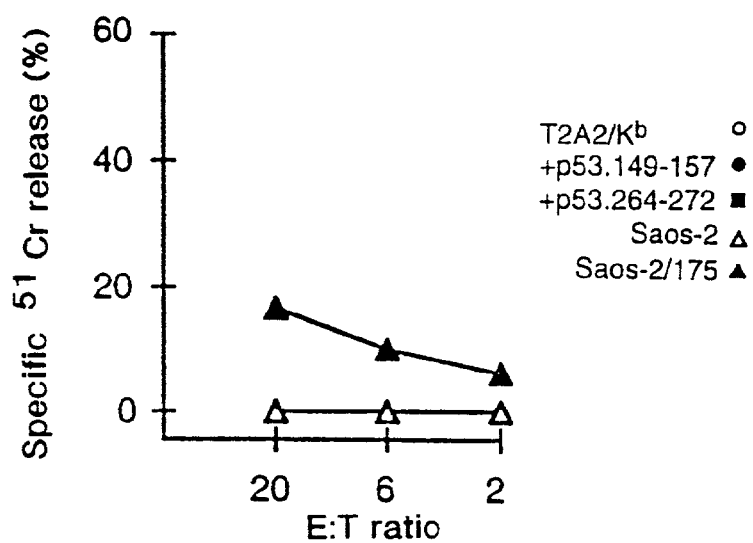
Figure 10C:
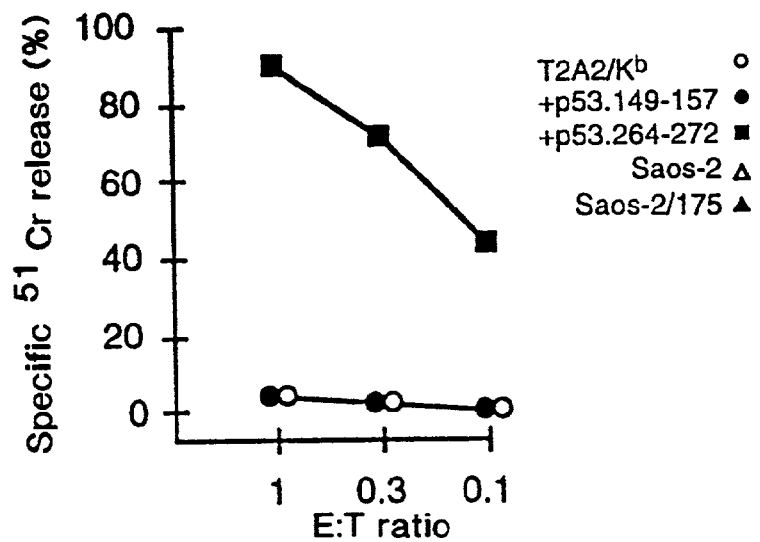
Figure 10D:
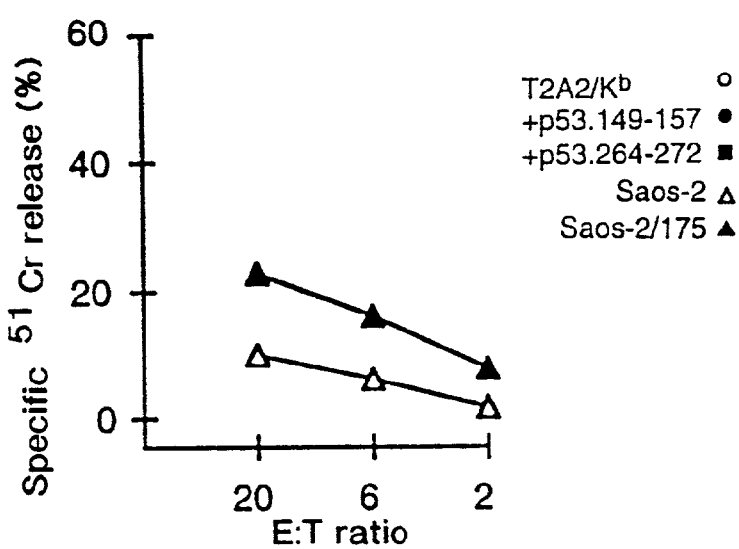
Figure 10E:
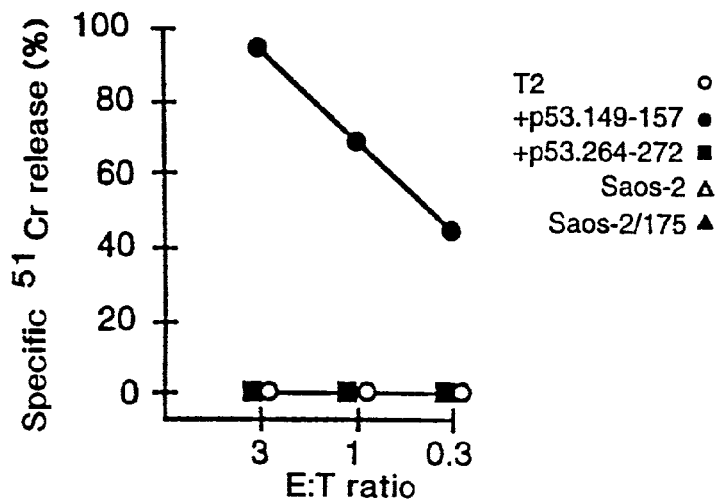

FIGS. 10A-H illustrate A2.1-restricted recognition of endogenously synthesized p53 epitopes by p53-specific CTL from A2.1/$K^b$-Tg and A2.1-Tg mice. Effector CTL were generated by peptide-priming of Tg mice. In FIGS. 10A and B, the CTL cell lines were A2$K^b$149-primed; in FIGS. 10C and D, the CTLs were primed with A2$K^b$264. In FIGS. 10E and F, the CTL cell lines were A2 149-primed; 10G and H, the CTLs were primed with A2 264. In FIGS. 10A-H, effector:target (E:T) ratios were plotted against specific $^{51}$Cr release (%).

CTL were assayed for cytotoxicity in a 5-hour $^{51}$Cr release assay against the indicated targets: FIGS. 10A and C: T2A2/$K^b$ (open circles, ○) or T2A2/$K^b$ pulsed with p53.149-157 (closed circles, ●) or p53.264-272 (closed squares, ■). FIGS. 10E and G: T2 (0) or T2 pulsed with p53.149-157 (●) or p53.264-272 (■). FIGS. 10B, D, F, H: Saos-2 (open triangles, △) or the same cells transfected with the human p53 gene, Saos-2/175 (closed triangles, ▲). (See, e.g., Dittmer, et al., *Nature Genet*. 4: 42-6 (1993); Masuda, et al., *PNAS USA* 84: 7716-9 (1987); Hinds, et al., *Cell Growth Diff*. 1: 571-580 (1990).) Both lines expressed similar levels of A2.1 as detected by flow cytometry. (See, e.g., Irwin, et al., *J. Exp. Med*. 170: 1091-1101 (1989).)

These findings were consistent with the hypothesis that the majority of functional TCR epitopes is produced by peptides with high affinity (as with hu-p53.25-35, 65-73 and 264-272) and intermediate affinity (as with hu-p53.149-157) for the presenting MHC class I molecule (Sette, et al., Id. (1994)). However, the data also suggested that gaps in the functional T cell repertoire may exist as not all of the nonhomologous hu-p53 peptides with high A2.1-binding activity were capable of inducing a CTL response. No significant response by A2.1/$K^b$-Tg mice was detectable against mur-p53.261-269 that shared homology with hu-p53.264-272 at all but one amino acid residue, yet this murine peptide had the highest A2.1-binding activity of all p53 peptides tested (Table 4).

A lack of CTL responsiveness by A2.1/$K^b$-Tg mice was also observed with hu-p53 peptides that were homologous to mur-p53 sequences and had either high (hu-p53.187-195) or intermediate (hu-p53.255-264 and 322-330) binding activity for A2.1. These results suggested that tolerance to self-p53 epitopes may indeed limit the repertoire of responsive T cells.

Several peptides identified in this study had been previously shown to bind A2.1 and also elicit a peptide-specific response by human peripheral blood lymphocytes. (See Zeh, et al., *Human Immunol*. 39: 79-86 (1994); Stuber, et al., *Eur. J. Immunol*. 24: 765-8; Houbiers, et al., *Eur. J. Immunol*. 23: 2072-7 (1993); Nijman, et al., *J. Immunother*. 14: 121-6 (1993); Nijman, et al., *Immunol. Letters* 40: 171-8 (1994).) However, the ability of such CTL to recognize cells endogenously expressing p53 had not been reported, thereby leaving unresolved the issue of whether these or other p53 peptides are presented in association with MHC on the cell surface.

In order to determine if the peptides corresponding to these sequences were actually endogenously processed and presented in association with A2.1 molecules on the surface of human tumor cells expressing hu-p53, peptide-specific polyclonal CTL lines from A2.1/$K^b$-Tg mice were established and tested for recognition of the A2.1 expressing, p53-deficient cell line, Saos-2, and this same line transfected with a hu-p53 gene, Saos-2/175 (Dittmer, et al., *Nature Genet*. 4: 42-6 (1993); Masuda, et al., *PNAS USA* 84: 7716-9 (1987); Hinds, et al., *Cell Growth Diff*. 1: 571-580 (1990)). Comparison of the levels of lysis of the transfectant relative to the p53-deficient parental line indicated that CTL specific for hu-p53.25-35 and 65-73 did not lyse Saos-2/175, suggesting these peptides were not processed and presented in sufficient amount for recognition by these CTL lines (data not shown). In contrast, CTL specific for hu-p53.149-157 and 264-272 were presented by cells that endogenously expressed high levels of hu-p53 (FIGS. 10B, D).

However, attempts to obtain recognition by these CTL lines of A2.1-expressing tumors that naturally expressed high levels of hu-p53 were unsuccessful, even after pretreatment of target cells with both interferon-gamma (IFN-γ) and tumor necrosis factor-a (TNF-α) (data not shown), a method that is known to augment specific cell lysis by increasing both the numbers of MHC-peptide complexes and adhesion molecules expressed on the cell surface (Fisk, et al., *Lympho. & Cytokine Res*. 13: 125-131 (1994); Fady, et al., *Cancer Immunol. Immunother*. 37: 329-336 (1993)). This suggested tumor cell lines may not present p53 peptides, or more likely, that they expressed insufficient levels of the p53 peptides to be recognized by these particular CTL lines.

It should be noted that due to the inability of murine CD8 to interact with the alpha-3 domain of the human A2.1 molecule, CTL from A2.1/$K^b$ Tg mice are at a disadvantage in recognition of cells expressing A2.1 as compared with A2.1/$K^b$ (Sherman, et al., Id. (1992); Vitiello, et al., Id. (1991); Engelhard, et al., Id. (1991); Irwin, et al., Id (1989)). However, A2.1 restricted CTL from A2.1-Tg mice appear to be CD8 independent in their recognition of target cells, presumably due to their selection and stimulation in the absence of the participation of murine CD8 (Sherman, et al., Id (1992)). Previous experiments indicated CD8 independent CTL require less peptide antigen for target cell recognition (Alexander, et al., *J. Exp. Med*. 173: 849-858 (1991)). Therefore, if p53-specific CTL derived from A2.1/$K^b$ Tg mice were unable to lyse human tumor cells due to presentation of limiting numbers of the relevant peptide-MHC complexes, it was possible that A2.1-transgenics could provide peptide-specific CTL capable of detecting the low amounts of p53 peptides expressed by tumor cells.

Figure 10F:
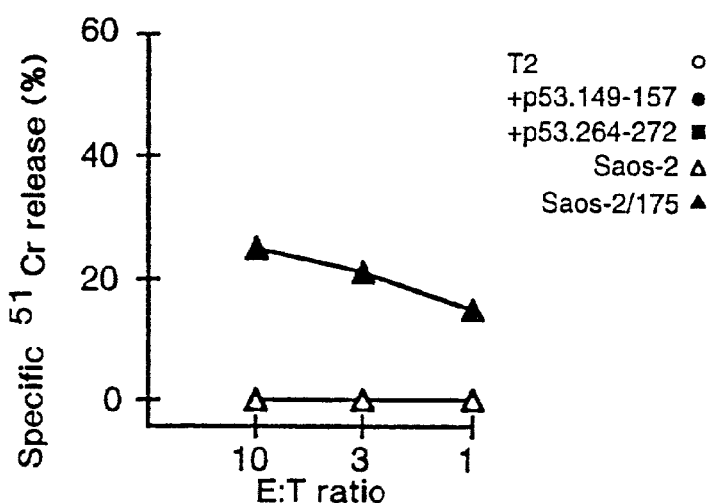
Figure 10G:
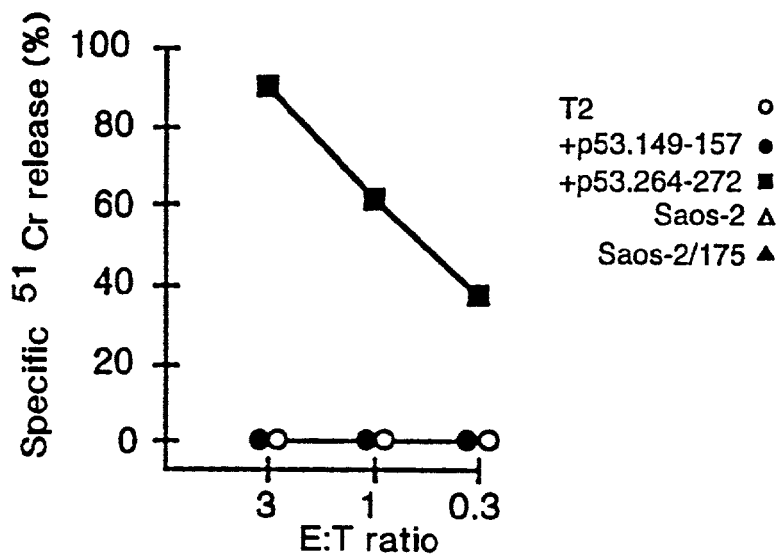
Figure 10H:
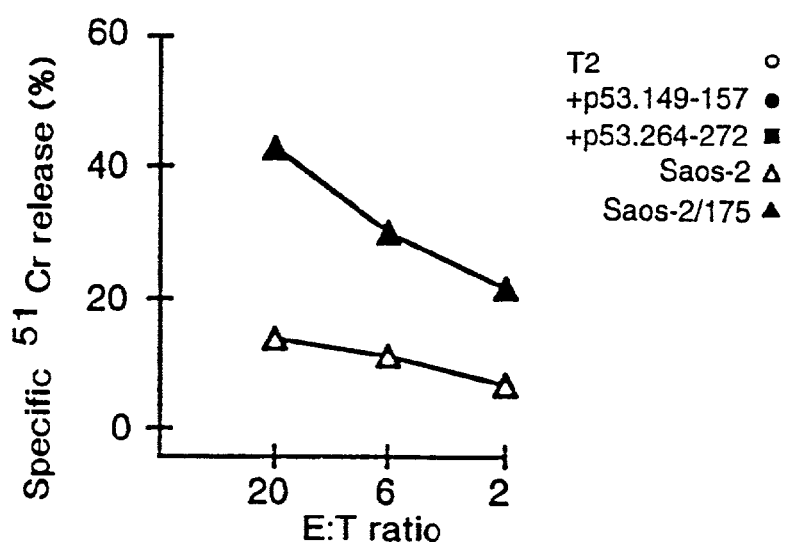

To test this hypothesis, polyclonal CTL lines specific for hu-p53.149-157 (CTL A2 149) and 264-272 (CTL A2 264) were established from peptide-primed A2.1-Tg mice (FIGS. 10E, G). Both CTL lines recognized endogenously synthesized p53-epitopes as illustrated by their lysis of Saos-2/175 transfectants (FIGS. 10F, H). Significantly, the magnitude of lysis of Saos-2/175 targets by CTL A2 149 and 264 was higher than that obtained by CTL from A2.1/$K^b$-Tg mice (FIG. 10B vs. 10F; FIG. 10D vs. 10H). Also, the concentrations of hu-p53.149-157 and 264-272 peptides required to obtain equivalent lysis of T2 targets by A2 vs. A2.1/$K^b$ derived CTL were 3- and 10-fold less, respectively (see FIGS. 11A and B). Thus, CTL of greater sensitivity for A2.1-p53-peptide complexes could be selected in A2.1-Tg as opposed to A2.1/$K^b$-Tg mice.

Figure 11A:
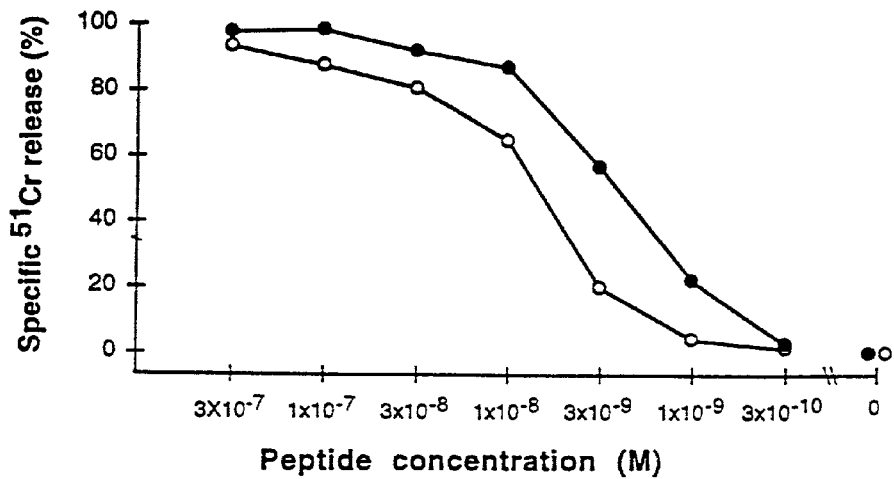
FIGS. 11A and B illustrate the efficiency of peptide recognition by p53-specific CTL lines. CTL lines specific for hu-wt-p53.149-157 and 264-272 were established from A2.1-Tg (CTL A2 149 and CTL A2 264) and A2.1/$K^b$-Tg mice (CTL A2/$K^b$ 149 and CTL A2/$K^b$ 264) and assayed at an E:T ratio of 10:1 for lytic activity against nonpeptide and p53.149-157-pulsed T2 (FIG. 11A) or nonpeptide and p53.264-272-pulsed T2 targets (FIG. 11B). Peptides were used at the indicated concentrations to pulse T2 targets after $^{51}$Cr labeling. Effector cells were CTL A2 149 (closed circles, ●), CTL A2/$K^b$ 149 (open circles, ○), CTL A2 264 (closed squares, ■) and CTL A2/$K^b$ 264 (open squares, □). The data represent the results of a 4-hour $^{51}$Cr release assay, whereby specific $^{51}$Cr release (%) is plotted against peptide concentration (M).
Figure 11B:
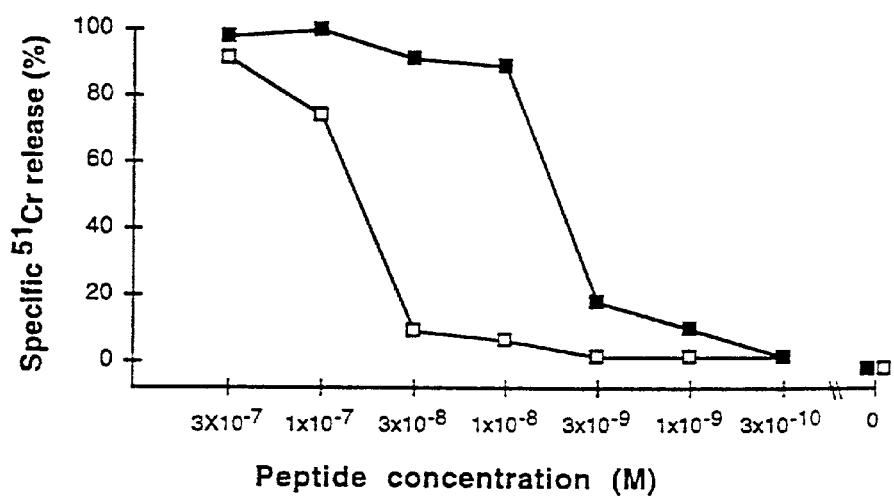

FIGS. 11A and B illustrate the efficiency of peptide recognition by p53-specific CTL lines. CTL lines specific for hu-wt-p53.149-157 (FIG. 11A) and 264-272 (FIG. 11B) were established from A2.1-Tg (CTL A2 149 and CTL A2 264) and A2.1/$K^b$-Tg mice (CTL A2/$K^b$ 149 and CTL A2/$K^b$ 264) and assayed at an E:T ratio of 10:1 for lytic activity against nonpeptide and p53.149-1 57-pulsed T2 (FIG. 11A) or nonpeptide and p53.264-272-pulsed T2 targets (FIG. 11B). Peptides were used at the indicated concentrations to pulse T2 targets after $^{51}$Cr labeling. Effector cells were CTL A2 149 (closed circles, ●), CTL A2/K$^b$ 149 (open circles, ○), CTL A2 264 (closed squares, ■) and CTL A2/K$^b$ 264 (open squares, □). The data represent the results of a 4-hour $^{51}$Cr release assay, whereby specific $^{51}$Cr release (%) is plotted against peptide concentration (M).

Having established CTL lines with apparently higher affinity for A2.1-p53-peptide complexes, the A2 149 and A2 264 CTL lines were tested for recognition of human tumor cell lines known to express high levels of p53 protein (MDA 231, BT 549, SW 480, Ramos A2.1, MCF7) (Table 5) (26-31 Bartek, et al., Id (1990); Nigro, et al., Id. (1989); Baker, et al., Id. (1990); Rodrigues, et al., Id. (1990); Gaidano, et al., Id. (1991); Takahashi, et al., Id. (1993)). These tumor cell lines were lysed by both p53-specific and alloreactive, A2.1-specific control CTL. Recognition was A2.1-restricted as lysis was inhibited by an A2.1-specific antibody (Table 5).

Table 5 shows the results obtained when human tumor cell lines that overexpressed p53-protein were lysed by A2.1-restricted, anti-p53.149-157 (CTL A2 149) and anti-p53.264-272 (CTL A2 264) CTL lines. Allo A2.1/K$^b$ CTL were alloreactive, A2.1-specific effector CTL and derived from Tg mice expressing functional human CD8α+β molecules (huCD8-Tg mice) (Sherman, et al., Id. (1992)) by a 6-day primary in vitro culture of huCD8-Tg spleen cells with irradiated A2.1/K$^b$-Tg spleen cell stimulators. RT 427 was an A2.1-restricted polyclonal CTL line established from peptide-primed (huCD8×A2.1/K$^b$) double-Tg mice and specific for a synthetic peptide representing residues 427-435 of HIV-1 RT. CTL were assayed for cytotoxicity in a 6-hour $^{51}$Cr release assay against the indicated human tumor cell lines, human dendritic cells, and Con A or PHA-activated lymphoblasts. Data are presented for noncytokine-treated Ramos and Ramos A2.1 targets, MDA 231 targets that had been treated with IFN-γ (20 ng/ml for 24 hours) and the remaining targets that had been treated with both IFN-γ (20 ng/ml for 24 hours) and TNF-α (3 ng/ml for 24 hours). Anti-A2.1 inhibition was performed by exposure of $^{51}$Cr labeled target cells to the anti-A2.1 monoclonal antibody PA2.1 (Parham and Bodmer, Nature 276): 397-8 (1978)) at saturating, nontoxic concentrations. ND denotes not determined.

of noncytokine-treated breast and colorectal cancer cell lines by p53-specific CTL was low (4% to 14% specific lysis at an E:T ratio of 10:1). Considering that MDA 231, MCF 7 and SW480 are not deficient in their ability to present endogenously synthesized peptides for recognition by class I MHC restricted CTL (Restifio, et al., J. Exp. Med. 177: 265-272 (1993)), the observed requirement for cytokines to achieve optimal lysis suggested that p53 peptides bound by A2.1 were presented in relatively low numbers by these tumor cells as compared with Saos-2/175 and that increased expression of A2.1-peptide complexes and adhesion molecules via cytokine treatment was required to facilitate TCR-mediated recognition and target cell lysis. In contrast, Burkitt lymphoma cells that had been transfected with A2.1 (Ramos A2.1) and had high-level expression of both the transfected gene product and p53 protein (see Gaidano, et al., Id 1991) were efficiently lysed by p53-specific CTL in the absence of cytokine stimulation. Again, their response was A2.1-restricted, as nontransfected Ramos targets were not lysed by p53 specific CTL.

No significant lysis by p53-specific CTL was evident against p53-deficient Saos-2 cells, or a variety of non-transformed targets, such as dendritic cells (Sallusto and Lanzavecchia, J. Exp. Med. 179: 1109-1118 (1994)), and activated lymphoblasts that had been shown to express low amounts of p53-protein following 3-to-4-day stimulation with Con A or PHA (Table 5). (See also Milner, Nature 310: 143-5 (1984).) These findings suggest that dividing and activated normal cells, even after exposure to cytokines, presented A2.1-bound p53 peptides in copy numbers too low to allow recognition by these CTL.

In summary, these results demonstrate presentation of peptides derived from p53 by a variety of human tumors at levels sufficient for recognition by CTL from A2-Tg mice. The observation that normal cells were not lysed does not necessarily indicate lack of presentation of p53 peptides, but rather insufficient levels of presentation for lysis by the CTL obtained in these studies. This may provide a window of opportunity for p53-directed immunotherapy.

TABLE 5

| | | | | Specific $^{51}$Cr release (%) by CTL | | | | | | |
|---|---|---|---|---|---|---|---|---|---|---|
| | | | | A2 149 | | | A2 264 | | | RT 427 | allo A2,1/K$^b$ |
| Target Cells | A2.1 | Tumor Type | E:T anti-A2 | 10 − | 10 + | 1 − | 10 − | 10 + | 1 − | 10 − | 10 − |
| MDA 231 | + | breast | | 24 | 5 | 16 | 31 | 10 | 19 | 6 | 47 |
| MCF7 | + | breast | | 38 | 13 | 28 | 79 | 38 | 67 | 8 | 52 |
| BT 549 | + | breast | | 53 | 37 | 18 | 79 | 47 | 35 | 14 | 61 |
| SW 480 | + | colorectal | | 55 | 26 | 41 | 59 | 17 | 24 | 4 | 67 |
| Ramos | − | Burkitt lymphoma | | 4 | 6 | 3 | 2 | 0 | 0 | 2 | 4 |
| Ramos A2.1 | + | Burkitt lymphoma | | 39 | 12 | 11 | 43 | 0 | 21 | 7 | 49 |
| Saos-2 | + | osteosarcoma | | 10 | 9 | 5 | 17 | 15 | 10 | 6 | 72 |
| Dendritic cells | + | | | 0 | 3 | 0 | 2 | 0 | 1 | 0 | ND |
| Con A lymphoblasts | + | | | 7 | 4 | 3 | 8 | 4 | 7 | 3 | 55 |
| PHA lymphoblasts | + | | 5 | 2 | 4 | 5 | 0 | 0 | 4 | 40 | |

No response was evident when an A2.1-restricted CTL line specific for an unrelated synthetic peptide, RT 427, was used as the effector cell source. Breast and colorectal cancer cell lines had to be pretreated with either IFN-γ (MDA 231) or both IFN-γ and TNF-α (MCF 7, BT 549, SW 480) in order to achieve optimal antigen-specific lysis by anti-p53 CTL. Lysis Whether CTL of sufficient TCR affinity to lyse p53-overexpressing tumors could be obtained by direct priming of tumor-bearing hosts is presently unknown.

Although the levels of p53 epitopes expressed by normal cells may not be sufficient to detect lysis, it is known that the amount of antigen required for tolerance is less than that required for effector cell recognition (Pircher, et al., Nature 351: 482-5 (1991); Karjalainen, Curr. Op. Immunol. 6: 9-12 (1994)). Such self-tolerance could result in deletion of T cells with receptors of sufficiently high affinity to detect p53 peptides on transformed cells, in which case it may be necessary to use Tg mice as a source of high affinity, hu-p53-specific TCRs for immunotherapy. Finally, although this example restricts its discussion to p53, the strategy described herein could be of value for the analysis of a variety of gene products that are specifically upregulated in malignant tumors and may represent potential targets for CTL-based immunotherapy and vaccine design.

Example 5

Her-2/neu Tumor Antigens Identified Using HLA Transgenic Mice

The most common source of tumor specific CTL has been tumor-infiltrating lymphocytes. There are, however a number of disadvantages to relying upon the immune system of the tumor-bearing host to provide such CTL. First, the isolation and the anti-tumor activity of these cells is dependent on their natural occurrence and their in vitro expansion. Second, these CTL represent a repertoire of specificities that have survived self-tolerance. Considering that the highest affinity cells specific for self antigens may have already been either eliminated or anergized, such cells may represent residual low affinity cells that may not be optimal for the task of tumor elimination in vivo. Third, it has been shown that after some period of time in the presence of the tumor cells, T cells can lose their functional activity by down-regulating the expression of the $\zeta$ chain of the CD3 complex or the $p^{56}$ lck molecules (Mizoguchi, et al., Science 258: 1795-1798 (1992)). In light of these considerations, it would be of value to identify an alternative source for obtaining CTL directed to TAA.

Ideally, one would like to obtain tumor-specific CTL by accessing a broad repertoire of CTL precursors. Based on strategies that have been successful in developing antibodies recognizing TAA (see, e.g., BlottiÄre, et al., Cancer Res. 51: 1537-1543 (1991)), such a repertoire could be established by generating xenogeneic CTL. Xenogeneic CTL specific for human TAA can function as a tool to identify class I associated peptides that may be targets of tumor specific vaccines.

Herein, among other disclosures, we describe tumor-specific xenogeneic CTL obtaining using transgenic mice expressing the human HLA-A2 and CD8 molecule. When immunized with appropriate A2-binding peptides, such mice can provide A2-restricted CTL. A2-binding peptides from the Her-2/neu proto-oncogene were used for immunization. Two A2-restricted T cell epitopes that are processed and presented in the context of HLA-A2 on a variety of tumor cell lines from different origins are described.

High level expression of the Her-2/neu proto-oncogene is associated with malignant transformation and aggressive disease, and therefore this protein represents an excellent target for T cell immunotherapy, as disclosed hereinabove. By way of providing additional support, the identification of further potential HLA A2.1-binding peptides from the Her-2/neu sequence is described herein.

Several Her-2/neu peptides were selected as candidate T cell epitopes. The immunogenicity of each peptide was evaluated by priming double transgenic mice expressing both the human CD8 and HLA A2.1 molecules with synthetic peptides corresponding to these sequences. Only two of six peptides were found to be immunogenic in that they could elicit peptide-specific CTL. Both CTL populations were able to specifically lyse A2.1-expressing human tumor cells originating from a variety of tissues. Direct evidence that tumors displayed these peptides was obtained by extraction of peptides from cell surface MHC molecules. These peptides and CTL may be used in developing new strategies for the treatment of human cancer, as disclosed herein.

A. Materials and Methods

1. Mice

The following transgenic lines were constructed and maintained at 20 The Scripps Research Institute (La Jolla, Calif.): A2.1/$K^b$, A2.1, CD8α+β.57. (Also see Vitiello, et al., J. Exp. Med. 173: 1007-1015 (1991); Sherman, et al., Science 258: 815-818 (1992).) CD8α+β.57 was crossed with the A2.1/$K^b$ transgenic to generate A2.1/$K^b$xCD8 mice. The C57BL/6 mice were purchased from the breeding colony of The Scripps Research Institute.

2. Cell Lines

Transfectants produced in our laboratory and used in these studies included EL4-A2.1/$K^b$, Jurkat A2/$K^b$ and Jurkat A2, and T2-A2/$K^b$ (Vitiello, et al., Id. (1991)). The breast carcinomas MCF-7, MDA-MB-231, BT549, the colon carcinoma SW480, the osteosarcoma U2-OS, the melanomas Malme-3M, SK-MEL-5, the glioblastoma T98G, ovarian carcinomas OVCAR-5, cervix carcinoma Caski were all purchased from the American Type Culture Collection (ATCC). Hepatoma Hep-G2 was obtained from Dr. Frank Chisari (The Scripps Research Institute). Saos-175 was obtained from Dr. Arnold Levine (Princeton University). The lung carcinoma NCI-H1355 was provided by Dr. A. F. Gazdar (The University of Texas, Southwestern Medical Center). Tumor cell lines were examined for cell surface expression of A2 and Her-2/neu by FACS analysis with anti-A2 mAb (BB7.2) and anti-c-NEU mAb (AB-5, Oncogene Science, Uniondale, N.Y.).

3. Peptide Synthesis

Her-2/neu-derived peptides were selected according to the known consensus motifs for peptides bound by A2.1 from the naturally-occurring sequences of the human Her-2/neu. (See, e.g., Ruppert, et al., Cell 74: 929-937 (1993); Yamamoto, et al., Nature 319: 230-234 (1986).) The peptides listed in Table 6 were synthesized on a peptide synthesizer (430A; Applied Biosystems, Foster, Calif.) as previously described (Sette, et al., J. Immunol 142: 0035 (1989)). The composition and purity of the peptides was ascertained by mass spectroscopy and HPLC analysis. The peptides were routinely determined to be greater than 90% pure.

TABLE 6

Her-2/neu Peptides Used for Immunization

| Peptide | Sequence # | SEQ ID NO | Sequence | Immunogenicity in Tg Mice |
|---|---|---|---|---|
| H3 | 369-377 | 10 | KIFGSLAFL | + |
| H6 | 444-453 | 11 | TLQGLGISSWL | – |
| H7 | 773-782 | 12 | VMAGVGSPYV | + |
| H8 | 546-555 | 13 | VLQGLPREYV | – |
| H9 | 661-669 | 14 | ILLVVVLGV | – |
| H11 | 654-662 | 37 | IISAVVGIL | – |
| HIV-9K | POL | 38 | KLVGKLNWA | + |

4. In Vitro Binding of Peptides to A2.1/$K^b$

The efficiency with which each Her-2/neu-specific peptide bound A2.1/$K^b$ was determined in a competitive binding assay (see Example 4 above). Each test peptide (10 mg) was incubated with radiolabeled target cells (T2-A2.1/$K^b$, 106 target cells labeled with 150 mCi $^{51}$Cr at 37° C. for 1.5 hours)

in the presence of a peptide derived from influenza A virus matrix protein (0.1 mg) which has high binding efficiency to A2.1/K$^b$, M(58-66). (See, e.g., Morrison, et al., *Eur. J. Immunol.* 22: 903-907 (1992).) Target cells were next incubated with a matrix peptide-specific CTL clone to assay for recognition of the pulsed-target cells. The binding of the test peptide to the target cells could be detected by the competitive inhibition of the binding of the M158-66) peptide as evidenced by a decrease in the ability of the influenza A-specific CTL to lyse the target cells.

5. Generation of CTL Populations

A2.1/KbxCD8 and/or A2.1 transgenic mice were immunized with each of the peptides listed in Table 6 to determine if they could stimulate A2.1-restricted CTL. Mice were immunized with a mixture of 100 mg of the Her-2/neu peptide with 120 mg "helper" peptide in 100ml Incomplete Freund's Adjuvant (IFA). (The helper peptide is an I-Ab restricted peptide derived from Hepatitis 8 virus core protein comprising amino acid residues 128 to 140 that induces a strong CD4 helper response (Sette, et al., *J. Immunol.* 153: 5586-5592 (1994).)

A2.1/K$^b$xCD8 or A2.1 lipopolysaccharide (LPS)-blasts were prepared as stimulators for in vitro restimulation of spleen cells from immunized mice. These were prepared by incubating spienocytes from A2/K$^b$ or A2.1 mice in complete RPMI containing 25 mg/ml LPS and 7 mg/ml dextran sulfate at 1.5×10$^6$ cells/ml in a total volume of 30 ml for 3 days. Murine spleen cells, collected 10 days after immunization, were restimulated in vitro with the irradiated (3000 rads) A2.1/K$^b$ or A2.1 LPS-blasts which had bound Her-2/neu specific peptides. Six days following in vitro restimulation, the CTL populations were assayed for lytic activity against T2-A2/K$^b$ target cells preincubated with the peptide used for stimulation (15 mM). The resultant Her-2/neu peptide-specific CTL populations were maintained in vitro by weekly restimulation. CTL populations were restimulated in 2 ml cultures by incubating with 0.1-0.2×10$^6$ irradiated Jurkat-A2.1 cells (20,000 rads) preincubated with Her-2/neu peptide (15 mM) and 5×10$^5$ irradiated C57BL/6 spleen cells (3000 rads) as fillers in media containing 2% (v/v) supernatant from concanavalin A-stimulated rat spleen cells (TCGF). (See Example 4.)

6. Cytotoxicity Assay

One hundred and six (106) target cells were incubated at 37° C. with 150 mCi of sodium $^{51}$Cr chromate for 90 minutes in the presence or absence of specific peptide. Cells were washed three times and resuspended in 5% RPMI. For the assay, 104 $^{51}$Cr-labeled target cells were incubated with different concentrations of effector cells in a final volume of 200 ml in U-bottomed 96-well plates. Supernatants were removed after 4-7 hrs at 37° C., and the percent specific lysis was determined by the following formula:

$$\% \text{ specific lysis} = 100 \times \frac{(\text{experimental release} - \text{spontaneous release})}{(\text{maximum release} - \text{spontaneous release})}.$$

7. Anti-A2 Blocking of Cytotoxicity

An anti-A2 mAb (PA2.1) was used to determine if CTL lysis was A2 restricted. (See Parham and Bodmer, *Nature* 276: 397-398 (1978).) Prior to the addition of the effector cells, tumor cells were incubated in the presence or absence of 0.5 mg/ml of the PA2.1 mAb.

8. Peptide Extraction

MHC-bound peptides were extracted from the surface of tumor cells as described by Storkus et. al. (*J. Immunol.* 151: 3719-3724. (1993)). In brief, confluent MDA-MB-231 and MCF-7 tumor cells were cultured in T175 flasks. These adherent tumor cells were washed twice with HBSS and incubated with 5 ml of acid buffer (0.131 M citric acid, 0.066M NA$_2$HPO$_4$, pH 3.0)/flask for one (1) minute. The acid-eluted supernatant was then concentrated on a SepPak Cl 8 cartridges (Waters) and eluted with 4 ml of 60% acetonitrile. The peptide preparation was lyophilized, resuspended in H$_2$O, and filtered through a Centricon 10 (Amicon) filter.

Concentrated peptides were loaded onto a reverse-phase C18 analytical column equilibrated with 0.1% trifluoroacetic acid, and the peptides were eluted with a linear 0-70% (v/v) acetonitrile gradient. One minute fractions were collected, lyophilized and resuspended in 100 ml of PBS and tested for the presence of antigenic peptide as described above.

B. Results

1. Selection of Immunogenic Peptides

Figure 12:
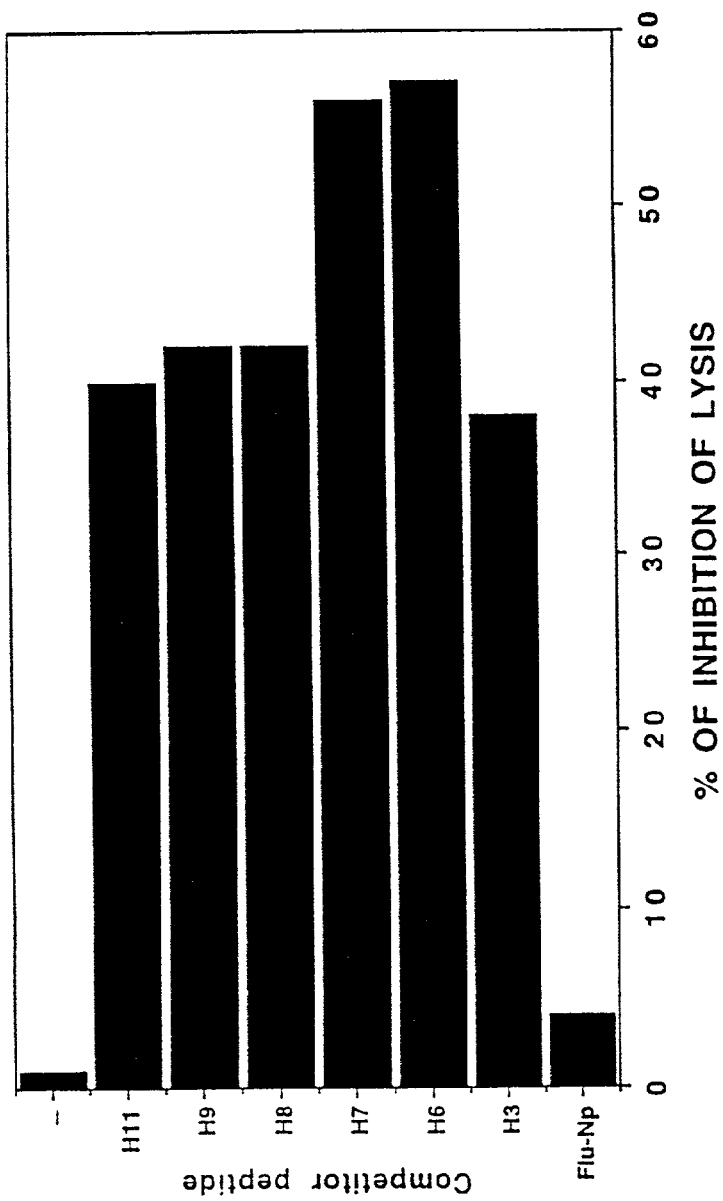
FIG. 12 illustrates the in vitro binding of peptides to A2.1/$K^b$. The efficiency with which each Her-2/neu-specific peptide bound A2.1/$K^b$ was determined in a competitive binding assay as described in Example 5 below. The binding of the test peptide to the target cells could be detected by the competitive inhibition of the binding of the influenza A-specific peptide as evidenced by a decrease in the ability of the influenza A-specific CTL to lyse the target cells. The competitor peptide is identified on the vertical axis; % inhibition of lysis is indicated on the horizontal axis. Data are given in percent inhibition of lysis by each of the peptides. No inhibition represented 71% lysis.

Peptide sequences from the human Her-2/neu protein containing the anchor motif for HLA-A2.1 (L, I, M, V, A, T position 2 and L, I, M, V, A, T position 8/9/10) were identified, and several of these were selected for synthesis. The A2 binding efficiency of synthesized peptides was determined by a competition assay measuring their ability to inhibit the binding to A2.1 of the influenza matrix protein peptide, M(58-66). In this assay, successful competition results in inhibition of lysis by an M(58-66)-specific, A2.1 restricted CTL clone as illustrated in FIG. 12. These results demonstrate that all of the Her-2/neu peptides synthesized were indeed able to bind A2, as indicated by inhibition of the binding of the M1 peptide.

FIG. 12 illustrates the in vitro binding of peptides to A2.1/K$^b$. The efficiency with which each Her-2/neu-specific peptide bound A2.1/K$^b$ was determined in a competitive binding assay as described herein. The binding of the test peptide to the target cells could be detected by the competitive inhibition of the binding of the influenza A-specific peptide as evidenced by a decrease in the ability of the influenza A-specific CTL to lyse the target cells. The competitor peptide is identified on the vertical axis; percent (%) inhibition of lysis is indicated on the horizontal axis. Data are given in percent inhibition of lysis by each of the peptides. No inhibition represented 71% lysis.

To determine if the Her-2/neu peptides were capable of stimulating an immune response in vivo, each peptide was used to immunize either A2.1/K$^b$xCD8 or A2.1 transgenic (Tg) mice. Spleen cells from injected animals were restimulated in vitro with irradiated syngeneic cells pulsed with the peptide used for in vivo priming.

Immunogenicity was evaluated by assaying these cultured cells for cytotoxicity against T2-A2.1/K$^b$ target cells pulsed with the priming peptide. A summary of the results is shown in Table 6. Only the H3 and the H7 peptides were able to stimulate a CTL response. An A2-restricted CTL population specific for an unrelated peptide from the HIV polymerase was also established for the purpose of utilization as a specificity control (see below). H3-and H7-specific CTL populations were established from both the A2.1xCD8 and A2.1 transgenic mice. CTL populations derived from either source demonstrated similar dose-dependency in their recognition of synthetic peptides in association with A2.1 molecules on T2 target cells (see FIG. 13).

Figure 13A:
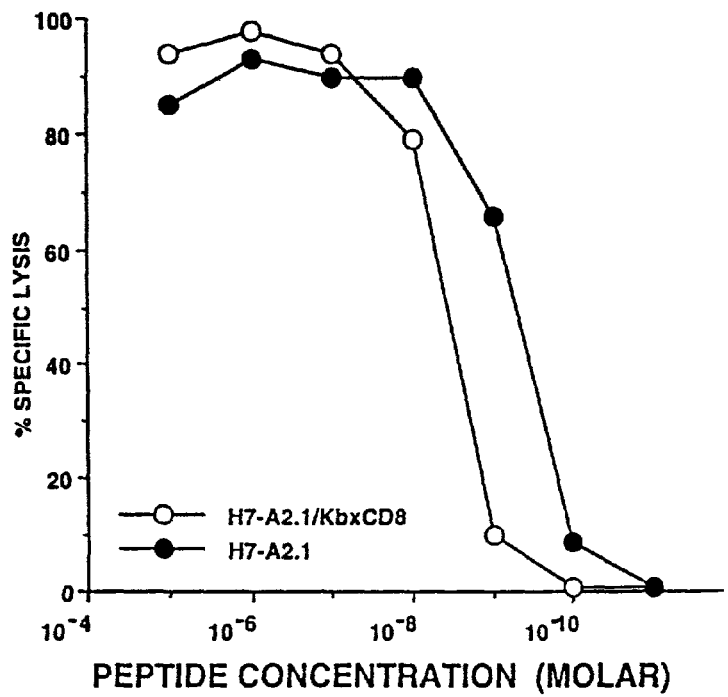
FIGS. 13A and B illustrate the efficiency of peptide recognition by Her-2/neu-specific CTL lines. The H7-and H3-specific CTLs established from A2.1-Tg or A2/$K^b$-Tg mice were assayed for lytic activity against the H7 and H3 peptides, respectively. Peptides were used to pulse T2 labeled targets at the indicated concentrations. Percent specific lysis is plotted against peptide concentration (molar).
Figure 13B:
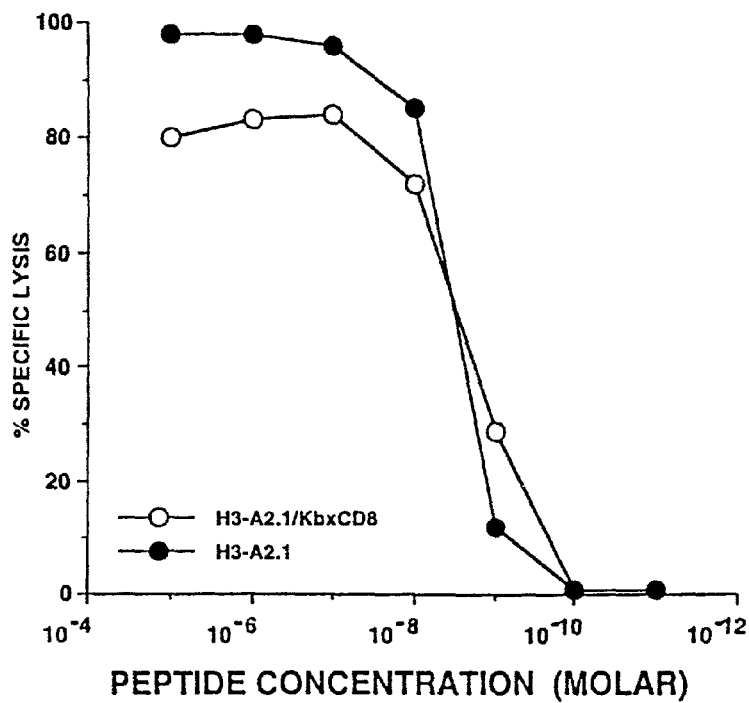
In FIG. 13B, open circles (○) represent H3-A2.1/$K^b$×CD8, while the closed circles (●) represent H3-A2.1. Data represent lysis at effector to target ratios (E:T) of 1:1 in a four-hour assay.

FIGS. 13A and B illustrate the efficiency of peptide recognition by Her-2/neu-specific CTL lines. The H7-and H3-specific CTLs established from A2.1-Tg or A2/K$^b$-Tg mice were assayed for lytic activity against the H7 and H3 peptides, respectively. Peptides were used to pulse T2 labeled targets at the indicated concentrations. Percent specific lysis is plotted against peptide concentration (molar). In FIG. 13A, the open circles (○) represent H7-A2.1/K$^b$xCD8, while the closed circles (●) represent H7-A2.1. In FIG. 13B, open circles (○) represent H3-A2.1/ K$^b$xCDB, while the closed circles (●) represent H3-A2.1. Data represent lysis at effector to target ratios (E:T) of 1:1 in a four-hour assay.

2. Lysis of Human Tumors by H3 and H7 Specific CTL

In order to determine if the H7 and H3 Her-2/neu synthesized peptides are endogenously processed and presented by cells in the context of A2.1, human tumor cell lines that expressed both A2.1 and Her-2/neu were used as targets for the peptide-induced CTL populations. Tumor cell lines were selected representing different tissues of origin (breast, ovarian, colon, melanoma, osteosarcoma, glioblastoma, and others) and characterized by FACS analysis for surface expression of A2 and Her-2/neu (data not shown). Tumor cells were preincubated for 24 hours prior to the assay in media supplemented with γ-interferon (γ-IFN, 20 ng/ml) plus tumor necrosis factor-α (TNF-α, 3 ng/ml). It is known that such pretreatment of tumor cells increases the expression of MHC I and adhesion molecules such as ICAM I on the surface of the cell thus enhancing their sensitivity to lysis by CTL. (See, e.g., Fisk, et al., *Lympho. & Cylokine Res*. 13: 125-131 (1994); Fady, et al., *Cancer Immunol. Immunother*. 37: 329-336 (1993).)

The results of these cytotoxicity experiments are summarized in Table 7. The data suggest that many different types of A2.1-expressing tumors were recognized by the H3-and H7-specific CTL. Lysis was found to be augmented by preincubation in the cytokine mixture, suggesting the cell lines are not highly efficient in antigen presentation. Included in all experiments was a CTL population specific for an unrelated HIV peptide that was not expressed by the cells (see Table 6).

Figure 14A:
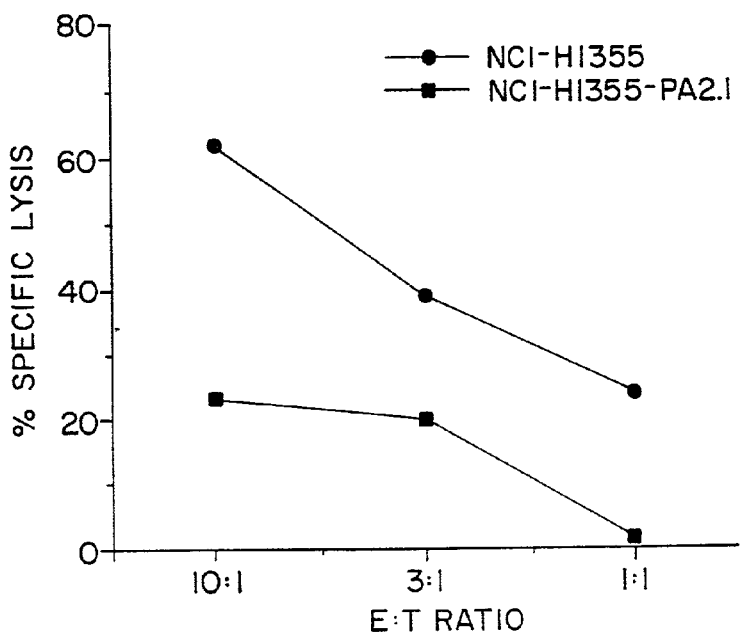
FIGS. 14A-D illustrate the inhibition of specific killing by anti-A2 antibody. An anti-A2 mAb (PA2.1) was used to determine if CTL lysis was A-2 restricted. Prior to the addition of the effector cells, tumor cells were incubated in the presence or absence of 0.5 mg/ml of PA2.1 mAb. Percent specific lysis is plotted against E:T ratio in each of FIGS. 14A-D.
Figure 14B:
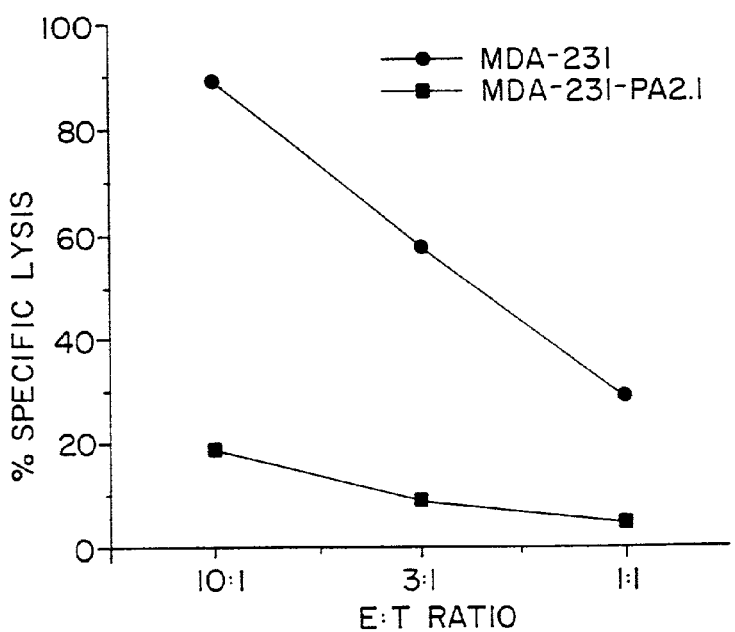
Figure 14C:
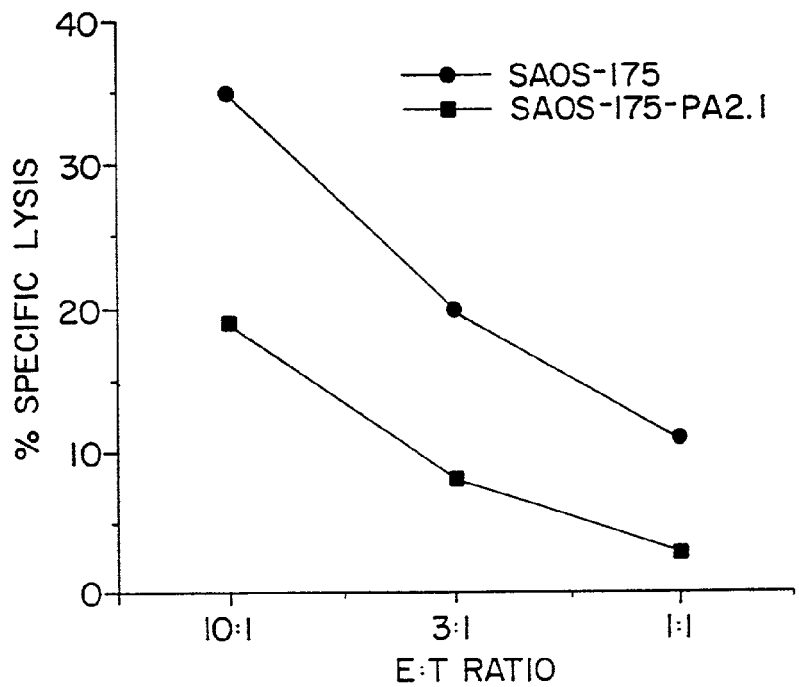
Figure 14D:
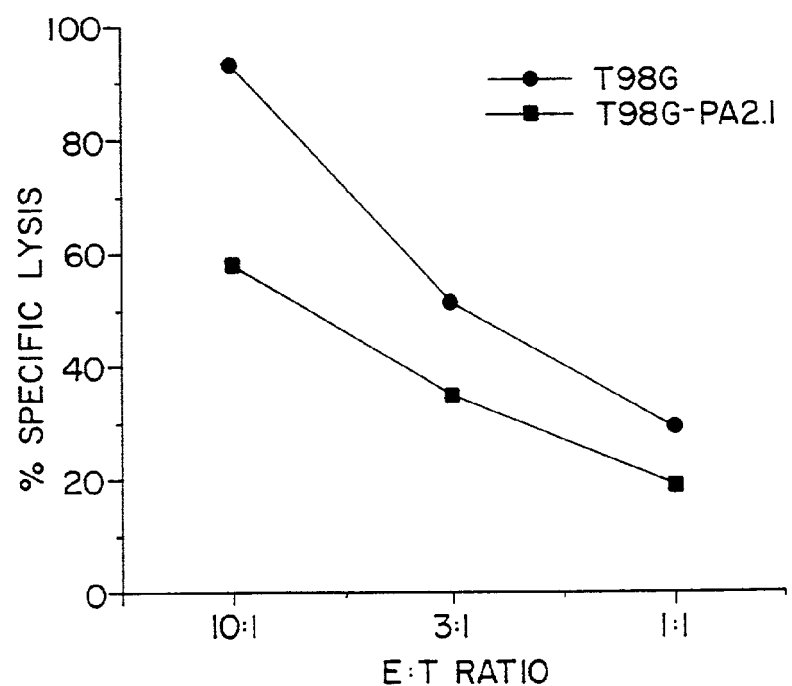
Figure 15A:
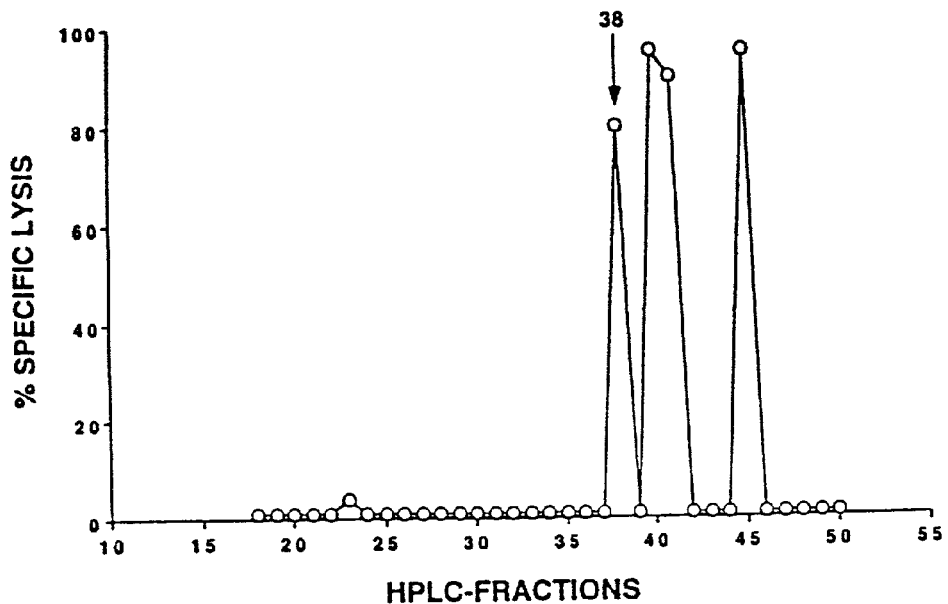
FIGS. 15A-D show that H3 and H7 peptides are presented on the surface of tumor cells. Peptides from the MDA.MB.231 and MCF-7 tumor cell lines were extracted by acid elution and fractionated as described in Example 5, using a C18 analytical column. Following HPLC fractionation, the samples were lyophilized and resuspended in 100 μl of PBS. Fifty (50) μl of each fraction from MDA.MB.231 (FIGS. 15A and 15C) and MCF-7 (FIGS. 15B and 15D) were used to pulse T2-A2$K^b$ target cells and assayed for recognition by the H3 (FIGS. 15A and 15B) and H7 (FIGS. 15C and 15D) CTL populations. Data represents lysis at E:T 10.1 in a four-hour assay. In each of FIGS. 15A-D, % specific lysis is plotted against HPLC-Fractions.
Figure 15B:
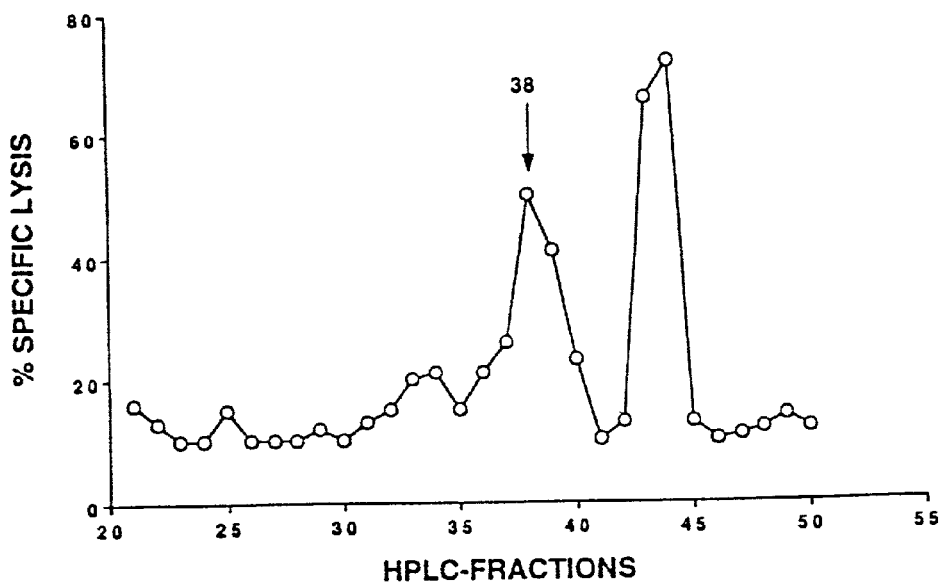
Figure 15C:
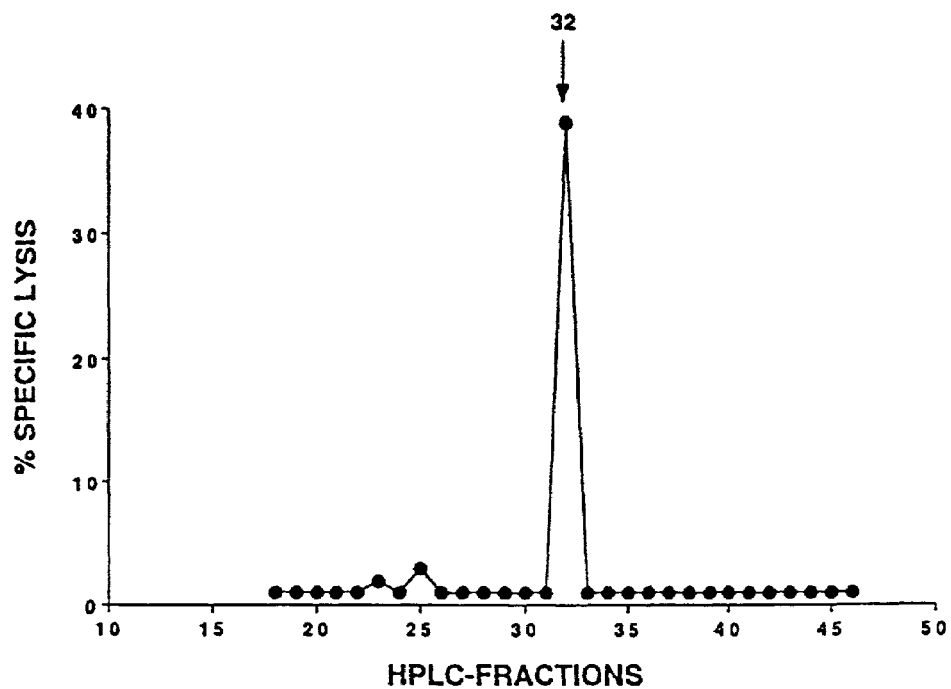
Figure 15D:
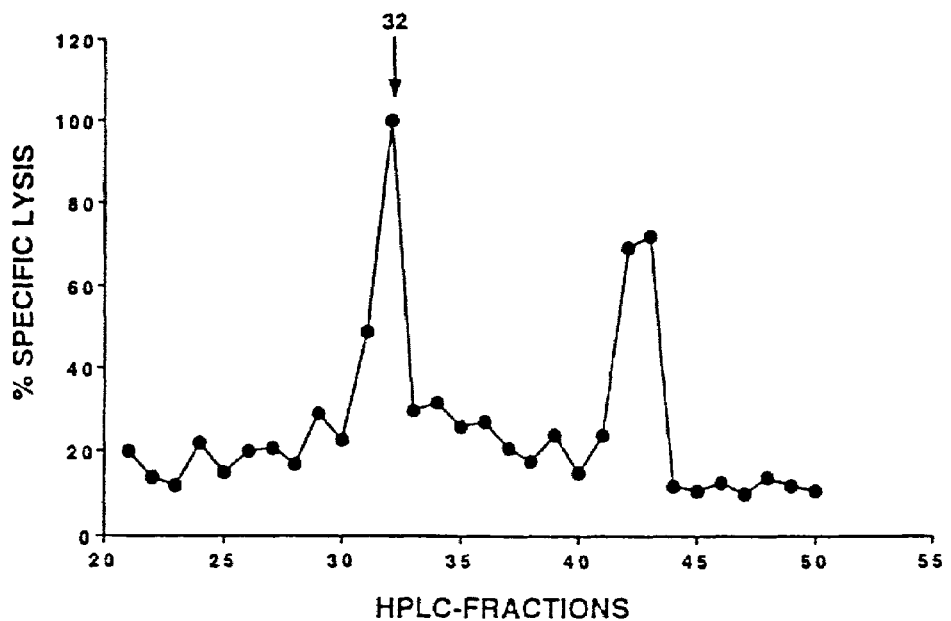

FIGS. 14A-D illustrate the inhibition of specific killing by anti-A2 antibody. An anti-A2 mAb (PA2.1) was used to determine if CTL lysis was A-2 restricted. Prior to the addition of the effector cells, tumor cells were incubated in the presence or absence of 0.5 mg/ml of PA2.1 mAb. Percent specific lysis is plotted against E:T ratio in each of FIGS. 14A-D. In FIG. 14A, closed circles (●) represent NCI-H1355, while closed squares (■) represent NCI-H1355-PA2.1. In FIG. 14B, closed circles (●) represent MDA-231, while closed squares (■) represent MDA-231-PA2.1. In FIG. 14C, closed circles (●) represent SAOS-175, while closed squares (■) represent SAOS-175-PA2.1. In FIG. 14D, closed circles (●) represent T98G, while closed squares (■) represent T98G-PA2.1. Similar results were obtained with the H3 CTL (data not shown).

3. Extraction of H3 and H7 Peptides from Tumor Cells

The fact that expression of both Her-2/neu and HLA A2.1 was required to obtain target cell lysis by the H3-and H7-specific populations suggested the target epitopes on the tumor cells were indeed the same peptides against which the CTL were originally generated. However, it is always possible that lysis is specific for a cross-reactive epitope, and therefore we wished to confirm the CTL were indeed recognizing the H3 and H7 peptides presented by the human tumors. Peptides from the MDA-MB-231 and MCF-7 cells were extracted from MHC molecules on the cell surface by acid elution and then fractionated by reverse-phase HPLC. T2-A2/K$^b$ targets were pulsed with a portion of each HPLC fraction.

As illustrated in FIG. 15, the H3 CTL recognized a peptide that elutes at fraction 38 and the H7 CTL recognized a peptide that elutes at fraction 32 from either the MDA-MB-231 or MCF-7 cell lines. These positions correspond to the elution

TABLE 7

Killing of Tumors Expressing Her-2/neu

| Tumor | Type | A2 | Her-2 | H7 | H7 + CYT | H3 | H3 + CYT | HIV-9K | HIV-9K + CYT |
|---|---|---|---|---|---|---|---|---|---|
| MDA.M8231 | Breast | + | + | 26 | 89 | 34 | 85 | 3 | 14 |
| MCF-7 | Breast | + | + | 7 | 40 | 7 | 54 | 3 | 7 |
| BT549 | Breast | + | + | 2 | 36 | 2 | 40 | 2 | 15 |
| SAOS.175 | Osteosarcoma | + | + | 27 | 35 | 27 | 33 | 18 | 11 |
| U2-OS | Osteosarcoma | + | + | 30 | 62 | 32 | 91 | 18 | 24 |
| SW480 | Colon | + | + | 2 | 17 | 6 | 50 | 1 | 4 |
| OVCAR-5 | Ovarian | + | + | 13 | 23 | 25 | 29 | 10 | 12 |
| T98G | Glioblastoma | + | + | 29 | 93 | 20 | 99 | 9 | 13 |
| MALME-3M | Melanoma | + | + | 4 | 14 | 28 | 57 | 2 | 1 |
| SKMEL-5 | Melanoma | + | + | 16 | 40 | 6 | 38 | 5 | 4 |
| NCI.H1355 | Lung | + | + | 13 | 62 | 11 | 38 | 7 | 25 |
| Hep-G2 | Hepatoma | + | + | 4 | 29 | 4 | 20 | 1 | 8 |
| CASKI | Cervix | + | + | 9 | 20 | 13 | 30 | 8 | 11 |
| U87G | Glioblastoma | + | − | 1 | 1 | 2 | 1 | 5 | 1 |
| ST486 | Lymphoma | + | − | 5 | 8 | 1 | 1 | 1 | 1 |
| LG-2 | EBV-trans. | + | − | 1 | 3 | 2 | 4 | 1 | 1 |
| SV80 | Fibroblast | + | − | 2 | 2 | 4 | 8 | 2 | 2 |
| JY | Lymphoma | + | − | 4 | 2 | 2 | 1 | 2 | 1 |
| MDA.MB435 | Breast | − | + | 1 | 1 | 3 | 2 | 4 | 3 |

The degree of lysis exhibited by each target in the presence of this population represented non-specific background lysis. In addition, blocking experiments were performed with the anti-A2 mAb, PA2-1, to confirm A2 was involved in target cell recognition. As illustrated in FIG. 14, incubation of target cells and CTL in the presence of the anti-A2 mAb significantly decreased the ability of CTL to specifically lyse the tumors.

position of the synthetic peptides, confirming that the tumor cells are lysed due to their presentation of these same peptides.

FIGS. 15A-D show that H3 and H7 peptides are presented on the surface of tumor cells. Peptides from the MDA.MB.231 and MCF-7 tumor cell lines were extracted by acid elution and fractionated as described herein, using a C18 analytical column. Following HPLC fractionation, the samples were lyophilized and resuspended in 100 μl of PBS.

Fifty (50) µl of each fraction from MDA.MB.231 (FIGS. 15A and 15C) and MCF-7 (FIGS. 15B and 15D) were used to pulse T2-A2K$^b$ target cells and assayed for recognition by the H3 (FIGS. 15A and 15B) and H7 (FIGS. 15C and 15D) CTL populations. Data represent lysis at E:T 10:1 in a four-hour assay. In each of FIGS. 15A-D, percent (%) specific lysis is indicated for each of the HPLC-Fractions.

C. Discussion

Identification of antigens shared by tumors originating from different tissues remains a major goal of tumor immunology. We have focused on the immunogenicity of proteins such as p53 and Her-2/neu that are expressed at high levels in a broad spectrum of tumors. (See, e.g., Slamon, et al., *Science* 235: 177-182 (1987); DePotter, et al., *Int. J. Cancer* 44: 969-974 (1989).) In the present example, potential A2-binding peptides from Her-2/neu were selected according to A2-anchor motifs, and their ability to stimulate an A2.1-restricted response was assessed by immunization of A2-transgenic mice.

Several previous studies have verified the validity of such an approach in identifying A2-restricted human antigens. Recently several laboratories have reported that A2.1-Tg mice respond to the same peptides from Hepatitis C recognized by HLA-A2.1 human CTL (Sette, et al., *J. Immunol.* 153: 5586-5592 (1994); Shirai, et al., *J. Immunol.* 154: 2733-2742 (1995)). This confirmed previous work, which demonstrated that humans and HLA A2/K$^b$ transgenic mice both select the same A2-restricted antigenic epitopes from influenza (Vitiello, et al., *J. Exp. Med.* 173: 1007-1015 (1991); Man, et al., *J. Immunol.* 153: 4458-67 (1994)).

The use of HLA transgenic mice in identifying potential antigenic peptides presents a number of advantages. Most obvious among these is the ability to prime in vivo. This not only provides a method to test immunogenicity of candidate antigenic peptides, it also assures that CTL populations are of relatively high avidity.

Although methods have been developed to stimulate primary CTL in vitro, these methods often provide CTL populations of low avidity and may not lyse cells that display limited amounts of endogenously processed peptide (Speiser, et al., *J. Immunol.* 149: 972-980 (1992)). Based on results disclosed herein and in studies of antigenic peptides from human p53 (see Ex. 4 above), the CTL obtained by peptide immunization of HLA transgenic mice were able to recognize endogenously-processed-and-presented human tumor antigens. The identification of T cell epitopes derived from proteins expressed at high levels in a broad spectrum of tumors may define such proteins as tumor-associated antigens that are of interest as a target of a therapeutic anti-tumor T cell response.

Only two of the Her-2/neu peptides investigated were able to raise a response in animals. Included among those which could not elicit a response was the H11 peptide which was previously identified on the basis of its recognition by human TILs (Peoples, et al., *PNAS USA* 92: 432-436 (1995)). The reason for this discrepancy is not known; however, it presents the possibility that for some peptides, differences may exist in immunogenicity between mouse and human. Further investigation would be necessary to determine if this is the case, and if so, how generally it may apply. However, Fisk et al. recently reported a Her-2/neu-derived nonapeptide (E75) as an antigen recognized by human CTL (*J. Exp. Med.* 181: 2109-2117 (1995)). The E75 sequence is identical to H3 peptide. This confirms once more that the A2.1-Tg can recognize the same peptides as seen by the HLA A2 human CTLs. It will be of interest to determine if the H7 peptide can also be recognized by human T cells.

Definitive evidence that human tumors processed and presented the H3 and H7 peptides was obtained by acid elution of peptides from cell surface MHC molecules. H3 and H7 peptides were among those peptides obtained from the two different tumors examined, MDA 237 and MCF 7. The basis for recognition of peptides eluting at other positions is unclear. Detection of more than one active peptide peak is a relatively common occurrence and may be due to cross-reaction with other peptides, or due to different size peptides containing the identical sequence (Udaka, et al., *Cell* 69: 989-998 (1992)

The ability of the H3 and H7 CTL populations to kill specifically A2+Her-2/neu+human tumors from different tissue origin suggests the H3 and H7 peptides were presented by most A2.1+tumors that express Her-2/neu. However, there were marked differences in the amount of lysis among the tumors examined. This could be due to the variation in the level of HLA-A2 expressed, antigen processing or the levels of Her-2/neu. Cytotoxicity could be enhanced by pretreatment of the tumors with cytokines (γ-INF, TNF-a) which are known to increase HLA-A2 expression (Fisk, et al., *Lympho. & Cytokine Res.* 13: 125-131 (1994); Nistico, et al., *Cancer Res.* 50: 7422 (1990)), antigen processing (Greiner, et al., *Cancer Treat. Res.* 51: 413 (1990); Mortarini, et al., *Int. J. Cancer* 45: 334 (1990)) and induction of ICAM expression (Fady, et al., *Cancer Immunol. Immunother.* 37: 329-336 (1993)). The potential to use CTL as an effective anti-tumor therapy may depend on co-delivery of such cytokines (Schmidt-Wolf, G. and 1. G. H. Schmidt-Wolf, *Eur. J. Immunol.* 25: 1137-1140 (1995)).

Her-2/neu is highly conserved among vertebrates. The regions of the molecule represented by the H3 and H7 peptides are identical in rat and human (Yamamoto, et al., *Nature* 319: 230-234 (1986); Bargmann, et al., *Nature* 319: 226-230 (1986)), and therefore are likely to be identical in human and mouse. Despite such sequence conservation, these peptides proved to be immunogenic in the transgenic mice. The apparent lack of tolerance of Her-2/neu would explain the presence of TILs specific for Her-2/neu peptides in tumor-bearing patients as reported by various groups (see, e.g., Ioannides, et al., *Cellular Immunol.* 151: 225-234 (1993); Yoshino, et al., *Cancer Res* 54: 3387-3390 (1994)).

It is known that Her-2/neu is not widely expressed, either in embryonic stages or in adult tissues (Natali, et al., *Int. J. Cancer* 45: 457-461 (1990); Press, et al., *Oncogene* 5: 953-962 (1990)). Boon et al. (*Ann. Rev. Immunol.* 12: 337-65 (1994)) have proposed that tumor antigens recognized by T cells fall into three categories: (1) novel sequences generated by point mutations; (2) tumor antigens that are identical to the germline sequence, but are not expressed in any normal tissue; and (3) genes encoding tumor antigens that are specific differentiation antigens. Her-2/neu could fall into the latter category. The detection of an immune response against the Her-2/neu peptides, without any evidence of autoimmune destruction of normal tissue, encourages the potential for vaccine development for tumor immunotherapy.

The foregoing specification, including the specific embodiments and examples, is intended to be illustrative of the present invention and is not to be taken as limiting. Numerous other variations and modifications can be effected without departing from the true spirit and scope of the present invention.

I claim:

1. A method of specifically activating cytotoxic T lymphocytes in an animal having a breast cancer that overexpresses a Her-2/Neu protein, the method comprising the step of administering the polypeptide of SEQ ID NO:12 to said animal, thereby activating cytotoxic T lymphocytes in the animal.

2. A method of treating a patient having a breast cancer overexpressing a Her-2/Neu protein, the method comprising the step of administering the polypeptide of the amino acid sequence VMAGVGSPYV (SEQ ID NO:12) to the patient, thereby treating the breast cancer in the patient.

3. The method of claim 2, wherein said polypeptide is incorporated into a pharmaceutical composition distant comprising a pharmaceutically acceptable carrier.

4. The method of claim 2, wherein said polypeptide is linked to a carrier.

5. The method of claim 2, wherein said polypeptide is administered to said patient as a homopolymer.

6. The method of claim 2, further comprising the step of administering a second component to said patient, wherein said second component primes cytotoxic T lymphocytes (CTLs) for activation.

7. The method of claim 6, wherein the second component is tripalmitoyl-S-glycerylcysteinyl-seryl-serine (P3CSS).

8. The method of claim 2, further comprising the step of administering a second polypeptide to said animal.

9. The method of claim 8, wherein the second polypeptide is TPPAYRPPNAPIL (SEQ ID NO:9).

10. The method of claim 1, wherein said polypeptide is incorporated into a pharmaceutical composition further comprising a pharmaceutically acceptable carrier.

11. The method of claim 1, wherein said polypeptide is linked to a carrier.

12. The method of claim 1, wherein said polypeptide is administered to said animal as a homopolymer.

13. The method of claim 1, wherein said immunizing step further comprises administering a second component to said animal, wherein said second component primes said CTLs for activation.

14. The method of claim 13, wherein said second component is tripalmitoyl-S-glycerylcysteinyl-seryl-serine (P3CSS).

15. The method of claim 1, wherein the immunizing step further comprises administering a second polypeptide to said animal.

16. The method of claim 15, wherein the second polypeptide is TPPAYRPPNAPIL (SEQ ID NO:9).

* * * * *

UNITED STATES PATENT AND TRADEMARK OFFICE
CERTIFICATE OF CORRECTION

PATENT NO. : 7,402,314 B2 Page 1 of 1
APPLICATION NO. : 09/277064
DATED : July 22, 2008
INVENTOR(S) : Linda A. Sherman It is certified that error appears in the above-identified patent and that said Letters Patent is hereby corrected as shown below:

On the Title Page insert:

--Related U.S. Application Data

Item (62) This application is a divisional of U.S. patent application Ser. No. 08/860,232 (filed on Aug. 8, 1997, now abandoned), which is a national phase entry of PCT/US95/16415, (filed on Dec. 14, 1995), which claims priority to U.S. patent application Ser. No. 08/355,558 (filed on Dec. 14, 1994, now abandoned).--

Signed and Sealed this

Twenty-third Day of September, 2008

JON W. DUDAS
*Director of the United States Patent and Trademark Office*

SEQUENCE LISTING

<160> NUMBER OF SEQ ID NOS: 39

<210> SEQ ID NO 1
<211> LENGTH: 11
<212> TYPE: PRT
<213> ORGANISM: Homo sapiens

<400> SEQUENCE: 1

Leu Leu Pro Glu Asn Asn Val Leu Ser Pro Leu
 1               5                  10

<210> SEQ ID NO 2
<211> LENGTH: 9
<212> TYPE: PRT
<213> ORGANISM: Homo sapiens

<400> SEQUENCE: 2

Arg Met Pro Glu Ala Ala Pro Pro Val
 1               5

<210> SEQ ID NO 3
<211> LENGTH: 9
<212> TYPE: PRT
<213> ORGANISM: Homo sapiens

<400> SEQUENCE: 3

Ser Thr Pro Pro Pro Gly Thr Arg Val
 1               5

<210> SEQ ID NO 4
<211> LENGTH: 9
<212> TYPE: PRT
<213> ORGANISM: Homo sapiens

<400> SEQUENCE: 4

Leu Leu Gly Arg Asn Ser Phe Glu Val
 1               5

<210> SEQ ID NO 5
<211> LENGTH: 9
<212> TYPE: PRT
<213> ORGANISM: Human immunodeficiency virus

<400> SEQUENCE: 5

Ile Leu Lys Glu Pro Val His Gly Val
 1               5

<210> SEQ ID NO 6
<211> LENGTH: 9
<212> TYPE: PRT
<213> ORGANISM: Influenza A virus

<400> SEQUENCE: 6

Ala Ser Asn Glu Asn Met Glu Thr Met
 1               5

<210> SEQ ID NO 7
<211> LENGTH: 8
<212> TYPE: PRT
<213> ORGANISM: Vesicular stomatitis virus

<400> SEQUENCE: 7

Arg Gly Tyr Val Tyr Gln Gly Leu

```
<210> SEQ ID NO 8
<211> LENGTH: 9
<212> TYPE: PRT
<213> ORGANISM: Influenza A virus

<400> SEQUENCE: 8

Gly Ile Leu Gly Phe Val Phe Thr Leu
 1               5

<210> SEQ ID NO 9
<211> LENGTH: 13
<212> TYPE: PRT
<213> ORGANISM: Hepatitis B virus

<400> SEQUENCE: 9

Thr Pro Pro Ala Tyr Arg Pro Pro Asn Ala Pro Ile Leu
 1               5                  10

<210> SEQ ID NO 10
<211> LENGTH: 9
<212> TYPE: PRT
<213> ORGANISM: Homo sapiens

<400> SEQUENCE: 10

Lys Ile Phe Gly Ser Leu Ala Phe Leu
 1               5

<210> SEQ ID NO 11
<211> LENGTH: 10
<212> TYPE: PRT
<213> ORGANISM: Homo sapiens

<400> SEQUENCE: 11

Thr Leu Gln Gly Leu Gly Ile Ser Trp Leu
 1               5                  10

<210> SEQ ID NO 12
<211> LENGTH: 10
<212> TYPE: PRT
<213> ORGANISM: Homo sapiens

<400> SEQUENCE: 12

Val Met Ala Gly Val Gly Ser Pro Tyr Val
 1               5                  10

<210> SEQ ID NO 13
<211> LENGTH: 10
<212> TYPE: PRT
<213> ORGANISM: Homo sapiens

<400> SEQUENCE: 13

Val Leu Gln Gly Leu Pro Arg Glu Tyr Val
 1               5                  10

<210> SEQ ID NO 14
<211> LENGTH: 9
<212> TYPE: PRT
<213> ORGANISM: Homo sapiens

<400> SEQUENCE: 14

Ile Leu Leu Val Val Val Leu Gly Val
 1               5
```

```
<210> SEQ ID NO 15
<211> LENGTH: 10
<212> TYPE: PRT
<213> ORGANISM: Homo sapiens

<400> SEQUENCE: 15

Val Leu Ser Pro Leu Pro Ser Gln Ala Met
 1               5                  10

<210> SEQ ID NO 16
<211> LENGTH: 9
<212> TYPE: PRT
<213> ORGANISM: Homo sapiens

<400> SEQUENCE: 16

Asp Leu Met Leu Ser Pro Asp Asp Ile
 1               5

<210> SEQ ID NO 17
<211> LENGTH: 10
<212> TYPE: PRT
<213> ORGANISM: Homo sapiens

<400> SEQUENCE: 17

Leu Met Leu Ser Pro Asp Asp Ile Glu Gln
 1               5                  10

<210> SEQ ID NO 18
<211> LENGTH: 11
<212> TYPE: PRT
<213> ORGANISM: Homo sapiens

<400> SEQUENCE: 18

Ala Ala Pro Pro Val Ala Pro Ala Pro Ala Ala
 1               5                  10

<210> SEQ ID NO 19
<211> LENGTH: 9
<212> TYPE: PRT
<213> ORGANISM: Homo sapiens

<400> SEQUENCE: 19

Val Ala Pro Ala Pro Ala Ala Pro Thr
 1               5

<210> SEQ ID NO 20
<211> LENGTH: 9
<212> TYPE: PRT
<213> ORGANISM: Homo sapiens

<400> SEQUENCE: 20

Ala Ala Pro Thr Pro Ala Ala Pro Ala
 1               5

<210> SEQ ID NO 21
<211> LENGTH: 10
<212> TYPE: PRT
<213> ORGANISM: Homo sapiens

<400> SEQUENCE: 21

Arg Leu Gly Ile Leu His Ser Gly Thr Ala
 1               5                  10

<210> SEQ ID NO 22
```

```
<211> LENGTH: 9
<212> TYPE: PRT
<213> ORGANISM: Homo sapiens

<400> SEQUENCE: 22

Gly Thr Ala Lys Ser Val Thr Cys Thr
 1               5

<210> SEQ ID NO 23
<211> LENGTH: 9
<212> TYPE: PRT
<213> ORGANISM: Homo sapiens

<400> SEQUENCE: 23

Ser Val Thr Cys Thr Tyr Ser Pro Ala
 1               5

<210> SEQ ID NO 24
<211> LENGTH: 9
<212> TYPE: PRT
<213> ORGANISM: Homo sapiens

<400> SEQUENCE: 24

Val Thr Cys Thr Tyr Ser Pro Ala Leu
 1               5

<210> SEQ ID NO 25
<211> LENGTH: 9
<212> TYPE: PRT
<213> ORGANISM: Homo sapiens

<400> SEQUENCE: 25

Ala Leu Asn Lys Met Phe Cys Gln Leu
 1               5

<210> SEQ ID NO 26
<211> LENGTH: 9
<212> TYPE: PRT
<213> ORGANISM: Homo sapiens

<400> SEQUENCE: 26

Gln Leu Ala Lys Thr Cys Pro Val Gln
 1               5

<210> SEQ ID NO 27
<211> LENGTH: 10
<212> TYPE: PRT
<213> ORGANISM: Homo sapiens

<400> SEQUENCE: 27

Trp Val Asp Ser Thr Pro Pro Gly Thr
 1               5                  10

<210> SEQ ID NO 28
<211> LENGTH: 9
<212> TYPE: PRT
<213> ORGANISM: Homo sapiens

<400> SEQUENCE: 28

Ala Ile Tyr Lys Gln Ser Gln His Met
 1               5

<210> SEQ ID NO 29
<211> LENGTH: 11
<212> TYPE: PRT
```

<213> ORGANISM: Homo sapiens

<400> SEQUENCE: 29

Gly Leu Ala Pro Pro Gln His Leu Ile Arg Val
1               5                   10

<210> SEQ ID NO 30
<211> LENGTH: 9
<212> TYPE: PRT
<213> ORGANISM: Homo sapiens

<400> SEQUENCE: 30

Asn Thr Phe Arg His Ser Val Val Val
1               5

<210> SEQ ID NO 31
<211> LENGTH: 9
<212> TYPE: PRT
<213> ORGANISM: Homo sapiens

<400> SEQUENCE: 31

Cys Thr Thr Ile His Tyr Asn Tyr Met
1               5

<210> SEQ ID NO 32
<211> LENGTH: 11
<212> TYPE: PRT
<213> ORGANISM: Homo sapiens

<400> SEQUENCE: 32

Ile Thr Leu Glu Asp Ser Ser Gly Asn Leu Leu
1               5                   10

<210> SEQ ID NO 33
<211> LENGTH: 10
<212> TYPE: PRT
<213> ORGANISM: Homo sapiens

<400> SEQUENCE: 33

Asn Leu Leu Gly Arg Asn Ser Phe Glu Val
1               5                   10

<210> SEQ ID NO 34
<211> LENGTH: 9
<212> TYPE: PRT
<213> ORGANISM: Homo sapiens

<400> SEQUENCE: 34

Pro Leu Asp Gly Glu Tyr Phe Thr Leu
1               5

<210> SEQ ID NO 35
<211> LENGTH: 9
<212> TYPE: PRT
<213> ORGANISM: Homo sapiens

<400> SEQUENCE: 35

Glu Met Phe Arg Glu Leu Asn Glu Ala
1               5

<210> SEQ ID NO 36
<211> LENGTH: 9
<212> TYPE: PRT
<213> ORGANISM: Mus musculus

-continued

```
<400> SEQUENCE: 36

Leu Leu Gly Arg Asp Ser Phe Glu Val
 1               5

<210> SEQ ID NO 37
<211> LENGTH: 9
<212> TYPE: PRT
<213> ORGANISM: Homo sapiens

<400> SEQUENCE: 37

Ile Ile Ser Ala Val Val Gly Ile Leu
 1               5

<210> SEQ ID NO 38
<211> LENGTH: 9
<212> TYPE: PRT
<213> ORGANISM: Human immunodeficiency virus

<400> SEQUENCE: 38

Lys Leu Val Gly Lys Leu Asn Trp Ala
 1               5

<210> SEQ ID NO 39
<211> LENGTH: 6
<212> TYPE: PRT
<213> ORGANISM: Escherichia coli

<400> SEQUENCE: 39

Ala Gly Gly Ala Gly Gly
 1               5
```